(12) United States Patent
Beratan

(10) Patent No.: US 9,000,373 B2
(45) Date of Patent: *Apr. 7, 2015

(54) OPTICALLY TRANSITIONING THERMAL DETECTOR STRUCTURES

(71) Applicant: L-3 Communications Corporation, New York, NY (US)

(72) Inventor: Howard Beratan, Pittsburgh, PA (US)

(73) Assignee: L-3 Communications Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/930,844

(22) Filed: Jun. 28, 2013

(65) Prior Publication Data

US 2013/0292789 A1 Nov. 7, 2013

Related U.S. Application Data

(63) Continuation of application No. 12/799,628, filed on Apr. 28, 2010, now Pat. No. 8,513,605.

(51) Int. Cl.
*G01J 5/20* (2006.01)
*H01L 37/00* (2006.01)
(Continued)

(52) U.S. Cl.
CPC ............ *H01L 37/00* (2013.01); *G01N 21/3581* (2013.01); *G01J 1/02* (2013.01); *G01J 1/0204* (2013.01); *G01J 1/04* (2013.01); *G01J 1/0411* (2013.01); *G01J 1/0429* (2013.01); *G01J 1/0488* (2013.01); *G01J 4/04* (2013.01); *G01J 5/02* (2013.01); *G01J 5/0215* (2013.01); *G01J 5/023* (2013.01); *G01J 5/024* (2013.01); *G01J 5/08* (2013.01); *G01J 5/0806* (2013.01); *G01J 5/0825* (2013.01); *G01J 5/0862* (2013.01); *G01J 5/20* (2013.01); *H01L 27/14621* (2013.01);
(Continued)

(58) Field of Classification Search
CPC .............................. G01J 5/20; G01N 21/3581
USPC ........................................... 250/338.4, 338.1
See application file for complete search history.

(56) References Cited

U.S. PATENT DOCUMENTS 5,286,976 A   2/1994   Cole
5,808,350 A   9/1998   Jack et al.
(Continued)

FOREIGN PATENT DOCUMENTS

EP      0680101 A1    5/1995
JP      07-331430    12/1995
(Continued)

OTHER PUBLICATIONS

Lewis et al., Thin Film Thermochromic Materials for Non-Linear Optical Devices, 1995, Mat. Res. Soc. Symp. Proc., vol. 374, pp. 105-116.*
(Continued)

*Primary Examiner* — Christine Sung
(74) *Attorney, Agent, or Firm* — Egan, Peterman & Enders LLP

(57) ABSTRACT

A thermal absorption structure of a radiation thermal detector element may include an optically transitioning material configured such that optical conductivity of the thermal absorption structure is temperature sensitive and such that the detector element absorbs radiation less efficiently as its temperature increases, thus reducing its ultimate maximum temperature.

14 Claims, 34 Drawing Sheets

(51) Int. Cl.
 G01J 1/02 (2006.01)
 G01J 1/04 (2006.01)
 G01J 4/04 (2006.01)
 G01J 5/02 (2006.01)
 G01J 5/08 (2006.01)
 G01N 21/3581 (2014.01)
 H01L 27/146 (2006.01)

(52) U.S. Cl.
 CPC ..... H01L27/14627 (2013.01); *H01L 27/14669* (2013.01); *H01L 27/14683* (2013.01)

(56) References Cited

U.S. PATENT DOCUMENTS

| | | | |
|---|---|---|---|
| 5,900,799 | A | 5/1999 | Morris |
| 5,990,481 | A | 11/1999 | Beratan |
| 6,121,618 | A * | 9/2000 | Morris .................. 250/352 |
| 6,201,243 | B1 | 3/2001 | Jerominek |
| 6,229,144 | B1 | 5/2001 | Ouvrier-Buffet et al. |
| 6,489,613 | B1 | 12/2002 | Mori et al. |
| 6,690,014 | B1 | 2/2004 | Gooch et al. |
| 6,777,681 | B1 | 8/2004 | Schimert et al. |
| 7,208,736 | B2 | 4/2007 | Watanabe |
| 7,459,686 | B2 | 12/2008 | Syllaios et al. |
| 7,462,831 | B2 | 12/2008 | Gooch et al. |
| 7,494,232 | B2 | 2/2009 | Wu et al. |
| 8,227,755 | B2 | 7/2012 | Fagan, III et al. |
| 2004/0188617 | A1 | 9/2004 | Devitt et al. |
| 2007/0170359 | A1 | 7/2007 | Syllaios et al. |
| 2007/0215805 | A1 | 9/2007 | Boie et al. |
| 2008/0048121 | A1 | 2/2008 | Hinnrichs |
| 2008/0265164 | A1 | 10/2008 | Ouvrier-Buffet et al. |
| 2009/0236525 | A1 | 9/2009 | Mitra et al. |
| 2010/0025581 | A1 | 2/2010 | Aksyuk et al. |
| 2010/0187580 | A1 | 7/2010 | Yang |
| 2010/0194901 | A1 | 8/2010 | Van Hoorebeke et al. |
| 2011/0141286 | A1 | 6/2011 | Vilain |
| 2011/0233404 | A1 | 9/2011 | Sonstroem |
| 2011/0266443 | A1 | 11/2011 | Schimert et al. |
| 2011/0266444 | A1 | 11/2011 | Hanson |
| 2011/0266445 | A1 | 11/2011 | Beratan |

FOREIGN PATENT DOCUMENTS

| | | |
|---|---|---|
| JP | 08-005452 | 1/1996 |
| JP | 2000-186958 | 7/2000 |
| JP | 2001-324382 | 11/2001 |
| JP | 2009-106896 | 4/2003 |
| KR | 10-2000-0007482 | 2/2000 |
| KR | 10-0509443 | 8/2005 |
| KR | 10-07-0116703 | 12/2007 |
| WO | WO98/54554 | 12/1998 |
| WO | WO2010/040945 A1 | 4/2010 |

OTHER PUBLICATIONS

Wikipedia, "Vanadium (IV) Oxide", Printed From Internet Apr. 12, 2010, 2 pgs.
Manning et al., "Tungsten Doped Vanadium Oxide Thin Films by Atmospheric Pressure Chemical Vapour Deposition", Printed from Internet on Apr. 12, 2010, 1 pg.
Search Report, PCT/US2011/000660, Nov. 16, 2011, 3 pgs.
Fagan et al. "Pixel-Level Optically Transitioning Filter Elements for Detector Devices", U.S. Appl. No. 12/799,629, filed Apr. 28, 2010, Notice of Allowance, Mailed Apr. 12, 2012, 8 pgs.
Schimert et al. "Pixel-Level Optically Elements for Uncooled Infrared Detector Devices", U.S. Appl. No. 12/799,626, filed Apr. 28, 2010, Office Action, Mailed Jul. 31, 2012, 13 pgs.
Schimert et al. "Pixel-Level Optically Elements for Uncooled Infrared Detector Devices", U.S. Appl. No. 12/799,626, filed Apr. 28, 2010, Response to Office Action, Nov. 30, 2012, 17 pgs.
Schimert et al. "Pixel-Level Optically Elements for Uncooled Infrared Detector Devices", U.S. Appl. No. 12/799,626, filed Apr. 28, 2010, Final Office Action, May 14, 2013, 9 pgs.
Beratan, "Optically Transitioning Thermal Detector Services", U.S. Appl. No. 12/799,628, filed Apr. 28, 2010, Office Action, Aug. 1, 2012, 16 pgs.
Beratan, "Optically Transitioning Thermal Detector Services", U.S. Appl. No. 12/799,628, filed Apr. 28, 2010, Response to Office Action, Nov. 1, 2012, 20 pgs.
Beratan, "Optically Transitioning Thermal Detector Services", U.S. Appl. No. 12/799,628, filed Apr. 28, 2010, Final Office Action, Jan. 29, 2013, 21 pgs.
Beratan, "Optically Transitioning Thermal Detector Services", U.S. Appl. No. 12/799,628, filed Apr. 28, 2010, Response to Final Office Action, Mar. 29, 2013, 16 pgs.
Schimert et al. "Pixel-Level Optically Elements for Uncooled Infrared Detector Devices", U.S. Appl. No. 12/799,626, filed Apr. 28, 2010, Response to Final Office Action, Aug. 14, 2013, 16 pgs.

* cited by examiner

Moderate Temperature

High Temperature

OPTICALLY TRANSITIONING THERMAL DETECTOR STRUCTURES

RELATED APPLICATIONS

This application is a continuation of pending U.S. patent application Ser. No. 12/799,628, filed on Apr. 28, 2010 and entitled "Optically Transitioning Thermal Detector Structures", which is incorporated herein by reference in its entirety for all purposes.

The present application is related in subject matter to concurrently filed patent application Ser. No. 12/799,626, entitled "PIXEL-LEVEL OPTICAL ELEMENTS FOR UNCOOLED INFRARED DETECTOR DEVICES" by Schimert et al., and concurrently filed patent application Ser. No. 12/799,629, now U.S. Pat. No. 8,227,755, entitled "PIXEL-LEVEL OPTICALLY TRANSITIONING FILTER ELEMENTS FOR DETECTOR DEVICES" by Fagan III et al., which are each incorporated herein by reference in their entirety.

FIELD OF THE INVENTION

This invention relates generally to radiation detector devices, and more particularly to optically transitioning thermal detector devices such as microbolometer pixel membrane structures for uncooled infrared detector devices.

BACKGROUND OF THE INVENTION

Infrared (IR) detectors are often utilized to detect fires, overheating machinery, planes, vehicles, people, and any other objects that emit thermal radiation. Infrared detectors are unaffected by ambient light conditions or particulate matter in the air such as smoke or fog. Thus, infrared detectors have potential use in night vision and when poor vision conditions exist, such as when normal vision is obscured by smoke or fog. IR detectors are also used in non-imaging applications such as radiometers, gas detectors, and other IR sensors.

A variety of uncooled infrared detector types have been developed in the past. Many include a focal plane array (FPA) that includes a substrate with a plurality of detector elements that each correspond to a respective pixel. The substrate includes integrated circuitry which is electrically coupled to other components of the detector elements, and which is commonly known as a read out integrated circuit (ROIC).

Infrared detectors generally operate by detecting the differences in thermal radiance of various objects in a scene. That difference is converted into an electrical signal which is then processed. Microbolometers are infrared radiation detector elements that are fabricated on a substrate material using traditional integrated circuit fabrication techniques. Microbolometer detector arrays consist of thin, low thermal mass, thermally isolated, temperature-dependent resistive membrane pixel structures. The microbolometer membrane pixel structures are suspended over silicon ROIC wafers by long thermal isolation legs in a resonant absorbing quarter-wave cavity design.

FIG. 1 illustrates a conventional prior art uncooled infrared detector element 100 with a microbolometer pixel membrane structure 112 that includes thin (1000 A to 4000 A) thermally-electrically active layer of thermally absorbing membrane material of a resistive material like amorphous silicon (a-Si); amorphous silicon geranium (a-SiGe); or vanadium oxide together with an infrared absorbing thin metal absorber layer like Ti, TiAl; TiN; or Ni and supporting silicon nitride, silicon oxide; or silicon oxynitride. The microbolometer pixel membrane structure 112 is suspended approximately 2 microns above silicon semiconductor substrate 110 by long thermal isolation legs 116 that are electrically connected to the ROIC of the semiconductor substrate 110 by metal interconnects 108 (typically TiW or Aluminum) via aluminum input pads 114. Disposed on the surface of the supporting substrate 110 and ROIC is a metal reflector 118 (typically Aluminum) to form a resonant cavity structure to enhance infrared absorptance in the membrane of the suspended microbolometer pixel structure 112. For infrared applications, pixel size typically ranges from 12 um×12 um up to 100 um×100 um.

Primary factors affecting response time and sensitivity of microbolometers are thermal mass and thermal isolation. Microbolometer response time is the time necessary for a detector element to absorb sufficient infrared radiation to alter an electrical property, such as resistance, of the detector element and to dissipate the heat resulting from the absorption of the infrared radiation. Microbolometer sensitivity is determined by the amount of infrared radiation required to cause a sufficient change in an electrical property of the microbolometer detector element. Microbolometer response time is inversely proportional to both thermal mass and thermal isolation. Thus, as thermal mass increases, response time becomes slower since more time is needed to sufficiently heat the additional thermal mass in order to obtain a measurable change in an electrical property of the microbolometer detector element. Therefore, it is generally desirable to make microbolometer pixels that are low in mass in order to achieve a short thermal time constant, while at the same time maximizing absorption of radiation.

As shown in FIG. 1, material has been removed from the membrane material of microbolometer pixel membrane structure 112 in a square or rectangular grid pattern to reduce microbolometer pixel mass and to shorten thermal time constant while maintaining good radiation absorption characteristics. In FIG. 1, suspended microbolometer detector pixel structure 112 includes conductive element portions 106 that are oriented both parallel and orthogonal to the path of current flow between electrical contacts 102 and 104. As illustrated, openings in the form of square holes 111 are defined by material removed between the electrical contacts 106 to reduce the microbolometer pixel mass. The holes are typically dimensioned to be small compared to the radiation wavelength of interest. Microbolometer pixels fabricated with this structure are sometimes called diffractive resonant cavities (DRCs).

In the past, detector material optimization has been employed to limit or enhance absorption within specific bands. Polarizers and spectral filters have been separately fabricated and then mounted at a relatively large distance (i.e., a distance greater than the pixel size) over a focal plane array of uncooled infrared detector elements in a manner that causes radiation cross talk problems. Monolithically-fabricated spectral and polarizer filters have been provided for non-thermal photon infrared detector cells, such as mercury-cadmium-telluride (HgCdTe) and indium-antimonide (InSb) infrared photon detector cells. Attempts have been made to physically align and mount previously and separately-fabricated microlens arrays at a distance of about 10 microns or greater over and above the upper surface of thermal and non-thermal infrared detector focal plane arrays, with individual microlenses of the microlens array being aligned to individual detector elements of the focal plane array at a distance of about 10 microns or greater over and above the upper surface of the focal plane array. Such previously and separately-fabricated microlens arrays are fabricated separately and apart from the infrared detector focal plane arrays themselves for later assembly thereto. Other examples of previously employed detector filtering techniques include neutral density filters, shutters or filters activated by remote detectors, lens material optimization to limit or enhance transmission of specific bands, and spectral filtering structures built into detector packaging.

In other cases, window glass has been coated with thermochromic vanadium oxide film that darkens with increased temperature to block infrared radiation in response to higher levels of infrared energy. Certain welding hoods have also been manufactured having a transparent viewing window that includes a ferroelectric material and an integral detection apparatus that detects light or radiation produced by a welding arc. These welding hoods are designed to respond to the presence of a detected welding arc by applying an electric field to the ferroelectric material of the viewing window to cause darkening of the viewing window in a manner that protects the eyes of the welding operator wearing the hood. Past attempts to provide solar immunity to detector elements have included altering materials of the detector element to broaden its range of temperature use, reducing optical speed, and mechanically closing a shutter to block radiation. Most past attempts to provide solar immunity to cameras have involved incorporation of mechanical devices that increase system complexity and cost, and which may prevent the camera from viewing the scene.

SUMMARY OF THE INVENTION

Disclosed herein are apparatus and methods in which a thermal absorption structure of a thermal detector element may include an optically transitioning material configured, for example, such that the thermal absorption capability of the detector element varies with temperature of the detector element. Examples of such thermal detector elements include any radiation detector element that utilizes a thermal absorption structure to sense radiation falling incident thereon by measuring at least one property having a value that changes with temperature. Examples include, but are not limited to, thermal detector elements that sense radiation by measuring changes in one or more properties of electrical resistance, electrical capacitance, electrical voltage, electrical current, electromotive force, etc. Specific examples of such thermal detector elements include, but are not limited to, thermocouple detectors, ferroelectric detectors, microbolometer detectors, etc.

A thermal absorption structure of a thermal detector element may include a filter layer composed of one or more optically transitioning materials having optical properties that change with temperature, e.g., that change from optically transmissive to optically reflective or from optically reflective to optically transmissive with increasing temperature. Examples of such optically transitioning materials include, but are not limited to, thermochromic or phase shifting/phase transitioning materials that act to selectively transmit radiation depending on temperature, for example, a semi-transparent material that is thermochromic such that optical transmission of the semi-transparent material is temperature sensitive. For example, in one embodiment an optically transitioning material may undergo a semiconducting-to-metallic phase transition with increasing temperature, e.g., from a transparent or at least partially transparent semiconductor state to a reflective or at least partially reflective metallic state. Particular examples of optically transitioning materials include, but are not limited to, thermochromic or phase transitioning compositions of germanium-antimony-tellurium (GST or $Ge_xS$-$b_yTe_z$), vanadium oxide (VO, $VO_2$, $V_nO_{2n-1}$ such as $V_2O_3$), tungsten-doped vanadium oxide (W:$VO_x$ such as W:$VO_2$, and stoichiometric variants), niobium oxide, tantalum oxide, $Ti_2O_3$, $Fe_3O_4$, $Mo_9O_{26}$, etc. Further, as described elsewhere herein, composition of such materials may be varied (e.g., by doping with other materials such as tungsten, aluminum and/or manganese) to tailor the optical transition (e.g., phase transition) characteristics of the material as a function of temperature.

For example, in one exemplary embodiment a microbolometer pixel membrane structure of a thermal detector element (e.g., for detecting infrared radiation, millimeter wave radiation, etc.) may include an optically transitioning material, for example, a semi-transparent material that is thermochromic (e.g., provided as a thermochromic layer of the membrane itself) such that optical transmission of the semi-transparent material is temperature sensitive. Such an optically transitioning microbolometer pixel membrane structure may be employed for individual detector elements (e.g., of a focal plane array of an uncooled infrared detector or any other type of radiation detector that includes a microbolometer membrane structure). In such an embodiment, the microbolometer pixel membrane structure of each detector element may be configured to absorb radiation less efficiently as its temperature increases, thus reducing its ultimate maximum temperature. Such an optically transitioning microbolometer pixel membrane structure configuration may be implemented to enable a detector element to view a scene that includes undesired radiation wavebands (e.g., such as direct sunlight), while at the same time protecting the detector element from temporary or permanent damage. The microbolometer pixel membrane structure may be disposed to absorb radiation over a silicon ROIC wafer that has a metal reflector on the ROIC surface to form a tuned cavity, with distance from the membrane to the mirrored reflector and sheet resistance of the semi-transparent conductive material of the membrane being two factors affecting cavity absorption efficiency.

Examples of optically transitioning materials that may be employed as part of an optically transitioning microbolometer pixel membrane structure or other type of thermal detector element component include, but are not limited to, thermochromic or phase shifting/phase transitioning materials (e.g., thermochromic or phase transitioning compositions of germanium-antimony-tellurium (GST or $Ge_xSb_yTe_z$), vanadium oxide (VO, $VO_2$, $V_nO_{2n-1}$ such as $V_2O_3$), tungsten-doped vanadium oxide (W:$VO_x$ such as W:$VO_2$, and stoichiometric variants), niobium oxide, tantalum oxide, $Ti_2O_3$, $Fe_3O_4$, $Mo_9O_{26}$, etc.) that act to selectively transmit and/or absorb radiation depending on temperature. As described elsewhere herein, composition of such materials may be varied (e.g., by doping with other materials such as tungsten, aluminum and/or manganese) to tailor the optical transition (e.g., phase transition) characteristics of the material as a function of temperature.

In another exemplary embodiment, uncooled infrared detectors and focal plane arrays may be provided in which an optically transitioning filter element may be suspended over a corresponding microbolometer pixel membrane structure of an infrared detector element, i.e., a separate suspended optically transitioning filter element may be provided that corresponds to each of multiple detector elements of a focal plane array (FPA) in a one-to-one relationship (i.e., a separate optical element provided for each respective detector element of the FPA such that each optical element is suspended over and above radiation detection circuitry of the respective detector element and is not suspended over and above the radiation detection circuitry of other adjacent detector elements, and such that each optical element only filters or focuses radiation destined for the underlying radiation detection circuitry of the respective radiation detector element and not any other radiation detector elements of the FPA). An optically transitioning filter element may be structurally attached by an electrically and/or thermally insulating interconnect to existing metal interconnects. In this way, the installation of the optically transitioning filter element substantially does not impact the thermal mass or degrade the thermal time constant of the microbolometer pixel structure and does not require any additional device real estate area beyond the area originally consumed by the microbolometer pixel structure interconnects so as to preserve the original infrared absorbing fill factor of the microbolometer pixel structure.

Pixel-level optically transitioning filter elements may be employed to achieve real time filtering of radiation in an active manner without adding significant optical crosstalk effects, without degradation (i.e., increasing) of the detector thermal time constant, and/or in a manner that allows for thermal response tuning independent of the detector pixel. Such active pixel-level filtering may be implemented by providing a multi-level structure that includes a thermally and electrically isolated optically transitioning filter element that is suspended over a microbolometer pixel membrane structure of a corresponding infrared detector element, i.e., in a one-to-one relationship (i.e., one optical element provided for each underlying detector element). Such an embodiment may be advantageously implemented to provide optically transitioning pixel-level filter elements to enable one or more features such as spectral infrared radiation detection and/or selective radiation immunity.

Optically transitioning filter elements disclosed herein may be controlled by the properties of a selected optically transitioning material or materials, i.e., the optically transitioning material transmits radiation at temperatures below the transition temperature of the material while it reflects at one or more specific radiation wavelength bands at temperatures above the transition temperature of the material. Since the thermal response is a result of the thermal flux of the radiation and the thermal isolation of the filter element (e.g., including optically transitioning filter or combination of optically transitioning and passive filters), it therefore can be controlled with thermal isolation structures/forms. In this regard, an optically transitioning filter element may be suspended by one or more low thermal conductivity or thermally insulating support interconnect/s and thermal isolation structures/forms in a manner such that the optically transitioning filter element substantially does not affect the thermal time constant of the underlying microbolometer pixel structure. Furthermore, the thermal isolation structure/forms may be implemented to allow for the tuning of the thermal response of the optically transitioning filter element to the flux of the radiation in a manner that is independent of the response of the underlying microbolometer pixel structure to the radiation flux.

Examples of applications for a detector element that includes an optically transitioning filter element include, but are not limited to, partially or fully shielding underlying radiation detector circuitry (e.g., infrared microbolometer pixel membrane, charge coupled device (CCD) detector pixel, millimeter wave detector pixel, CMOS detector pixel, etc.) from direct solar radiation or other undesired radiation wavebands. Such exposure may occur, for example, when a detector device including the detector element is inadvertently pointed at the sun, and may result in permanent damage to the detector element or formation of a latent image that may remain on the detector element for an extended period of time.

In another exemplary embodiment, one or more individual detector elements may be provided with optically transitioning filter elements that partially or fully shield underlying radiation detector circuitry from different levels of radiation than other detector elements of the same focal plane array. For example, a first optically transitioning filter element may be provided to shield underlying radiation detector circuitry of a first detector element from a first level of infrared energy (e.g., energy having less than or equal to about 5 microns wavelength) while a second optically transitioning filter element may be provided to shield underlying radiation detector circuitry of an adjacent second detector element from a second level of infrared energy (e.g., energy having less than or equal to about 7 microns wavelength).

To prevent such damage, individual detector elements (e.g., of a focal plane array) may be provided in one exemplary embodiment with optically transitioning filter elements that are composed of an optically transitioning material that remains substantially transmissive to desired radiation wavebands (e.g., indirect reflected sunlight, artificial room lighting, etc.), but that becomes substantially non-transmissive or opaque to undesired radiation wavebands (e.g., direct sunlight, electrical arc radiation, etc.). In such an embodiment, the optically transitioning filter may be configured in a manner that it sufficiently dissipates heat when exposed to desired radiation wavebands at normal operating temperature such that the optically transitioning material remains below its optical transition (e.g., phase transition) temperature and in a corresponding substantially transmissive state, but also in a manner such that exposure to radiation of an undesired bandwidth generates sufficient heat that cannot be dissipated rapidly enough to prevent the temperature of the phase transitioning material from increasing above its optical transition (e.g., phase transition) temperature and becoming at least partially non-transmissive or opaque to the undesired radiation. In this way, the optically transitioning filter acts to transmit desired radiation to the underlying detector circuitry, but automatically shields the underlying detector circuitry from the undesired radiation.

The disclosed optically transitioning filter elements may be optionally combined in one exemplary embodiment with passive optical elements disclosed elsewhere herein (e.g., spectral filters, polarizing filters, microlens, etc.) to enable other features such as polarimetric infrared detection. Specific examples of applications for which the disclosed optically transitioning pixel-level filtering may be employed include, but are not limited to, providing solar immunity for infrared detectors, providing temperature dependent spectral radiation selectivity, scientific applications (e.g., study of astronomical light sources, study of interstellar manner, etc.).

In one exemplary embodiment, a multi-layer structure may be provided that includes an optically transitioning filter element layer that is optionally combined with other layers of optically transitioning, passive or combination passive/optically-transitioning optical elements that each filter different wavelengths. Whether provided alone or in combination with other suspended optical elements, a multilayer optically transitioning structure (or other type of suspended optical element disclosed herein) may be provided that is thermally isolated and positioned in close proximity (e.g., less than about 10 microns in one embodiment, less than about 10 microns and greater than or equal to about 1 micron in another embodiment, from about 1 micron to about 10 microns in another embodiment, less than or equal to about 5 microns in another embodiment, from about 1 micron to about 5 microns in another embodiment; about 2 microns in another embodiment, less than or equal to about 2 microns in another embodiment; and from 1 micron to about 2 microns in another embodiment) to an underlying microbolometer pixel structure or other type of detector circuitry to reduce cross talk between adjacent pixels of a FPA.

In another exemplary embodiment, an optically transitioning filter element may be monolithically fabricated with an underlying detector pixel, or may be separately fabricated and then attached or otherwise assembled to a detector element. However, in one exemplary embodiment, pixel-level optically transitioning filter elements may be "monolithically fabricated" in-situ, i.e., the layers or other structural elements of an optically transitioning filter element is fabricated in place over the microbolometer pixel membrane structure of a corresponding infrared detector element, rather than being fabricated separately from other components of the infrared detector element and then assembled to the infrared detector element.

In one exemplary embodiment, a monolithic optically transitioning filter element may be fabricated using modern photolithographic techniques so that precise registration and alignment of the optically transitioning filter element over a bolometer pixel is achieved. In another embodiment, the suspended optically transitioning filter element may be disposed in sufficiently close proximity (e.g., about 2 microns in one embodiment, less than or equal to about 2 microns in another embodiment) to the underlying detector circuitry (e.g., microbolometer pixel structure) to minimize or substantially eliminate cross talk between adjacent pixels of a FPA. However, a suspended optically transitioning filter element may be disposed at any other greater or lesser distance relative to a microbolometer pixel membrane structure, e.g., as may be appropriate to optical focusing requirements for a given application.

Among the infrared applications for which the disclosed radiation detectors and focal plane arrays may be employed include, but are not limited to, spectroscopic polarimetric infrared imaging applications such as identification of man-made objects (e.g., vehicles, armor, etc.) in a cluttered background of natural objects such as trees, vegetation or concealment materials, identification of non-polarizing layers on polarizing surfaces (e.g., ice on highways, ice on aircraft wings, etc.), scientific applications (e.g., study of astronomical light sources, interstellar matter, etc.), etc.

In one respect, disclosed herein is a thermal detector element including an optically transitioning thermal absorption structure, the thermal detector element being configured to sense radiation falling incident thereon by measuring at least one property of the thermal absorption structure that changes value with temperature, the thermal absorption structure being provided with one or more components that include at least one optically transitioning material.

In another respect, disclosed herein is a focal plane array assembly, including a plurality of individual thermal detector elements arranged as an array, at least a portion of the plurality of individual thermal detector elements including an optically transitioning thermal absorption structure and being configured to sense radiation falling incident thereon by measuring at least one property of the thermal absorption structure that changes value with temperature, the thermal absorption structure being provided with one or more components that include at least one optically transitioning material. A wafer-level packaged focal plane array assembly is also disclosed that includes: a device wafer that includes the focal plane array assembly; and a lid wafer, the lid wafer being at least partially transmissive of the incident radiation and being assembled to the device wafer such that the lid wafer allows the incident radiation to reach the focal plane array assembly through the lid wafer.

In another respect, disclosed herein is a method of making a focal plane array assembly, including forming a plurality of individual thermal detector elements arranged as an array, each of the plurality of individual detector elements including an optically transitioning thermal absorption structure and being configured to sense radiation falling incident thereon by measuring at least one property of the thermal absorption structure that changes value with temperature, the thermal absorption structure being provided with one or more components that include at least one optically transitioning material.

DESCRIPTION OF ILLUSTRATIVE EMBODIMENTS

Figure 1:
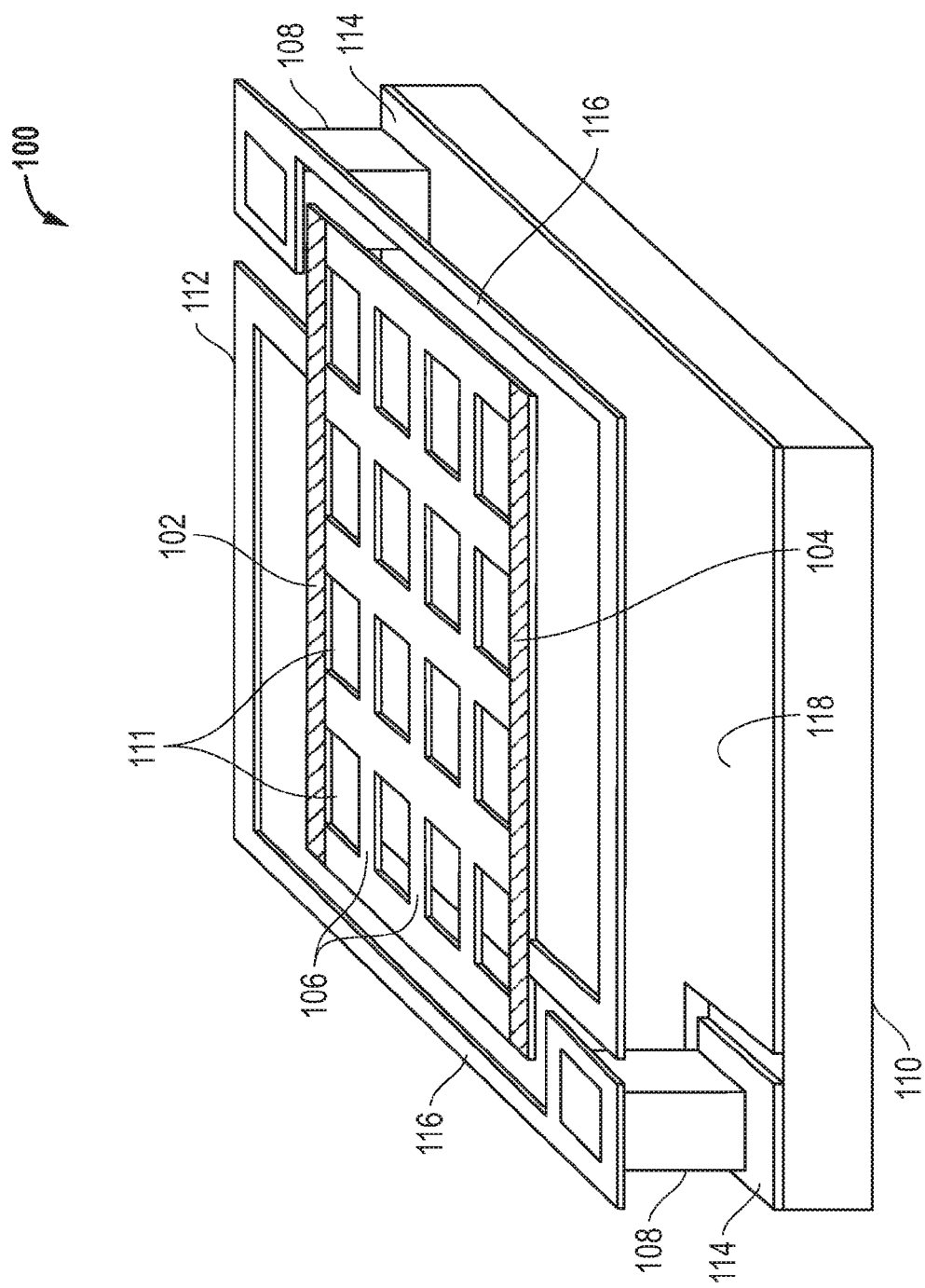
FIG. 1 illustrates a perspective view of a conventional prior art uncooled infrared detector element.
Figure 2:
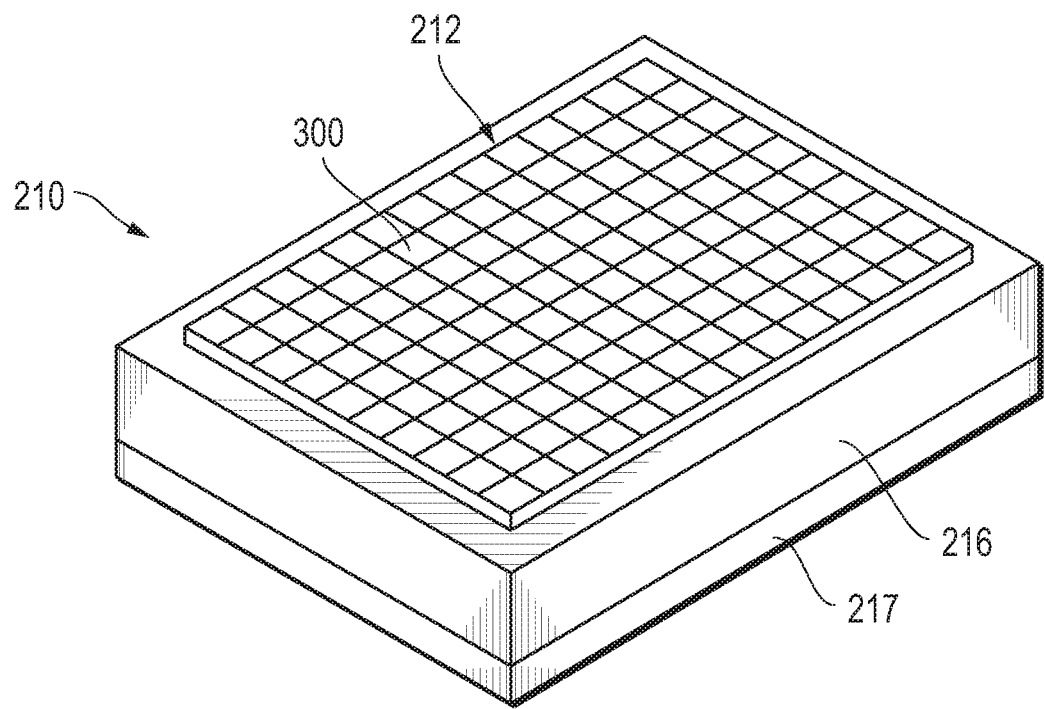
FIG. 2 illustrates a perspective view of an uncooled infrared detector according to one exemplary embodiment of the disclosed apparatus and methods.

FIG. 2 is a diagrammatic perspective view of an uncooled IR detector 210 which may be configured according to one exemplary embodiment to sense thermal energy and output electrical signals representative of a two-dimensional image of that sensed thermal energy. In this embodiment, the IR detector 210 includes a focal plane array (FPA) 212 disposed on a substrate 216. The substrate 216 includes read out integrated circuitry (ROIC) and FPA 212 may be uncooled. The ROIC may be configured to integrate thermally induced electrical signals from the suspended microbolometer detector pixel element of each IR detector element 300 in the focal plane array 212. Each suspended microbolometer detector pixel element may include a suspended monolithic filter as will be further described herein. As further shown in FIG. 2, an optional thermal element 217 (e.g., active heat sink) may be provided on the side of the substrate 216 opposite from the focal plane array 212, in order to serve as a form of controlled heat sink which may be used, for example, to maintain the operating temperature of integrated circuit substrate 216 within a temperature range which may be predefined. However, it will be understood that thermal element 217 does not have to be present, and that no form of temperature stabilization is required.

In one exemplary embodiment, the focal plane array 212 may include a plurality of IR detector elements 300 that are arranged in a two-dimensional array, with each detector element 300 corresponding to a respective pixel in each image detected by the IR detector 210. In one exemplary configuration, focal plane array 212 may include 76,800 IR detector elements 300, which are arranged in a 320 by 240 array, although a focal plane array may be of any other size depending as needed or desired for a particular application, e.g., ranging in size from greater than or equal to an 80×60 array up to megapixel-sized arrays. For clarity, however, FIG. 2 diagrammatically depicts only about 140 detector elements. It will be recognized that the total number of detector elements 300 in the focal plane array 212 may be larger or smaller. FIG. 2 shows the detector elements 300 arranged in a two-dimensional array. Examples of two-dimensional array configurations include, but are not limited to, arrays having a shape that is rectangular, octagonal, hexagonal, circular, etc. It will be understood that detector elements may alternatively be arranged in a one-dimensional (e.g., straight or curved line of mono-pixels) array, or may be provided at arbitrary locations that do not conform to a specific pattern.

In one embodiment, a focal plane array 212 may be formed and placed in a single vacuum package to form a vacuum-packaged pixel array structure for thermal imaging. In this embodiment, the IR detector elements 210 are discrete devices detecting thermal energy in a specific portion of a target (scene) area. For example, IR detector elements 210 may be formed on a device wafer and then sealingly assembled with a lid wafer that is at least partially transmissive of infrared radiation (i.e., having at least some infrared radiation transmission characteristics) in the presence of a vacuum to sealingly contain a vacuum therebetween, although non-vacuum packaged device wafer/lid wafer package combinations are also possible, as are non-IR FPAs and transmissive lids therefor.

Examples of technology (e.g., including materials and/or configurations for detectors, focal plane arrays, microbolometer membranes, and packaging thereof) with which the various disclosed embodiments disclosed herein may be implemented may be found in U.S. Pat. No. 7,459,686; U.S. Pat. No. 6,777,681; U.S. Pat. No. 6,690,014; and U.S. patent application Ser. No. 12/799,627, entitled "PIXEL STRUCTURE FOR MICROBOLOMETER DETECTOR" by Hanson which is concurrently filed on the same day as the present application, each of the foregoing being incorporated herein by reference in its entirety. Besides IR detector elements 300, it will be understood that the configuration of focal plane array 212 may alternatively or additionally include a plurality of IR detector elements 1200, 1900, 2400 and/or 2500 (which are described further herein) that are arranged in a two-dimensional array in a similar manner as IR detector elements 300.

Figure 3:
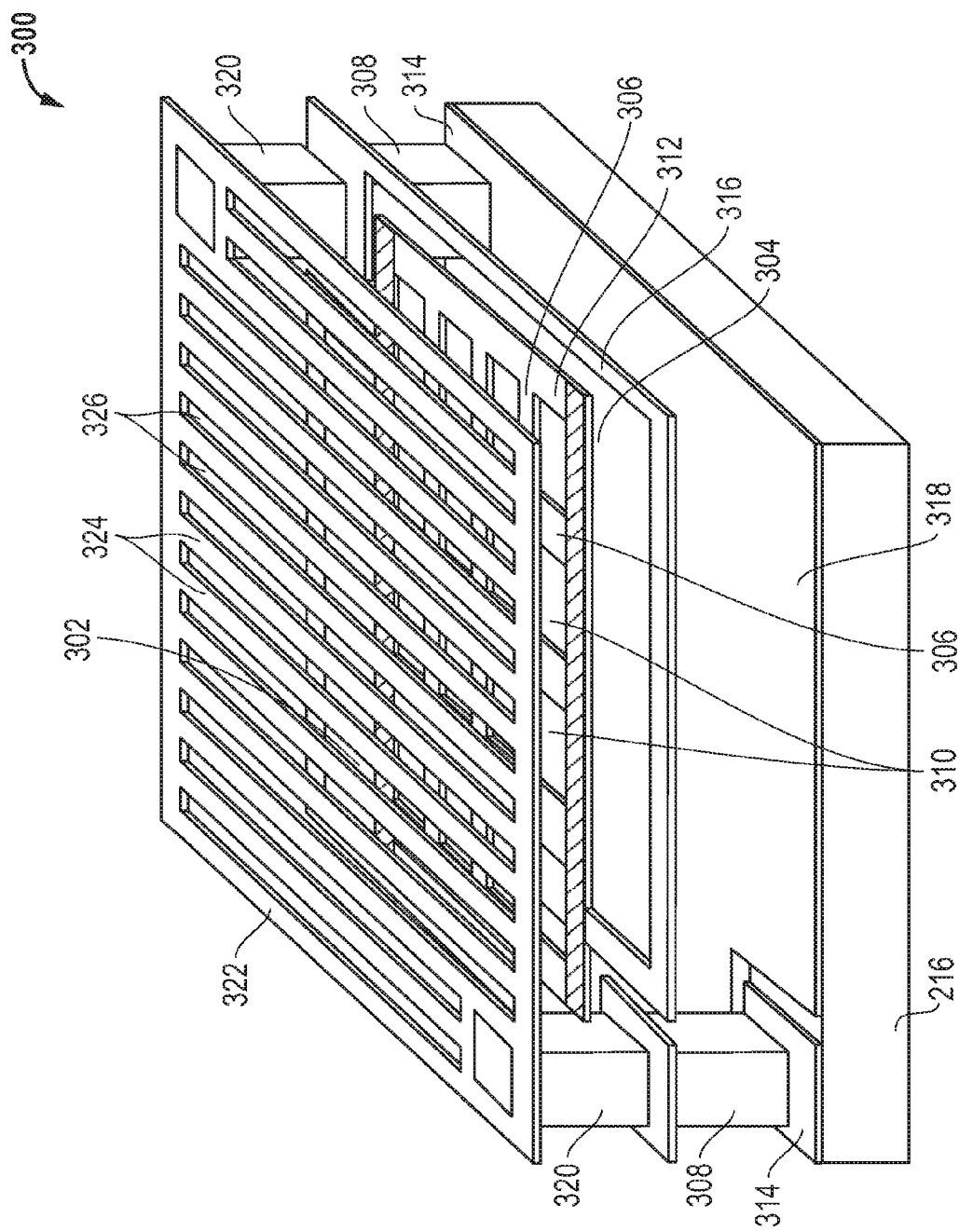
FIG. 3 illustrates a perspective view of an uncooled infrared detector element according to one exemplary embodiment of the disclosed apparatus and methods.

FIG. 3 illustrates one exemplary embodiment of an uncooled infrared detector element 300 that includes an optical element in the form of a monolithic polarizer filter 322 suspended at a distance of from about 1 micron to about 3 microns over and above a microbolometer pixel membrane structure 312 by two optical element support interconnects 320 that extend down and are substantially aligned to and supported by the top of thermally and electrically conductive interconnects 308 (e.g., titanium, tungsten, titanium-tungsten (TiW), aluminum, or any other suitably thermally and electrically conductive material) of microbolometer pixel structure 312). In one exemplary embodiment, conductive interconnects 308 may be configured in hollow tubular form (e.g., cylindrical, square, conical, etc.), with sidewalls of about 1750 angstroms thick, although solid interconnects or interconnects having greater or lesser wall thicknesses may be alternately employed. Conductive interconnects 308 are in turn coupled to readout integrated circuitry of the supporting semiconductor substrate 216 by electrically conductive input pads 314 which may be made of aluminum or other suitably electrically conductive material. Conductive interconnects 308 are configured in one embodiment to supply electrical connection between microbolometer pixel membrane structure 312 and circuitry of substrate 216.

As shown in FIG. 3, microbolometer pixel membrane structure 312 includes a thin absorber layer (e.g., from about 1000 Angstroms to about 4000 Angstroms thick) of thermally absorbing resistive membrane material (e.g., such as amorphous silicon (a-Si), amorphous silicon geranium (a-SiGe), Vanadium Oxide (VOx), etc.) together with an infrared absorbing thin metal thermally-electrically active layer (e.g., titanium (Ti), titanium aluminum (TiAl), titanium nitride (TiN), nickel, etc.), and supporting material (e.g., silicon nitride, silicon oxide, silicon oxynitride, etc.). Further detail on one exemplary embodiment of components of microbolometer pixel membrane structure 312 may be found in FIGS. 19-22 herein. In one exemplary embodiment, the microbolometer pixel membrane structure 312 may be suspended about 2 microns above silicon semiconductor substrate 216 by relatively long thermal isolation legs 316 that are electrically connected to the ROIC of the semiconductor substrate 216 by the metal interconnects 308 via conductive input pads 314, although a microbolometer pixel membrane structure 312 may be suspended greater than or less than about 2 microns above a substrate (e.g., such as above silicon semiconductor substrate 216 or above a reflector layer disposed on a silicon semiconductor substrate) in other embodiments. Conductive interconnects 308 are electrically coupled to pass current across the thermally-electrically active layer of microbolometer pixel membrane structure 312 to allow ROIC of the semiconductor substrate 216 to measure changing electrical properties of the thermally-electrically active layer as varying levels of infrared radiation is absorbed by microbolometer pixel membrane structure 312.

A reflector 318 (e.g., reflective metal such as aluminum, etc. or other suitably reflective non-metal material) for reflecting IR radiation may be optionally disposed as shown on the surface of the supporting substrate 216 and ROIC to form a resonant cavity structure to enhance infrared absorptance in the membrane of the suspended microbolometer pixel structure 312. In one exemplary embodiment, pixel geometry may be square-shaped and the pixel area may range from about 12 um×12 um to about 100 um×100 um, although pixel shapes other than square and/or pixel sizes smaller than 12 um×12 um or greater than 100 um×100 um may be employed in other embodiments. As shown, microbolometer pixel membrane structures 312 has been implemented in a diffractive resonant cavity (DRC) configuration with material being removed from the membrane material of suspended microbolometer pixel membrane structure 312 in a square or rectangular grid pattern to form openings 310 defined by conductive element portions 306 that are oriented both parallel and orthogonal to the path of current flow between the electrical contacts 302 and 304. Openings 310 may be dimensioned to be small compared to the radiation wavelength of interest. It will be understood that in other embodiments, openings may be defined in a microbolometer pixel membrane structure using pattern shapes other than square or rectangular.

Examples of IR detectors and focal plane array technology with which the disclosed monolithic optical elements may be implemented in a suspended configuration relative to a microbolometer membrane structure may be found in U.S. Pat. No. 7,459,686; U.S. Pat. No. 6,777,681; and U.S. Pat. No. 6,690,014, and U.S. patent application Ser. No. 12/799, 627, entitled "PIXEL STRUCTURE FOR MICROBOLOMETER DETECTOR" by Hanson which is concurrently filed on the same day as the present application, each of the foregoing being incorporated herein by reference in its entirety.

Still referring to FIG. 3, monolithic polarizer filter 322 may be of any material of a rigidity and thickness suitable for patterning. In one exemplary embodiment, polarizer filter 322 may be about 2500 Angstroms thick aluminum metal. Other materials that may be employed to form polarizer filter 322 include, but are not limited to, silicon nitride, silicon dioxide, etc. As shown monolithic polarizer filter may be patterned into a linear diffraction grating that includes elongated grating elements (wires) 324 that are separated by elongated spaces 326. It will be understood that dimensions of such a diffraction grating or other polarizer filter design may vary according to the desired filtering characteristics to be imparted by polarizer filter 322. For example, in one exemplary embodiment grating elements 324 may be 0.5 micron wide wires that are spaced apart by a 1 micron center to center period. In another exemplary embodiment, grating elements 324 may be 1 micron wide wires that are spaced apart by a 2.5 micron center to center period. Other grating element widths and/or period spacings are possible. In this regard, grating element width and period may be selected based on factors such as spectrum or spectra to be filtered, required polarizer efficiency, etc.

Monolithic polarizer filters 322 may be formed using any technique suitable for monolithically fabricating polarizing filters 322 aligned in place above corresponding microbolometer pixel membrane structures 312. In this regard, an array of microbolometer pixel membrane structures 312 may be coated with a second layer of polyimide (e.g., about 1 to about 3 microns or any other suitable thickness) or other suitable second sacrificial layer after the layers of membrane structures 312 are formed. The layers for the corresponding monolithic polarizer filters 322 may then be formed above the second sacrificial layer, and interconnects 320 may be made through vias in the second sacrificial layer to support the monolithic polarizer filters 322. Thereafter, the second sacrificial layer may be removed from beneath the polarizer filters 322 by undercutting, e.g., by oxygen plasma isotropic etch. An oxygen plasma isotropic etch may be employed, for example, to etch beneath (undercut) the suspended portions of the monolithic polarizer filters 322. Since electrically and/or thermally insulating interconnects 320 connect directly to the conductive interconnects 308 that support the first level microbolometer pixel membrane structure 312, the polarizer filter structure 322 does not add thermal mass to the microbolometer pixel membrane structure 312. It will be understood that either or both of interconnects 320 and/or monolithic polarizer filters 322 may be electrically insulating such that a current path is not formed that bypasses the microbolometer pixel membrane structure 312.

Optical element support interconnects 320 for monolithic polarizer filter 322 may be of any material and thickness suitable for supporting polarizer 322 and meeting thermal and electrical property requirements. For example, in one exemplary embodiment an electrically conductive (e.g., aluminum) polarizer filter 322 may be supported by electrically insulating (e.g., silicon nitride, silicon oxide, silicon oxynitride, or other suitable electrically insulating material) optical element support interconnects 320, although it will be understood that electrically conductive optical element support interconnects 320 may be employed where polarizer filter 322 is non-electrically conductive or where a separate electrically insulating material is present to prevent occurrence of an electrical short between electrically conductive interconnects 308 through polarizer filter structure 322. Optical element support interconnects 320 may be selectably fabricated to a height that matches the second sacrificial layer (e.g., polyimide layer) to achieve desired spacing (e.g., about 2 microns), and may be provided as plug interconnects, etc. In one exemplary embodiment, polarizer filter 322 and optical element support interconnects 320 may be fabricated so that insulating material (e.g., silicon nitride) used to form the insulating interconnects optionally remains over (i.e., overlays) a portion or substantially all of the entire upper surface of the monolithic polarizer filter 322 (e.g., 2500 Angstroms thick aluminum metal grating). However, it is not necessary that such an insulating material overlay monolithic polarizer filter 322. In another embodiment, each of optical element support interconnects 320 may be formed from a downwardly-protruding extension of the filter material. In one exemplary embodiment, each of optical element support interconnects 320 may be configured in hollow tubular form (e.g., cylindrical, square, etc.), having a wall thickness of about 1750 angstroms, although solid interconnects or interconnects having greater or lesser wall thicknesses may be alternately employed.

Figure 4:
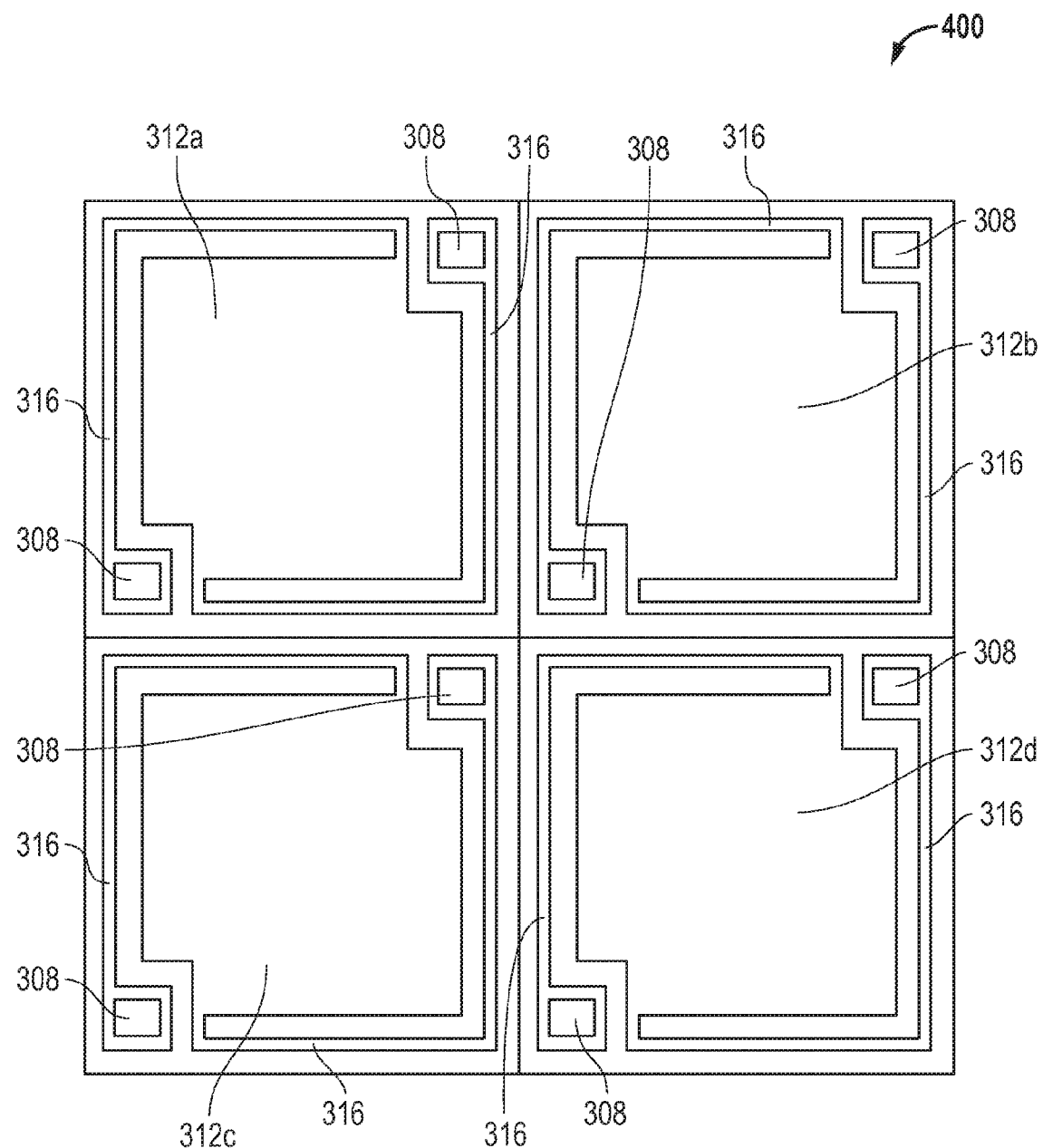
FIG. 4 illustrates a top view of a subarray according to one exemplary embodiment of the disclosed apparatus and methods.

In one exemplary embodiment, adjacent uncooled infrared detector elements 300 of a focal plane array 212 may be provided with differently-configured monolithic polarization filters 322, e.g., so that adjacent infrared detector element pixels 300 absorb different polarization components of the scene infrared radiation. For example, FIG. 4 illustrates a 2×2 subarray 400 of four adjacent microbolometer pixel membrane structures 312a-312d, shown without overlying polarizer filter structures 322. Subarray 400 may form a part of a larger FPA 212, e.g., such as a 30 micron pixel 320×240 amorphous silicon microbolometer FPA 212. In this embodiment, no openings 310 are defined in pixel membrane structures 312a-312d, although such openings may be present in other embodiments.

Figure 5:
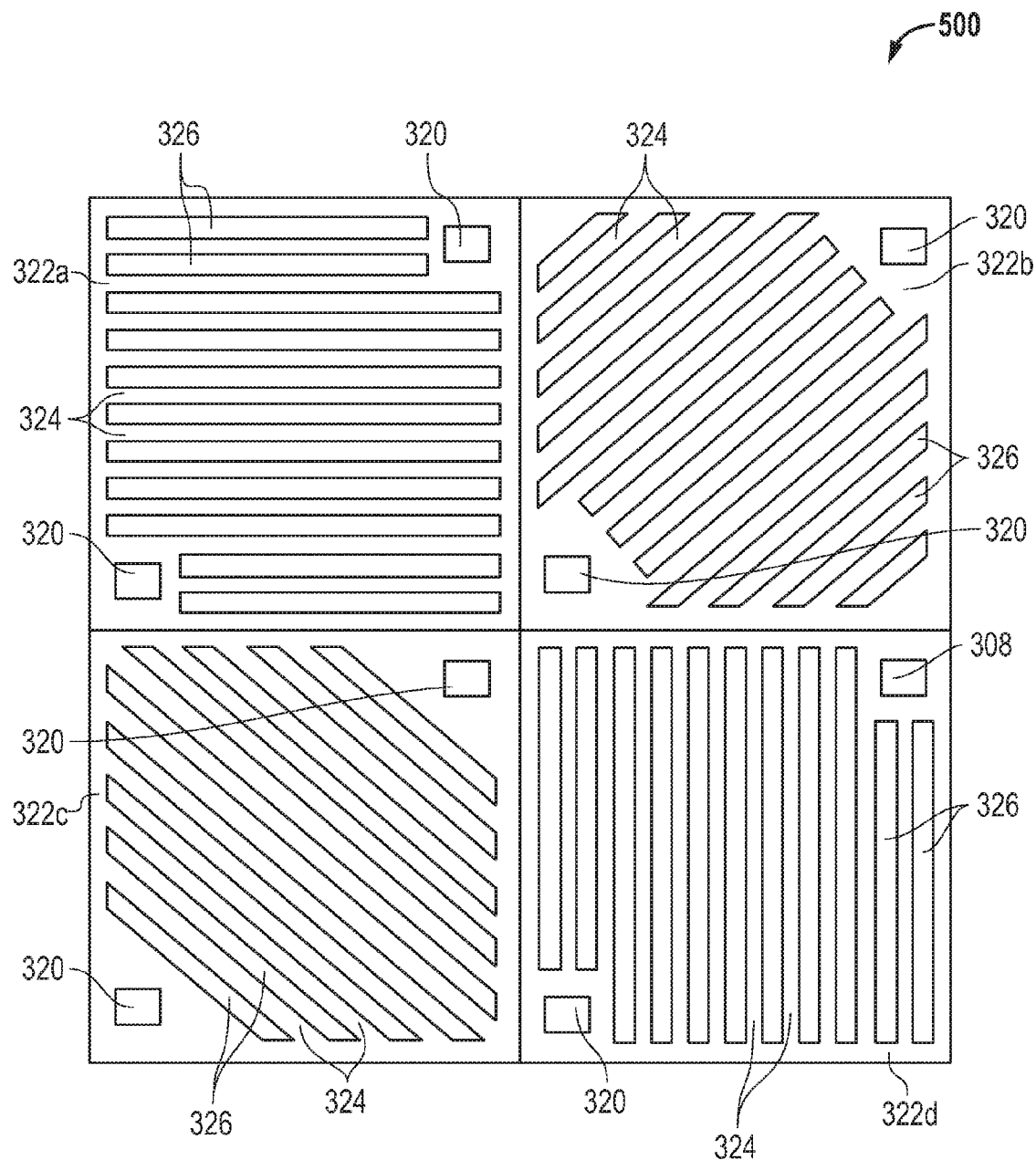
FIG. 5 illustrates a top view of a subarray according to one exemplary embodiment of the disclosed apparatus and methods.
Figure 6:
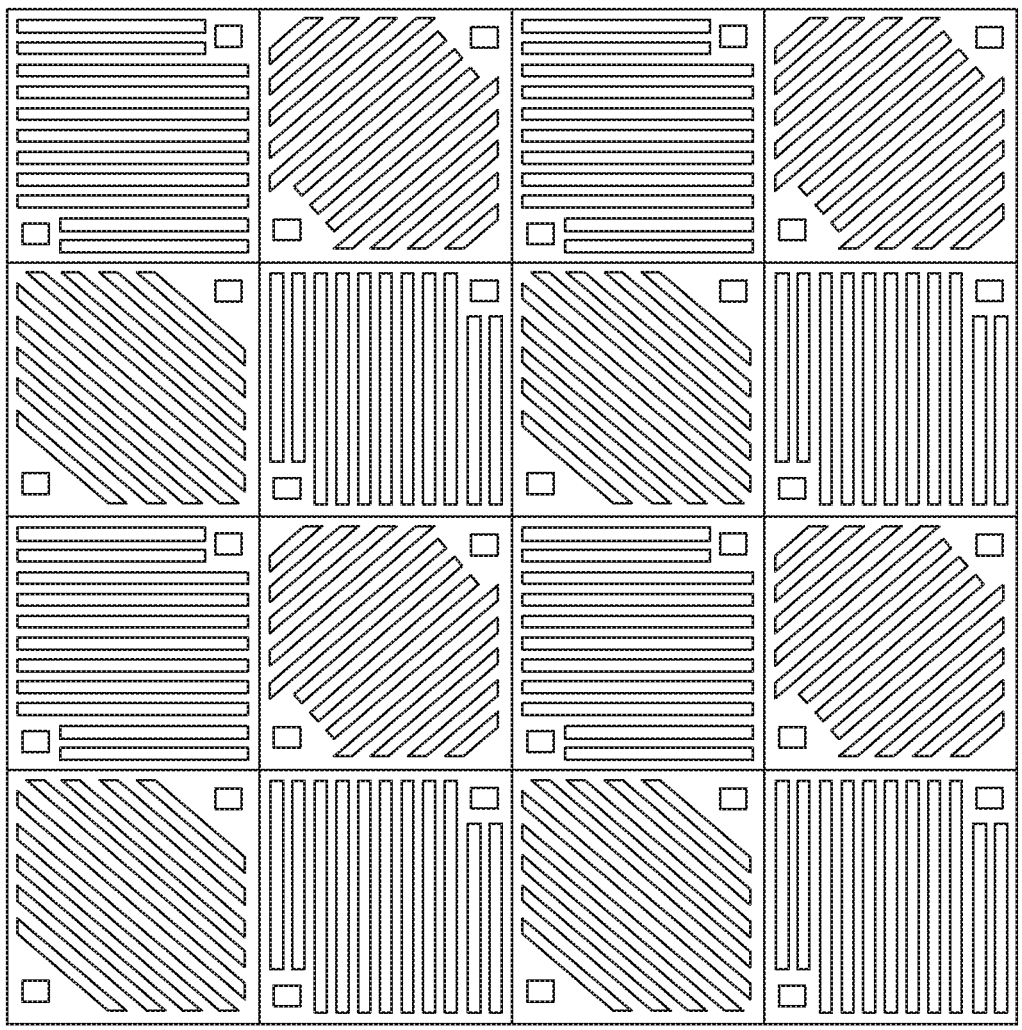
FIG. 6 illustrates a top view of a focal plane array according to one exemplary embodiment of the disclosed apparatus and methods.

FIG. 5 illustrates a 2×2 subarray 500 that includes polarizer filter structures 322a-322d in place overlying the corresponding microbolometer pixel membrane structures 312a-312d of 2×2 subarray 400. As shown in FIG. 5, the polarizer filter structures of FIG. 5 include horizontal monolithic grating structure 322a, +45° monolithic grating structure 322b, −45° monolithic grating structure 322c, and vertical monolithic grating structure 322d. In the illustrated embodiment of FIG. 5, four polarizations (corresponding to four Stokes vectors) are included in 2×2 subarray 500. However, it will be understood that the embodiment of FIG. 5 is exemplary only, and that any other combination of two or more differently-configured monolithic polarization filters 322 may be employed in the same FPA 212, in a regular or irregular pattern, or in a random arrangement. FIG. 6 illustrates the pattern of 2×2 subarray 500 of FIG. 5 repeated to form a larger polarized imaging focal plane array 550.

Figure 7:
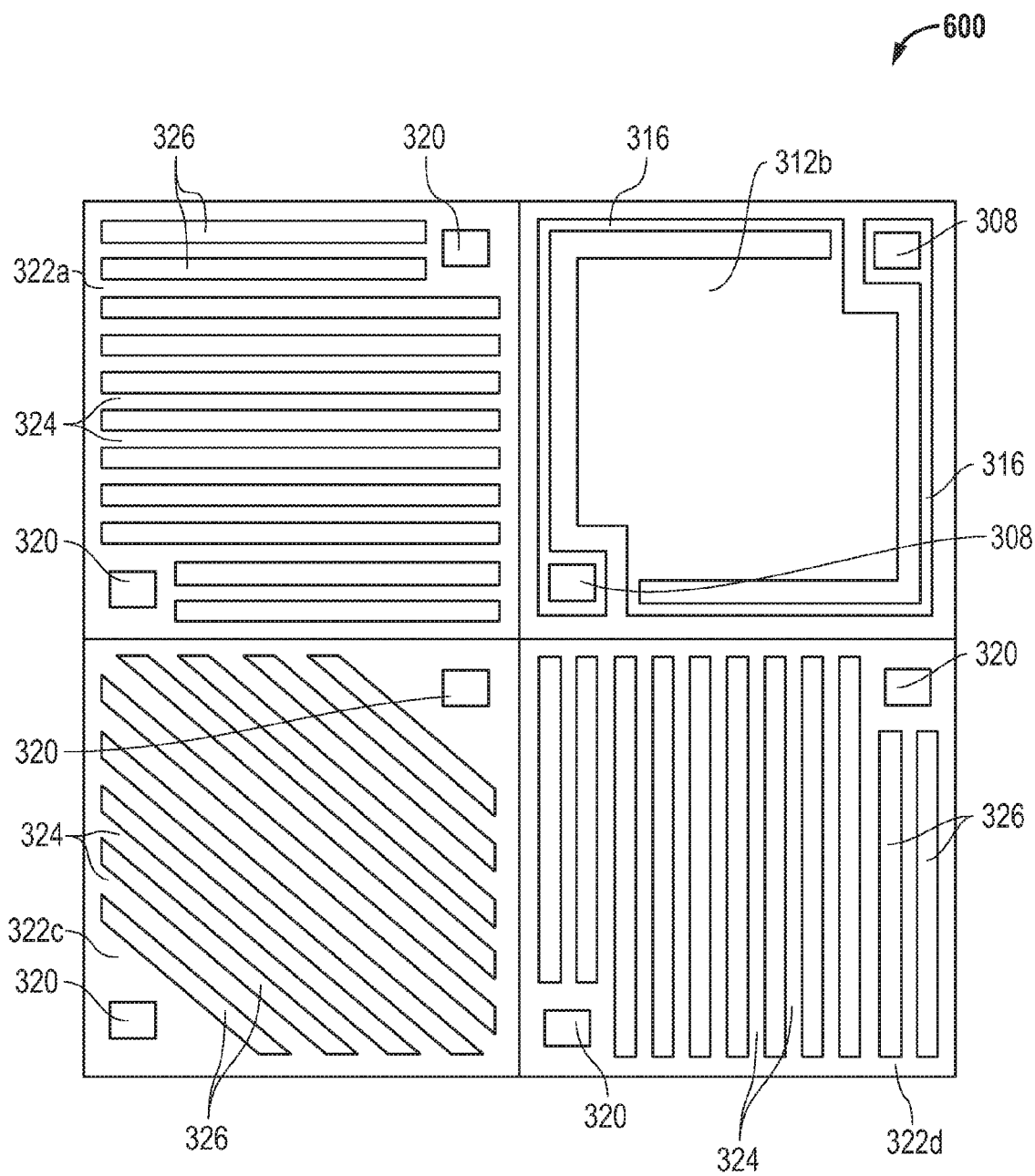
FIG. 7 illustrates a top view of a subarray according to one exemplary embodiment of the disclosed apparatus and methods.

In an alternative embodiment, one or more microbolometer pixel membrane structures 312 of a focal plane array 212 may be left uncovered with no overlying polarizer filter structure 322. For example, FIG. 7 illustrates a 2×2 subarray 600 similar to subarray 500 of FIG. 5, with the exception that the +45° polarizer filter structure 322b has been omitted so that microbolometer pixel membrane structure 312b absorbs unfiltered and randomly polarized scene radiation. It will be understood that FIG. 7 is exemplary only, and that any one or more polarizer filter structures 312 may be omitted, and/or any one or more microbolometer pixel membrane structures 312 may be left uncovered, in a regular or irregular pattern, or in a random arrangement.

Figure 8:
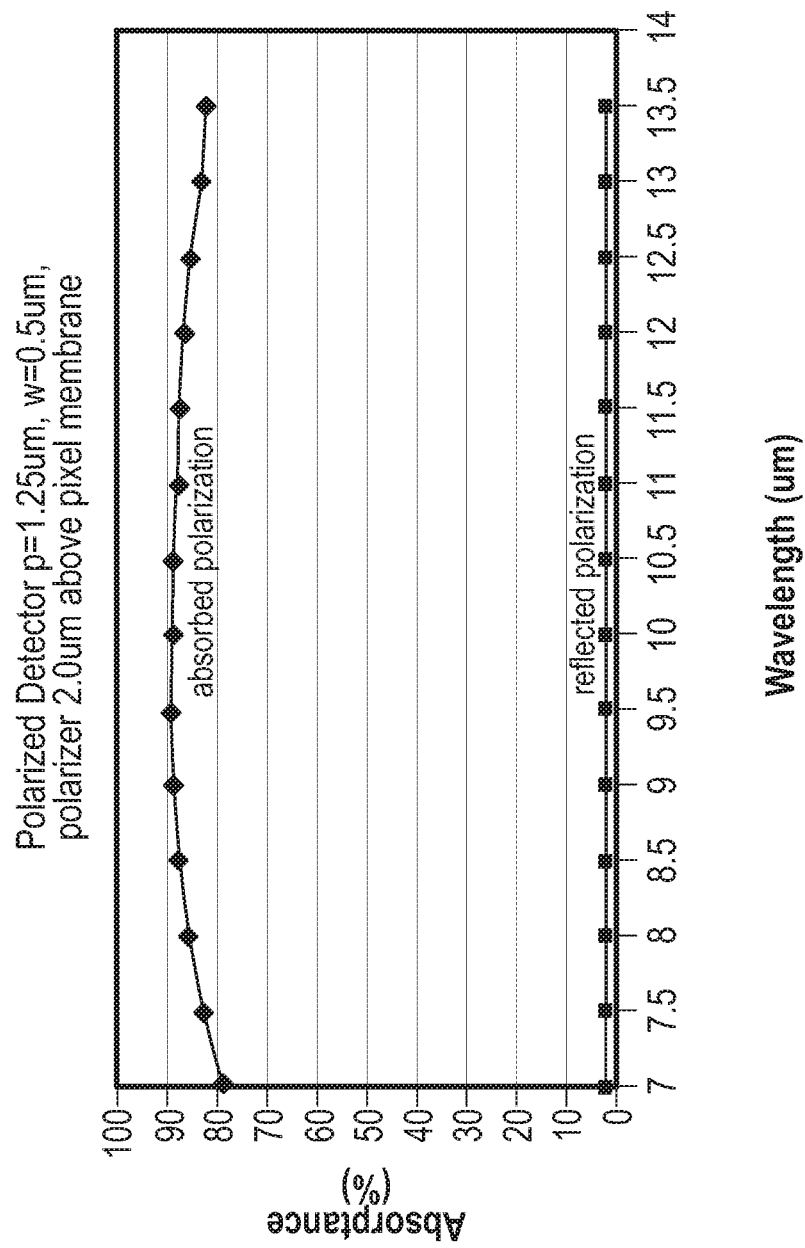
FIG. 8 illustrates absorptance versus wavelength according to one exemplary embodiment of the disclosed apparatus and methods.
Figure 9:
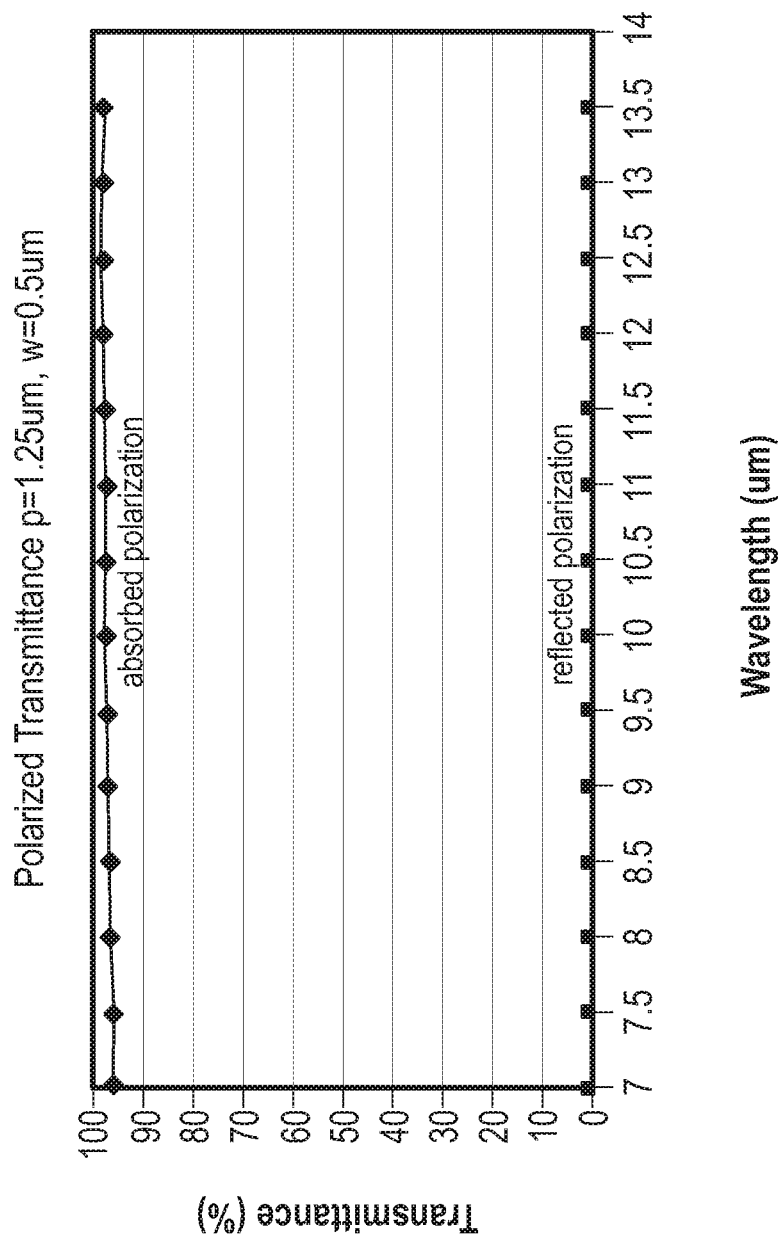
FIG. 9 illustrates polarizer transmittance versus wavelength according to one exemplary embodiment of the disclosed apparatus and methods.

FIGS. 8 and 9 illustrate polarization sensitivity for an uncooled infrared detector element 300 of one exemplary embodiment having a polarizer filter 322 in the form of a monolithic grating structure fabricated about 2 microns above a microbolometer pixel membrane structure 312. In this embodiment, the grating structure 322 has grating elements 324 that are 0.5 micron wide wires spaced apart by a 1.25 micron center to center period. In particular, FIG. 8 illustrates absorptance plotted versus wavelength, and shows absorptance of about 2% in parallel mode that may be mostly attributed to the polarizer filter 322. FIG. 9 illustrates polarizer transmittance versus wavelength, and shows perpendicular transmittance that is greater than 95% and parallel transmittance of less than 0.4%. This yields a discrimination ratio of greater than about 237 (>95/0.4). Absorptance in grating is about 1.5% in parallel mode.

Figure 10:
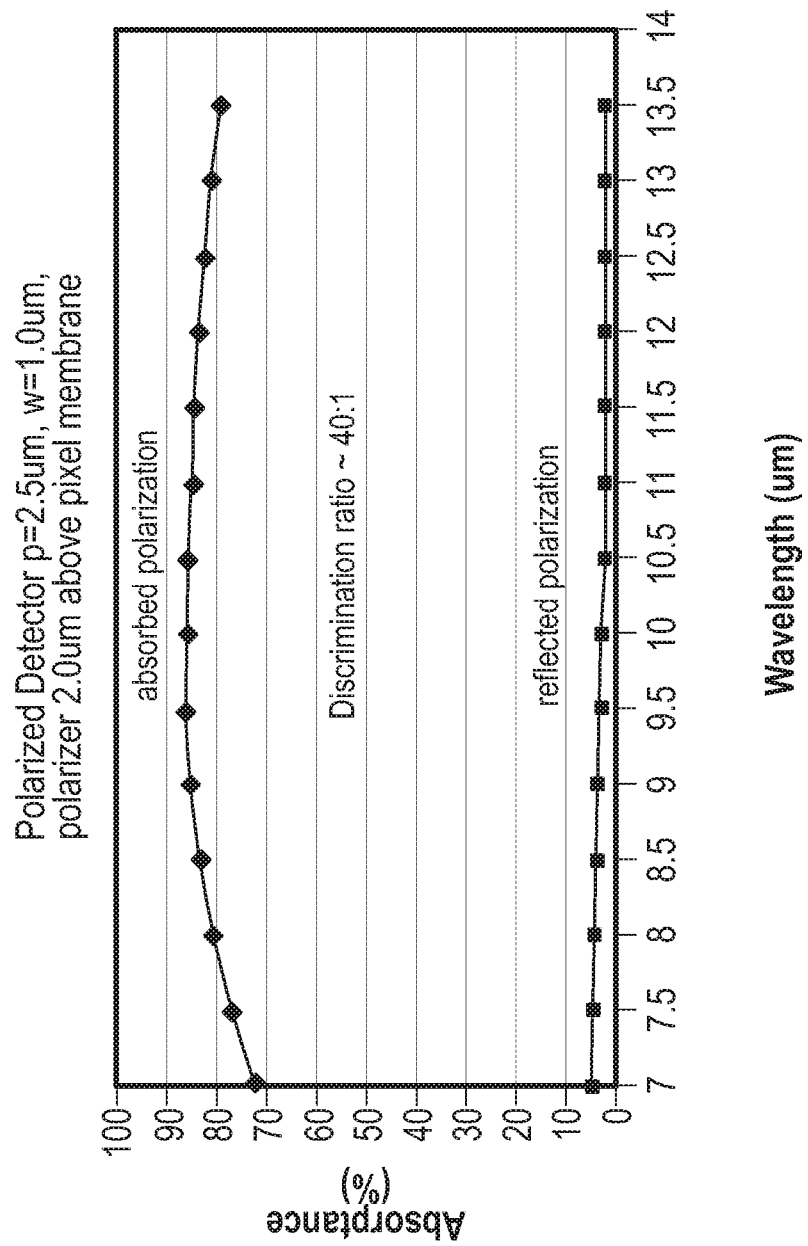
FIG. 10 illustrates absorptance versus wavelength according to one exemplary embodiment of the disclosed apparatus and methods.
Figure 11:
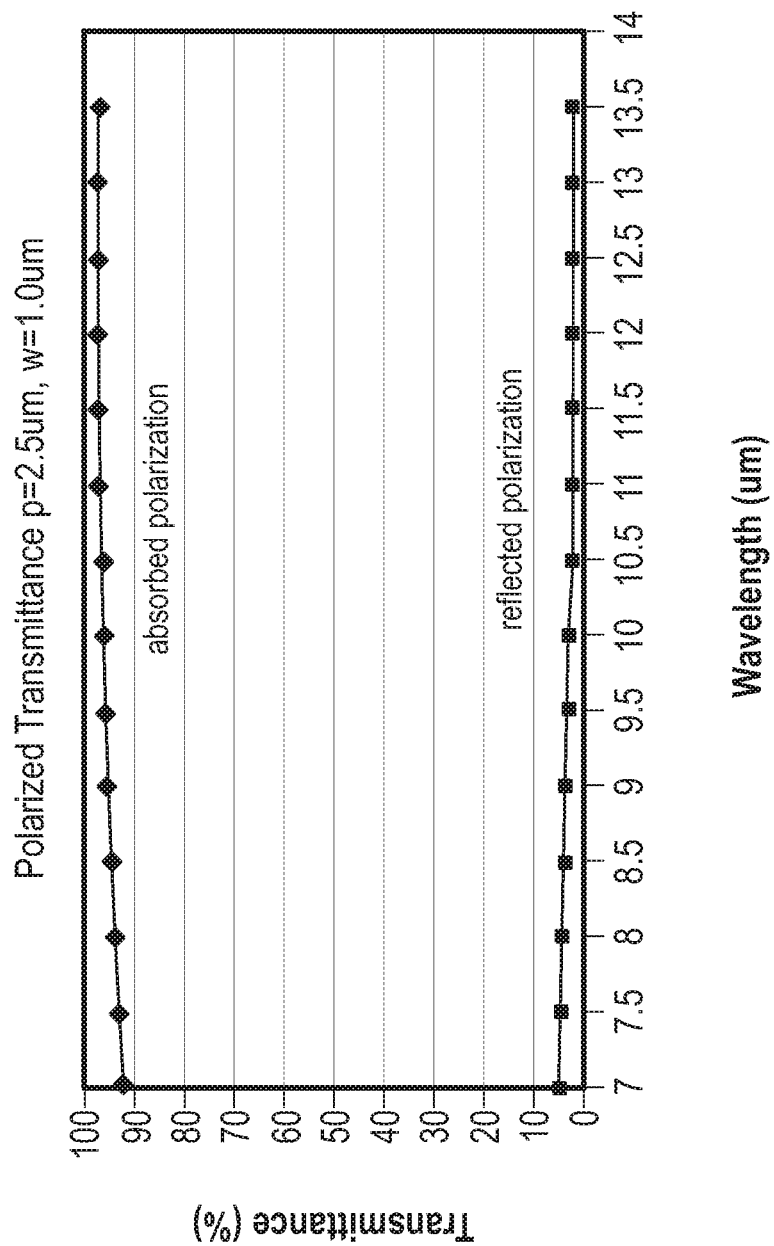
FIG. 11 illustrates polarizer transmittance versus wavelength according to one exemplary embodiment of the disclosed apparatus and methods.

FIGS. 10 and 11 illustrate polarization sensitivity for an uncooled infrared detector element 300 of one exemplary embodiment having a polarizer filter 322 in the form of a monolithic grating structure fabricated 2 microns above a microbolometer pixel membrane structure 312. In this embodiment, the grating structure 322 has grating elements 324 that are 1 micron wide wires spaced apart by a 2.5 micron center to center period. In particular, FIG. 10 illustrates absorptance plotted versus wavelength, and shows absorptance of about 2% in parallel mode that may be mostly attributed to the polarizer filter 322. FIG. 11 illustrates polarizer transmittance versus wavelength, and shows perpendicular transmittance that is about 95% and parallel transmittance of about 2.5%. This yields a discrimination ratio of about 38 (>95/2.4). Absorptance in grating is about 1.5% in parallel mode.

Figure 12:
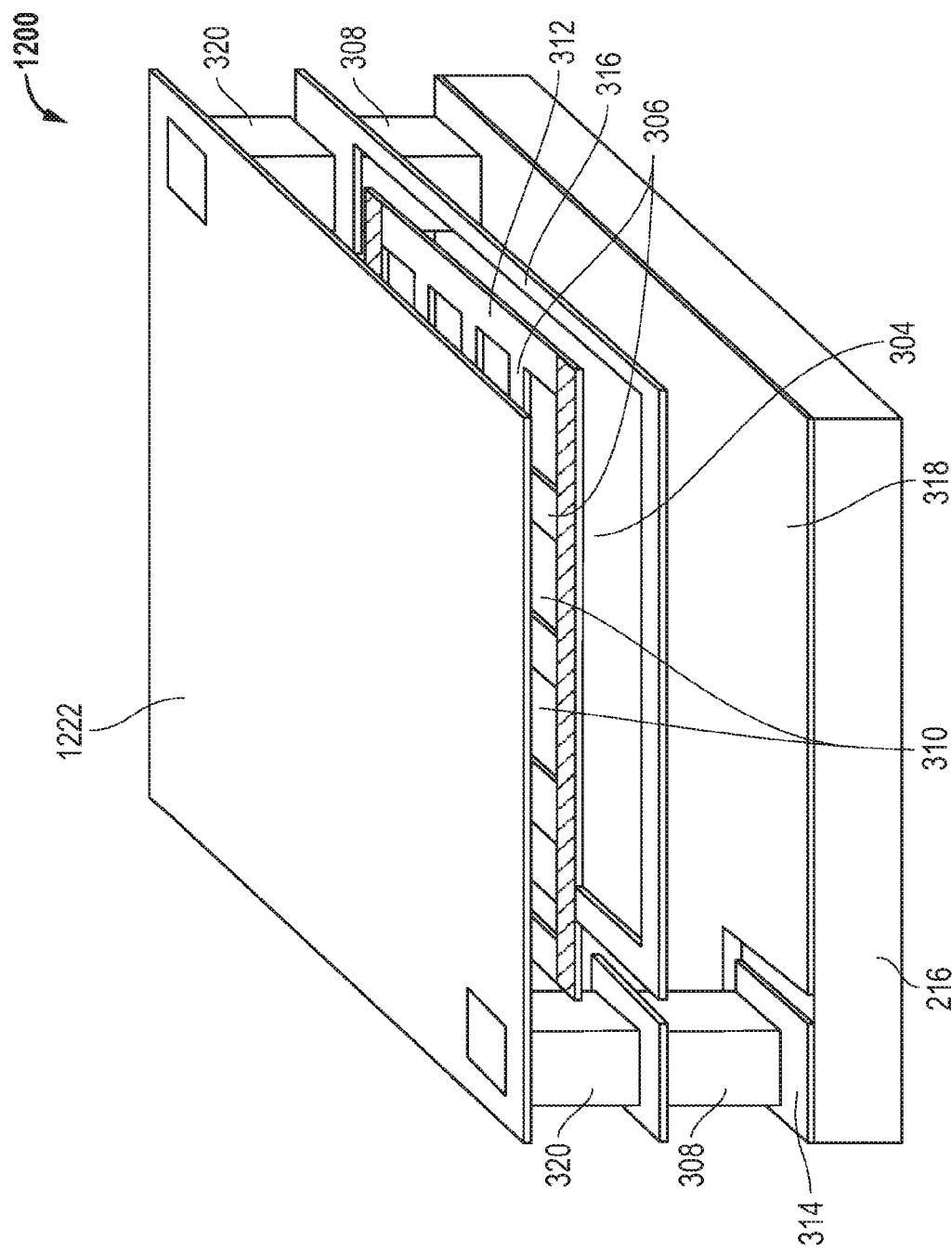
FIG. 12 illustrates a perspective view of an uncooled infrared detector element according to one exemplary embodiment of the disclosed apparatus and methods.

FIG. 12 illustrates one exemplary embodiment of an infrared detector element 1200 that includes an optical element in the form of a monolithic spectral filter 1222 suspended by two optical element support interconnects 320 (e.g., at a distance of about 1 to 3 microns) over and above a microbolometer pixel membrane structure 312 and associated silicon semiconductor substrate 216 and optional reflector 318 of the same type described in relation to FIG. 3. In this regard, microbolometer pixel membrane structure 312 is itself suspended above silicon semiconductor substrate 216 by relatively long thermal isolation legs 316 that are electrically connected to the ROIC of the semiconductor substrate 216 by the metal interconnects 308 via conductive input pads 314. As with the embodiment of FIG. 3, a microbolometer pixel membrane structure 312 may be suspended greater than or less than about 2 microns above silicon semiconductor substrate 216 in other embodiments. It will be understood that a plurality of infrared detector elements 1200 may be employed in a manner similar to infrared detector elements 300 to form a focal plane array focal plane array 212 such as illustrated and described in relation to FIG. 2.

In one embodiment of FIG. 12, monolithic spectral filter 1222 may be configured as a stack of optical thin film layers characterized by a thickness and refractive index that serves a spectral filtering function, e.g., such as forming a spectral band pass which confines the radiation absorbed by microbolometer pixel membrane structure 312 to be within a specific spectral band pass. Other examples of spectral filter types include, but are not limited to, high pass filter, low pass filter, notch filter (e.g., to filter out laser radiation), etc.

For example, spectral filter 1222 may be configured in one exemplary embodiment for passing LWIR radiation using the film layers 1620, 1622 and 1624 and corresponding thicknesses of Table 1 below, and in another exemplary embodiment for passing MWIR radiation using the film layers 1620, 1622 and 1624 and corresponding thicknesses of Table 2 below. In the first of such embodiments, overall thickness of filter 1222 may be about 0.17 microns and may limit radiation passed for absorption by microbolometer pixel membrane structure 312 to those absorbed long to very long wave wavelengths shown in FIG. 17. In the second of such embodiments, overall thickness of filter 1222 may be about 0.13 microns and may limit radiation passed for absorption by microbolometer pixel membrane structure 312 to those absorbed midwave wavelengths shown in FIG. 18. It will be understood that in other embodiments, spectral filter 1222 may be configured with other thickness and refractive index values to limit absorption of other wavelengths. Alternatively, spectral filter 1222 may be configured to serve a band stop function in which the radiation in the spectral band stop is substantially prevented from being absorbed by the underlying membrane structure 312. In any case, optical element support interconnects 320 may be configured from similar materials (e.g., electrically insulating SiN) and with similar dimensions as previously described in relation to FIG. 3, and may in one embodiment be formed from downwardly protruding extensions of the filter stack layers. Optical element support interconnects 320 may be disposed on electrically conductive interconnects 308 (e.g., TiW) as shown to minimize any addition to the pixel thermal mass or change to the pixel time constant.

In yet another embodiment, monolithic spectral filter 1222 may be replaced with an overlying optical block structure that shields the underlying microbolometer pixel membrane structure 312 substantially completely from incoming radiation. This may be done to configure one or more uncooled infrared detector elements 300 as "blind pixels" that may serve as reference pixels when combined with non-blind infrared detector elements 300 that act as active imaging pixels. In this regard, such "blind" reference pixels have a dark signal response that may be used as a baseline for measuring the response of the active imaging pixels exposed to incoming radiation. Such an overlying optical block embodiment structure may be of any material and/or configuration suitable for substantially blocking all incoming radiation in the spectral band to which the underlying microbolometer pixel membrane structure 312 is designed to respond, e.g., a thin metal reflective layer, a reflecting dielectric layer stack, and absorbing metal, an absorbing layer stack, etc. In such an embodiment, uncooled infrared detector elements 300 with optical block structures may be randomly or systematically distributed over microbolometer pixel membrane structures 312 of FPA 212.

Figure 13:
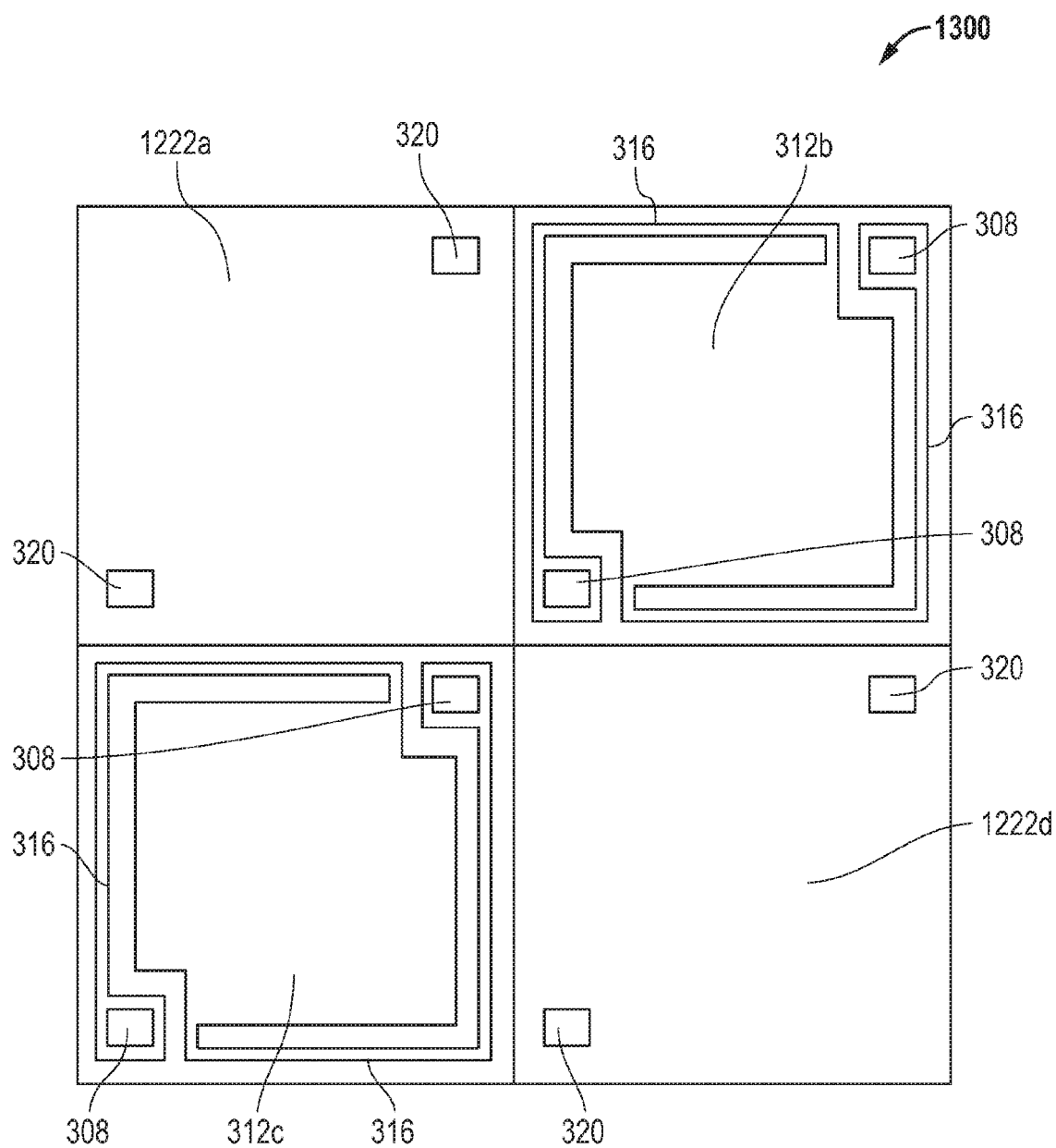
FIG. 13 illustrates a top view of a subarray according to one exemplary embodiment of the disclosed apparatus and methods.
Figure 14:
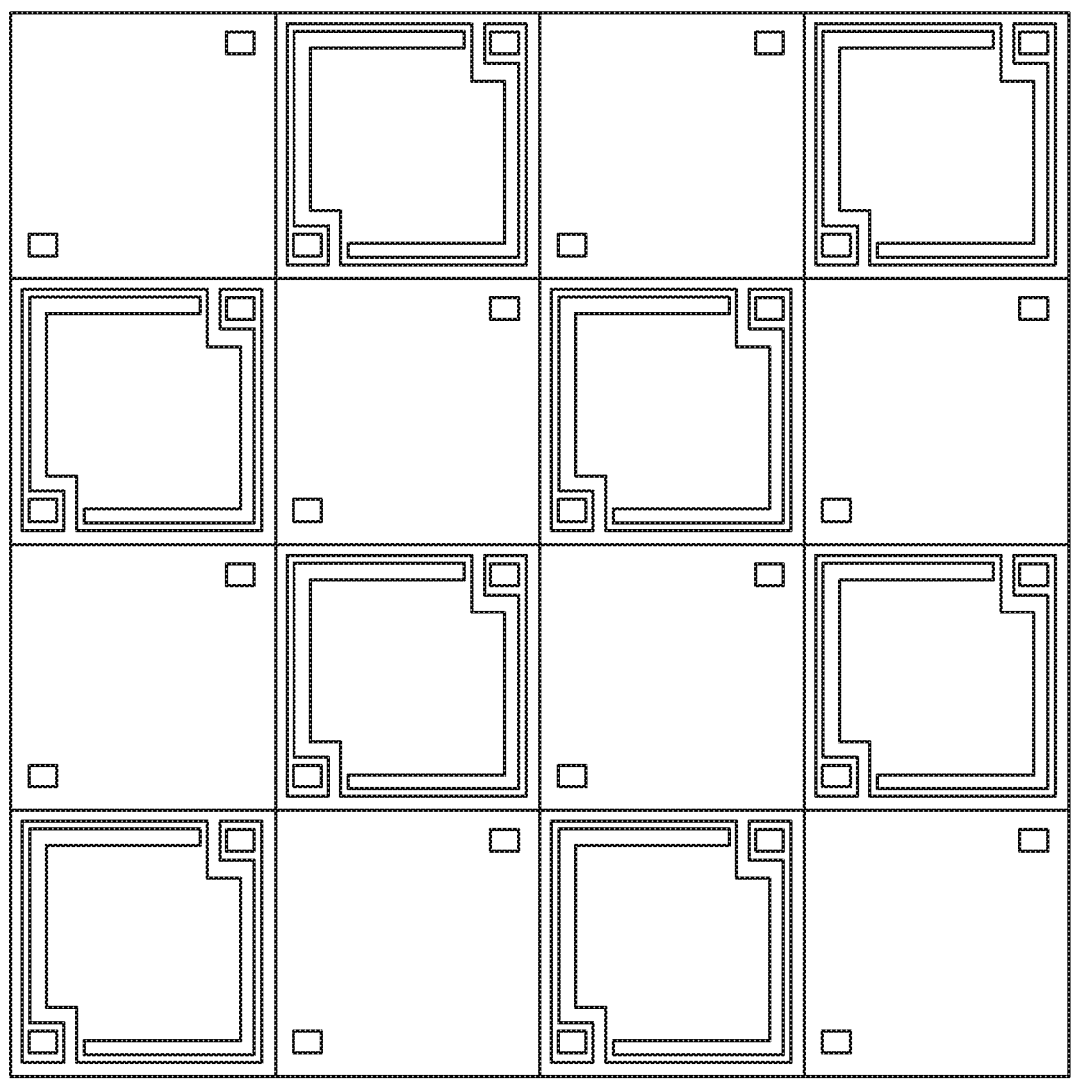
FIG. 14 illustrates a top view of a focal plane array according to one exemplary embodiment of the disclosed apparatus and methods.

In an alternative embodiment, one or more microbolometer pixel membrane structures 312 of a focal plane array 212 may be covered with a spectral filter structure 1222, while one or more other microbolometer pixel membrane structures 312 of the same focal plane array 212 may be left uncovered with no overlying spectral filter structure 1222. For example, FIG. 13 illustrates a 2×2 subarray 1300 in which only alternating microbolometer pixel membrane structures 312 are provided with monolithically integrated spectral filters 1222. In FIG. 13, a 2×2 subarray 1300 of four adjacent microbolometer pixel membrane structures 312a-312d as shown in FIG. 4 is overlain by alternating monolithically integrated spectral filter structures 1222a and 1222d, leaving microbolometer pixel membrane structures 312b and 312c uncovered to receive unfiltered scene radiation. It will be understood that FIG. 13 is exemplary only, and that any one or more spectral filter structures 1222 may be provided, and/or any one or more microbolometer pixel membrane structures 312 may be left uncovered, in a regular or irregular pattern, or in a random arrangement. FIG. 14 illustrates the pattern of 2×2 subarray 1300 of FIG. 13 repeated to form a larger pixel-level spectrally filtered imaging focal plane array 1400 in which every other microbolometer pixel membrane structure 312 is provided with a monolithically integrated spectral filter structure 1222.

Figure 15:
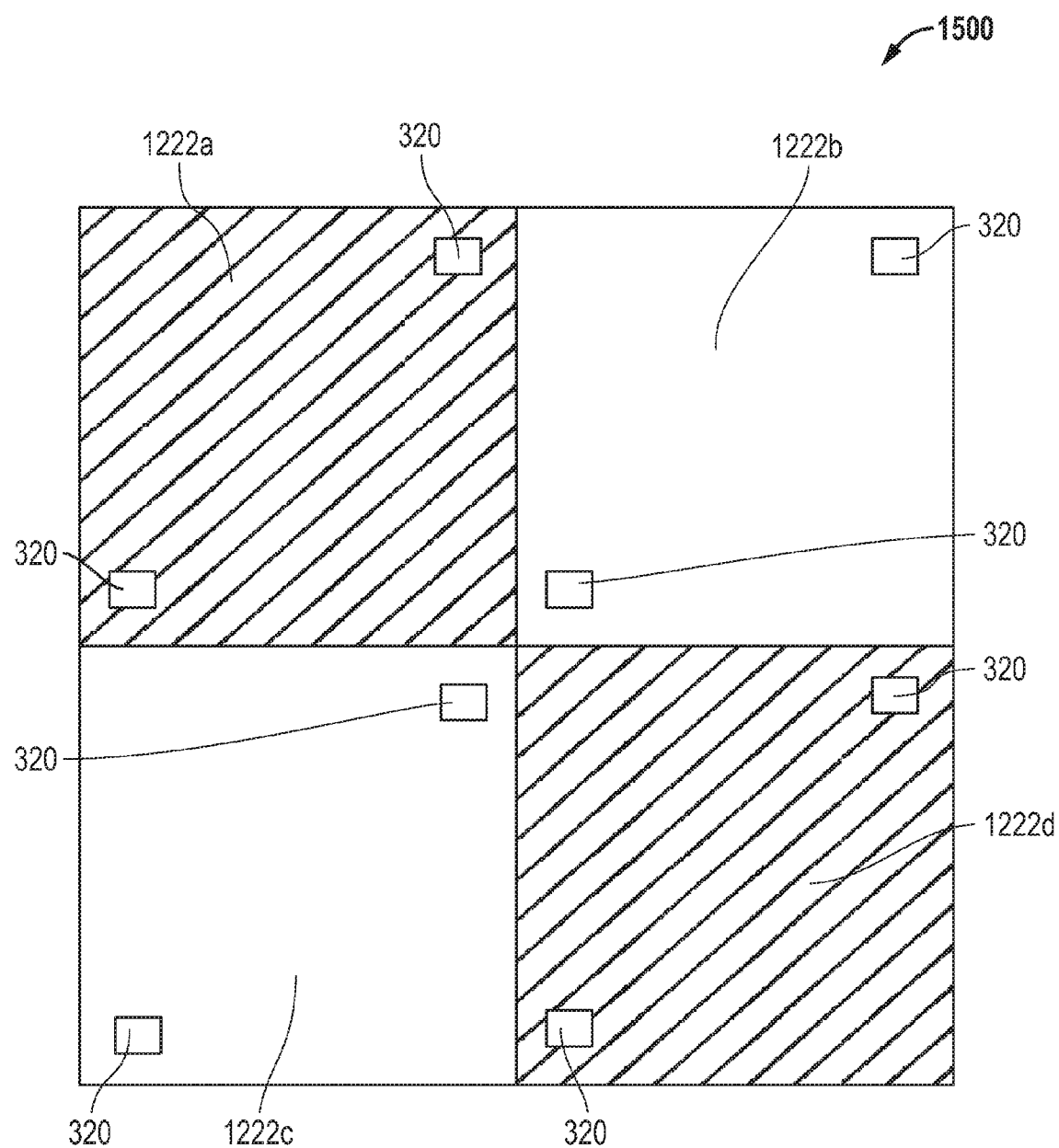
FIG. 15 illustrates a top view of a subarray according to one exemplary embodiment of the disclosed apparatus and methods.

FIG. 15 illustrates another embodiment in which a 2×2 subarray 1500 includes four adjacent microbolometer pixel membrane structures 312a-312d of FIG. 4 that are overlain by respective alternating different types of monolithically integrated spectral filter structures 1222. In this regard, a first type of spectral filter structures (1222a and 1222d) are positioned adjacent a second type of spectral filter structures (1222b and 1222c). For example, in one exemplary embodiment, the first type of spectral filter structures may be mid-wave IR, and the second type of spectral filter structures may be long-wave IR, or sub-bands of such. However, any other two or more different types of filter structures may be so positioned over microbolometer pixel membrane structures 1222 of a focal plane array 212, in a regular or irregular pattern, or in a random arrangement.

Figure 16:
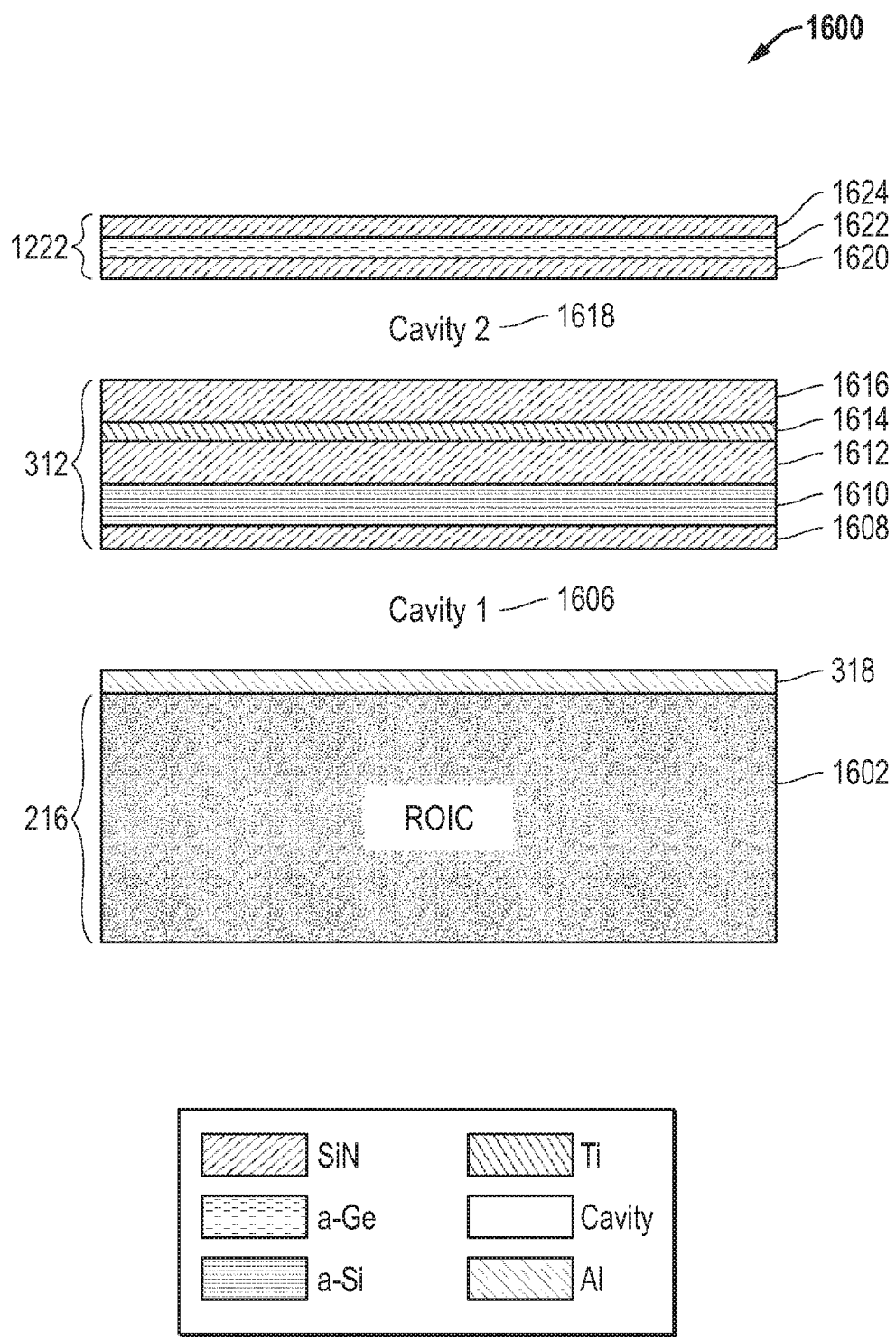
FIG. 16 illustrates a side cross-sectional view of a material layer sequence of an uncooled infrared detector element according to one exemplary embodiment of the disclosed apparatus and methods.

FIG. 16 illustrates a side cross-sectional view of a material layer sequence 1600 for one exemplary embodiment of an uncooled infrared detector element 1200 that monolithically incorporates a spectral filter 1222 such as described and illustrated in relation to FIG. 12. In one embodiment, the layers of FIG. 16 may be formed by deposition on top of a substrate 216 and ROIC 1602. As shown in FIG. 16, layer sequence 1600 includes ROIC 1602 of substrate 216 with optional reflective aluminum layer 318 disposed thereon. A first cavity 1606 separates substrate 216 and reflective layer 318 from microbolometer pixel membrane structure 312, which itself includes silicon nitride layers 1608 and 1612 with a thermally-electrically active layer 1610 of amorphous silicon therebetween. Titanium absorber layer 1614 overlays silicon nitride layer 1612, and is overlain itself by silicon nitride layer 1616 to complete microbolometer pixel membrane structure 312. The particular layers illustrated in FIG. 16 for pixel membrane structure 312 are exemplary only, and may be varied in number, type and/or thicknesses to obtain the desired infrared detection characteristics. A second cavity 1618 separates microbolometer pixel membrane structure 312 from spectral filter 1222, which itself includes silicon nitride layers 1620 and 1624 with amorphous germanium layer 1622 therebetween. Layers of spectral filter 1222 define the spectral response of the composite spectral filter structure and may be varied in number, type and/or thicknesses to obtain a desired spectral response.

Any technique suitable for monolithically fabricating spectral filters 1222 in place above corresponding microbolometer pixel membrane structures 312 may be employed. For example, as previously described for the polarizer filter embodiments, an array of microbolometer pixel membrane structures 312 may be coated with a second layer of polyimide or other suitable second sacrificial layer (e.g., about 1 to 3 microns or any other suitable thickness) after the layers of membrane structures 312 are formed. The layers for the corresponding monolithic spectral filters 1222 may then be formed above the second sacrificial layer, and interconnects 320 may be made through vias in the second sacrificial layer to support the spectral filter structures 1222. Thereafter, the layers of the spectral filters 1222 may be etched down through the second sacrificial layer to the underlying membrane structures 312. An oxygen plasma isotropic etch may be employed, for example, to etch beneath (undercut) the suspended portions of the monolithic spectral filters 1222. Since interconnects 320 connect directly to the conductive interconnects 308 that support the first level microbolometer pixel membrane structure 312, the spectral filter structure 1222 does not add thermal mass to the microbolometer pixel membrane structure 312.

It will be understood that a similar material layer sequence as shown in FIG. 16 may be employed for microbolometer pixel membrane structures of other optical element embodiments disclosed herein if desired, such as for the uncooled infrared detector element 300 of FIG. 3 that includes a monolithic polarizer filter 322 suspended over and above the microbolometer pixel membrane structure 312. In such cases, layers 1620, 1622 and 1624 of spectral filter 1222 may be replaced with materials/layers appropriate to the type of optical element being implemented, e.g., replaced with an aluminum metal or other suitable polarizer structure layer of monolithic polarizer filter 322 as described and illustrated in relation to FIG. 3.

Table 1 illustrates exemplary dimensions for one possible embodiment of a long wave infrared (LWIR) detector embodiment using the material layer sequence 1600 of FIG. 16.

TABLE 1

LWIR Layer Structure

| Layer | Material | Layer Thickness (micrometers) |
|---|---|---|
| 1318 | Aluminum | 0.25 |
| 1606 | Vacuum Cavity | 2.15 |
| 1608 | Silicon Nitride | 0.03 |
| 1610 | Silicon | 0.065 |
| 1612 | Silicon Nitride | 0.04 |
| 1614 | Titanium | 0.025 |
| 1616 | Silicon Nitride | 0.05 |
| 1618 | Vacuum Cavity | 0.8 |
| 1620 | Silicon Nitride | 0.03 |
| 1622 | Germanium | 0.11 |
| 1624 | Silicon Nitride | 0.03 |

Figure 17:
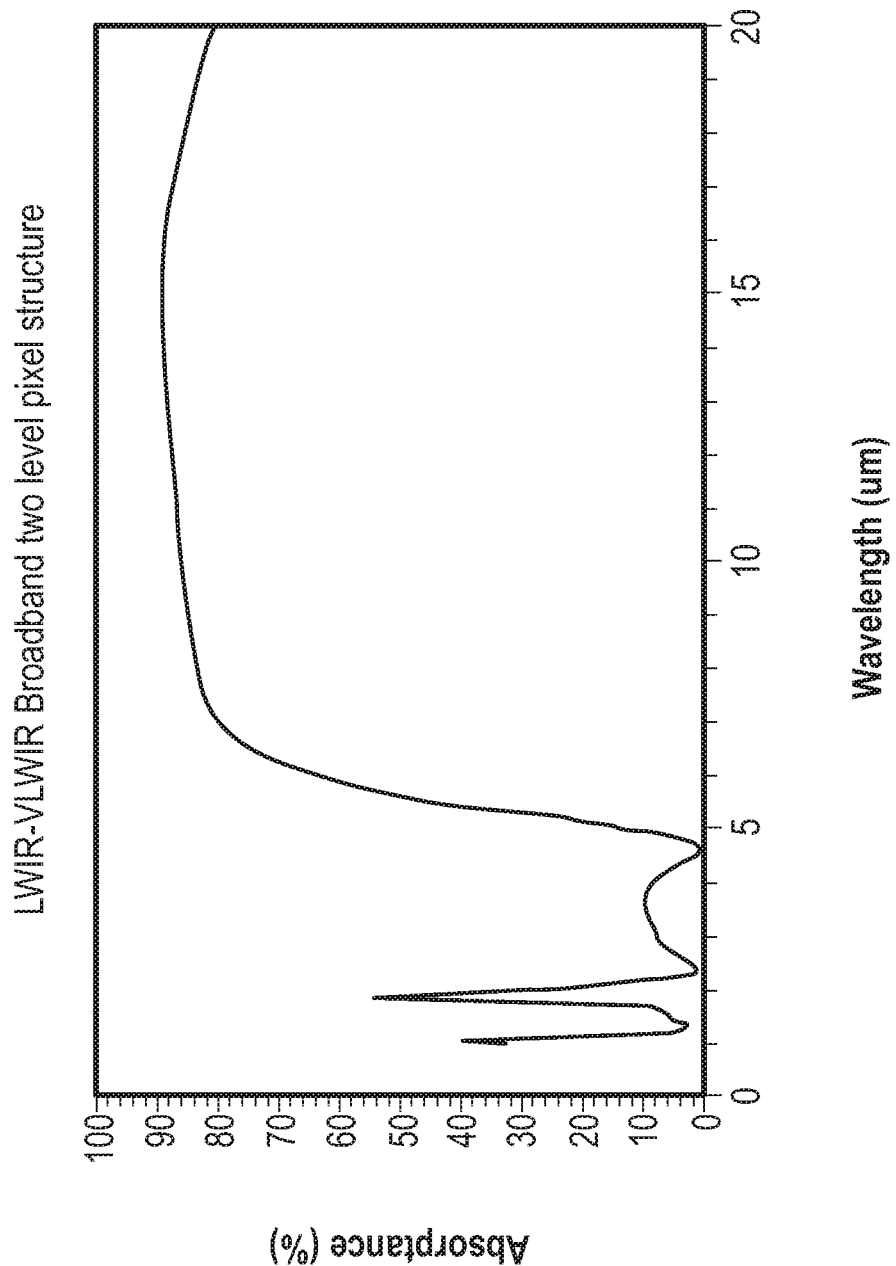
FIG. 17 illustrates absorptance versus wavelength according to one exemplary embodiment of the disclosed apparatus and methods.

FIG. 17 illustrates broadband (long wave infrared LWIR to very long wave infrared VLWIR) spectral response in the 8 to 12 micron long wave infrared spectral band in terms of detector absorptance versus wavelength for the amorphous-silicon two-level detector embodiment according to the LWIR layer structure of Table 1.

Table 2 illustrates exemplary dimensions for one possible embodiment of a mid wave infrared (MWIR) detector embodiment using the material layer sequence 1600 of FIG. 16.

TABLE 2

MWIR Layer Structure

| Layer | Material | Layer Thickness (micrometers) |
|---|---|---|
| 1318 | Aluminum | 0.25 |
| 1606 | Vacuum Cavity | 0.25 |
| 1608 | Silicon Nitride | 0.03 |
| 1610 | Silicon | 0.06 |
| 1612 | Silicon Nitride | 0.04 |
| 1614 | Titanium | 0.01 |
| 1616 | Silicon Nitride | 0.05 |
| 1618 | Vacuum Cavity | 1 |
| 1620 | Silicon Nitride | 0.03 |
| 1622 | Silicon | 0.06 |
| 1624 | Silicon Nitride T | 0.04 |

Figure 18A:
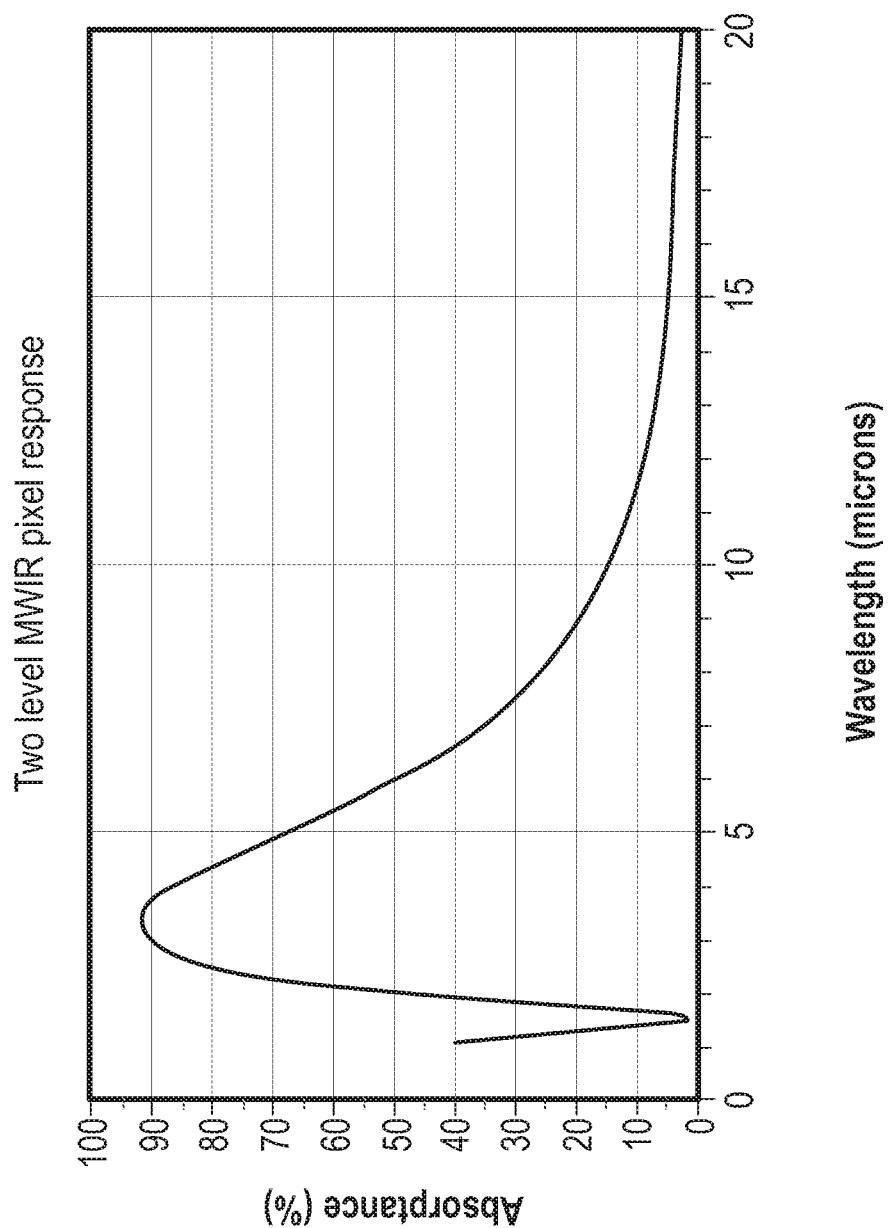
FIG. 18A illustrates absorptance versus wavelength according to one exemplary embodiment of the disclosed apparatus and methods.

FIG. 18A illustrates MWIR spectral response in the 3 to 5 micron mid wave infrared spectral band in terms of detector absorptance versus wavelength for the amorphous-silicon two-level detector embodiment according to the MWIR layer structure of Table 2. It will be understood that the layer structure embodiments of Tables 1 and 2 are exemplary only, and that other materials, layer configurations and layer thicknesses may be employed as suitable or desired for the given application.

FIGS. 19-22 illustrate an exemplary embodiment of a dual band detector element 1900 in which an optical element in the form of a microlens structure 1902 is supported and suspended at a distance of about 3 microns or other suitable distance over and above a microbolometer pixel membrane structure 312 by two insulating optical element support interconnects 320 (e.g., SiN, etc.) that extend down and are substantially aligned to and anchored to the top of electrically conductive interconnects 308 (e.g., TiW, aluminum, etc.) of a DRC microbolometer pixel structure 312 in a manner similar to that previously described for certain other embodiments. As with the previously-described embodiments, conductive interconnects 308 are in turn coupled to readout integrated circuitry of the supporting semiconductor substrate 216 by electrically conductive input pad 314 which may be made of aluminum or other suitably electrically conductive material. In this exemplary embodiment, microbolometer pixel membrane structure 312 is provided with four openings 310 defined therein as shown. It will also be understood that a plurality of infrared detector elements 1900 may be employed in a manner similar to infrared detector elements 300 to form a focal plane array focal plane array 212 such as illustrated and described in relation to FIG. 2.

In the embodiments of FIGS. 19-22, openings 1960 are defined as shown in optional metal reflector 318 (e.g., aluminum, etc.). Openings 1960 of metal reflector 318 are vertically aligned with openings 310 of microbolometer pixel membrane structure 312, which are in turn vertically aligned with indium-gallium-arsenic (InGaAs) diode detectors 1980 as shown. Other exemplary types of detectors 1980 include, but are not limited to, silicon (Si) diode, germanium (Ge) diode, and silicon-germanium (SiGe) diode detectors. In this embodiment, microlens structure 1902 includes an array of four microlenses 1904 that each focus a combination of visible, near IR, and short IR spectrum (VNS) radiation (i.e., substantially all radiation from visible to short IR) through a corresponding opening 310 in reflector metal 318 and other components of the DRC pixel structure onto a corresponding InGaAs, Si, Ge or SiGe detector 1980 imbedded in $SiO_2$ substrate 216 below embedded metal layers 1970 of ROIC 1602. Microlenses 1904 may be diffractive, refractive or a combination of refractive and diffractive by design. It will be understood that detectors configured for detecting other types of radiation besides VNS radiation may be alternately employed in other embodiments (e.g., short wave infrared or mid wave infrared radiation where microbolometer pixel membrane structure 312 is configured to detect LWIR radiation). As shown, each microlens structure 1902 is configured in this exemplary embodiment as concentrator lens having a larger optical area than the underlying optical areas of corresponding opening 310 in reflector metal 318 and detectors 1980.

Still referring to FIGS. 19-22, the pixel-level array of microlens 1904 may be monolithically fabricated over and aligned to the DRC microbolometer pixel membrane structure 312 using any suitable methodology. For example, in a manner similar to that previously described for polarizing and spectral filter embodiments, a second polyimide sacrificial layer (e.g., about 3 microns or any other suitable thickness) may be applied over the DRC pixel array. In this embodiment, interconnects 320 may be made through vias in the second polyimide layer to support the microlens array bridge structure 1902. Since interconnects 320 connect directly to the conductive interconnects 308 that support the first level microbolometer pixel membrane structure 312, the microlens array bridge structure 1902 does not add thermal mass to the microbolometer pixel membrane structure 312.

In one exemplary embodiment, the configuration of FIGS. 19-22 may be implemented to allow simultaneous maximization of both LWIR microbolometer sensitivity and VNS InGaAs-diode sensitivity, for example, in a multispectral pixel design incorporating a LWIR+MWIR amorphous silicon (a-Si) DRC pixel fabricated over a diode imager-based VNS sensing pixel. Such a configuration may be used to simultaneously maximizing sensitivity in both spectral bands by transmitting VNS radiation through the LWIR DRC pixel structure with minimal loss and without corrupting the LWIR resonant cavity absorptance characteristics of the DRC pixel. In one embodiment, ROIC 1602 may employ separate in-pixel integrating amplifiers to integrate the signal from two (e.g., infrared and VNS) spectral bands.

In one exemplary implementation of the embodiment of FIGS. 19-22, a low thermal mass a-Si LWIR DRC pixel design may be implemented that employs a microbolometer pixel membrane structure 312 that includes an infrared absorbing grating structure 1998 (e.g., TiAl structure of about 200 Angstroms or other suitable thickness) that is embedded in a SiN/a-Si/SiN membrane bridge structure 1996 suspended (e.g., at a distance of about 2 microns or other suitable distance) above metal cavity reflector layer 318. In one exemplary embodiment, the membrane 1996 of microbolometer pixel membrane structure 312 may be about 1100 Angstroms thick SiN/a-Si/SiN that is substantially VNS transparent even without openings 310. However, transmittance may be further improved by providing openings 310 to the membrane as well. For example, membrane openings 310 of up to about 2.5 microns×about 2.5 microns may be provided in one exemplary embodiment. However, membrane openings 310 of greater size are also possible, e.g., greater than about 3 microns×about 3 microns, etc.

In one exemplary embodiment, the absorber structure of microbolometer pixel membrane structure 312 may include grating elements of about 1 micron or other suitable width that are spaced on a period of about 5 micron period and exhibit LWIR absorptance (e.g., of greater than about 90%). In such an exemplary configuration, VNS transparent regions 1992 of about 4 microns×4 microns that are free of metal grating elements 1998 permit VNS radiation to efficiently transmit through microbolometer pixel membrane structure 312 in combination with openings 310 of about 2.5 microns by about 2.5 microns. Use of an array of microlens 1904 to focus VNS radiation through VNS transparent regions 1992 may be employed to advantageously maximize transmittance through the DRC microbolometer pixel membrane structure 312.

In one embodiment, cavity reflector metal 318 may be a high reflectivity, low loss aluminum metal layer that exhibits LWIR reflectivity of about 99.9% to ensure high absorptance in the DRC pixel design. In such an embodiment, high reflectivity may be substantially maintained for the cavity reflector 318 by minimizing the size of openings 1960 required to transmit the VNS radiation. This may be advantageously accomplished by providing relatively small openings 1960 (e.g., about 2 microns by about 2 microns) in cavity reflector metal layer 318 to transmit VNS radiation to embedded VNS detector diodes 1980, in combination with leveraging the array of pixel-level microlens 1904 to focus the VNS radiation into each of the relatively small openings 1960.

Figure 21:
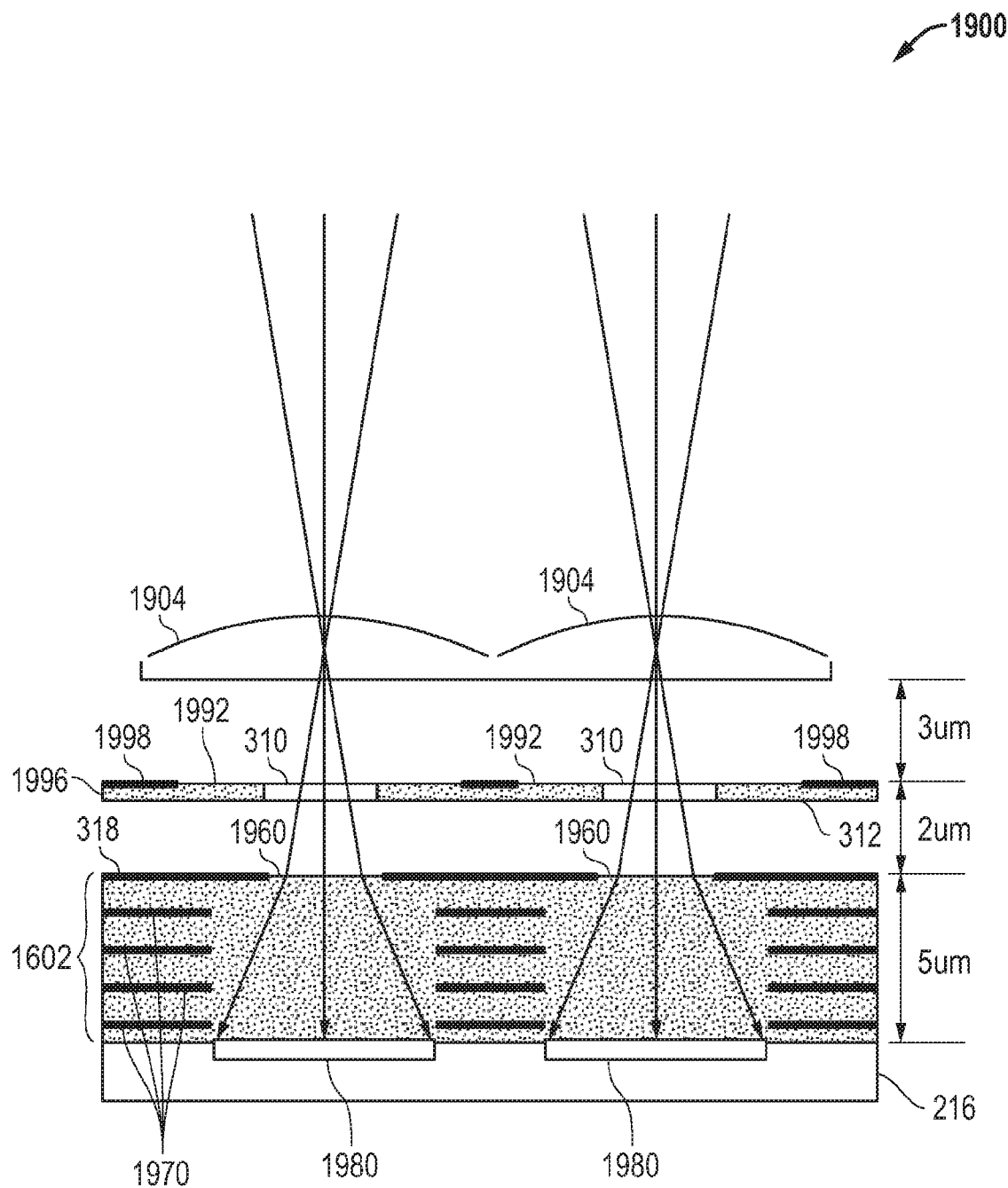
FIG. 21 illustrates a cross sectional view of an uncooled infrared detector element according to one exemplary embodiment of the disclosed apparatus and methods.
Figure 22:
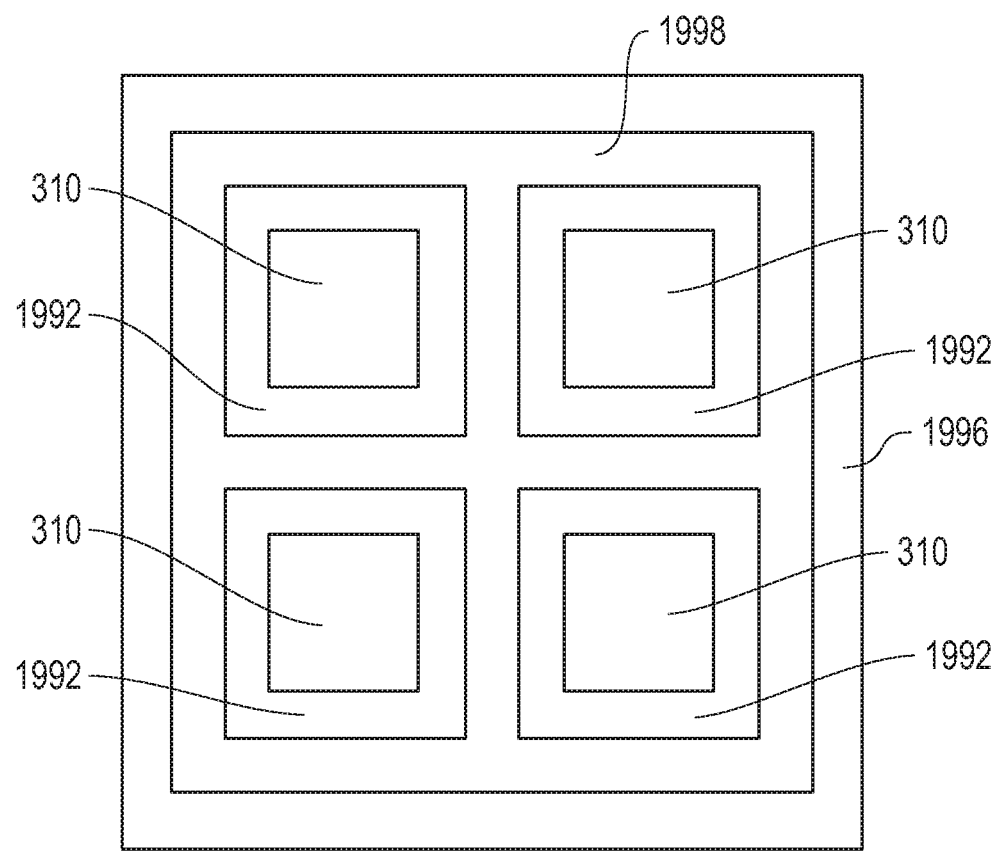
FIG. 22 illustrates a top view of a microbolometer pixel membrane structure according to one exemplary embodiment of the disclosed apparatus and methods.

Referring to FIG. 21 in more detail, an array of ZnSe plano-convex microlenses 1904 may be provided that are configured to focus VNS radiation into individual openings 1960, through which the focused radiation is transmitted through substrate 216 (e.g., $SiO_2$ substrate having a refractive index n of about 1.5) to the embedded VNS detector diodes 1980 as shown.

Table 3 lists one exemplary embodiment of modeled optical characteristics that may be employed for components of detector element 1900 of FIGS. 19-22 when configured in exemplary 17 micron square and 20 micron square bolometer pixel sizes. It will be understood that Table 3 includes modeled and exemplary data only, and that the characteristics of a detector element 1900 may be varied from the data listed.

TABLE 3

| | | |
|---|---|---|
| Bolometer pixel pitch size (microns) | 17 | 20 |
| Field of view; FOV | 20 | 20 |
| Plano-convex optic diameter D (microns) | 8.5 | 10 |
| Distance from optic to aperture $l_1$ (microns) | 5 | 5 |
| Effective f-number (f/#) | 0.59 | 0.50 |
| Refractive index for ZnSe; $n_{ZnSe}$ | 2.7 | 2.7 |
| Effective Focal length (EFL) (microns) = $l_1$ | 5 | 5 |
| Approximate plano-convex lens radius of curvature R = EFL * $(n_{ZnSe} - 1)$ | 8.5 | 8.5 |
| Approximate minimum lens thickness (microns) = R − $\sqrt{R^2 - (D/2)^2}$ | 1.14 | 1.63 |
| ZnSe thickness (microns) for anti reflection condition at 10 microns: $\lambda/2n_{ZnSe}$ | 1.85 | 1.85 |
| Reflector Metal Aperture size A (microns) = 2 * $l_1$ * sin(FOV/2) | 1.74 | 1.74 |
| Cavity spacing between DRC membrane and reflector metal (microns) | 2 | 2 |
| Opening size in DRC membrane (microns) | 3.4 | 4.0 |
| Distance from aperture to Ge diode $l_2$ (microns) | 5 | 5 |

TABLE 3-continued

| | | |
|---|---|---|
| Oxide refractive index $n_{oxide}$ | 1.5 | 1.5 |
| Size of Ge diode = $2 * (l_2 * n + l_1) * \sin(FOV/2)$ | 4.34 | 4.34 |

Figure 23:
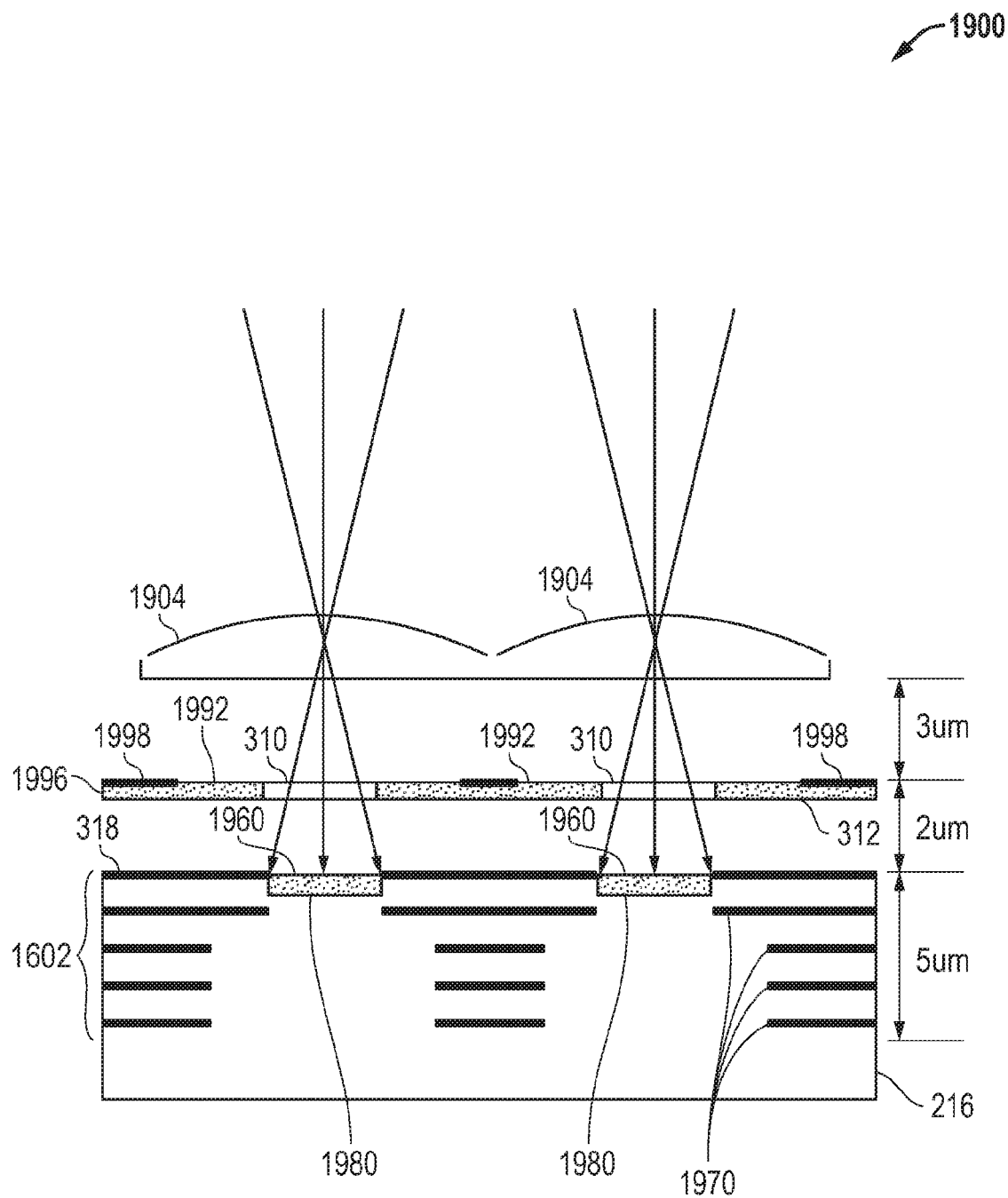
FIG. 23 illustrates a cross sectional view of an uncooled infrared detector element according to one exemplary embodiment of the disclosed apparatus and methods.

FIG. 23 illustrates an alternative exemplary embodiment of a dual band detector element 1900 configured similar to the embodiment of FIG. 21, except that VNS diode (e.g., InGaAs) detectors 1980 are provided (e.g., bonded or otherwise attached) at the top of substrate 216 immediately below openings 1960 in reflector metal 318. In this exemplary embodiment, an array of ZnSe plano-convex microlenses 1904 may be provided that are configured to focus VNS radiation onto VNS detector diodes 1980 positioned at individual openings 1960 as shown.

The integrated LWIR/VNS pixel design of the embodiments of FIGS. 19-23 may be advantageously optimized in one embodiment to achieve VNS radiation transmission through the LWIR bolometer of greater than about 80% while maintaining high LWIR infrared absorptance. Inclusion of the pixel-level microlens 1904 may be employed to provide an additional mechanism to focus the VNS radiation through the DRC pixel onto the VNS radiation detectors 1980. Although the configuration of microlens 1904 is depicted as a refractive optical element, any other suitable focusing optical design configuration (e.g., broadband diffractive or diffractive/refractive optic design fabricated by gray scale lithography) may be employed.

Focal plane arrays may be manufactured using any suitable or desired number of detector elements, and/or sizes of detector elements. Example focal plane array configurations include, but are not limited to, 17 micron square detector element pixels configured in pixel array sizes of 320×240, 640×480, 1024×768, etc. In one exemplary embodiment, 17 micron square detectors element pixels may configured in a 640×480 pixel array having f/1 noise equivalent temperature difference $(NETD)_{8-12um}$ of about 40 mK and a thermal time constant of about 10 milliseconds using low noise a-Si material with thermal coefficient of resistance (TCR) of about 3.1%/K. In one exemplary embodiment, microlenses 1904 employ a VNS antireflection coating.

It will be understood that the dual band detector element configurations of FIGS. 19-23 are exemplary only. In this regard, a microlens or microlens array optical element may be suspended over and above the membrane material of a microbolometer pixel membrane structure of a single band uncooled infrared detector element or a multi-band detector capable of detecting radiation in three or more different radiation bands (e.g., a microlens or microlens array optical element may be suspended over and above the membrane material of an upper microbolometer pixel membrane structure of a multi-band detector having two or more stacked microbolometer pixel membrane structures having aligned openings therein for transmitting radiation from the uppermost microbolometer pixel membrane structure to a substrate underlying the lowermost microbolometer pixel membrane structure).

Figure 24:
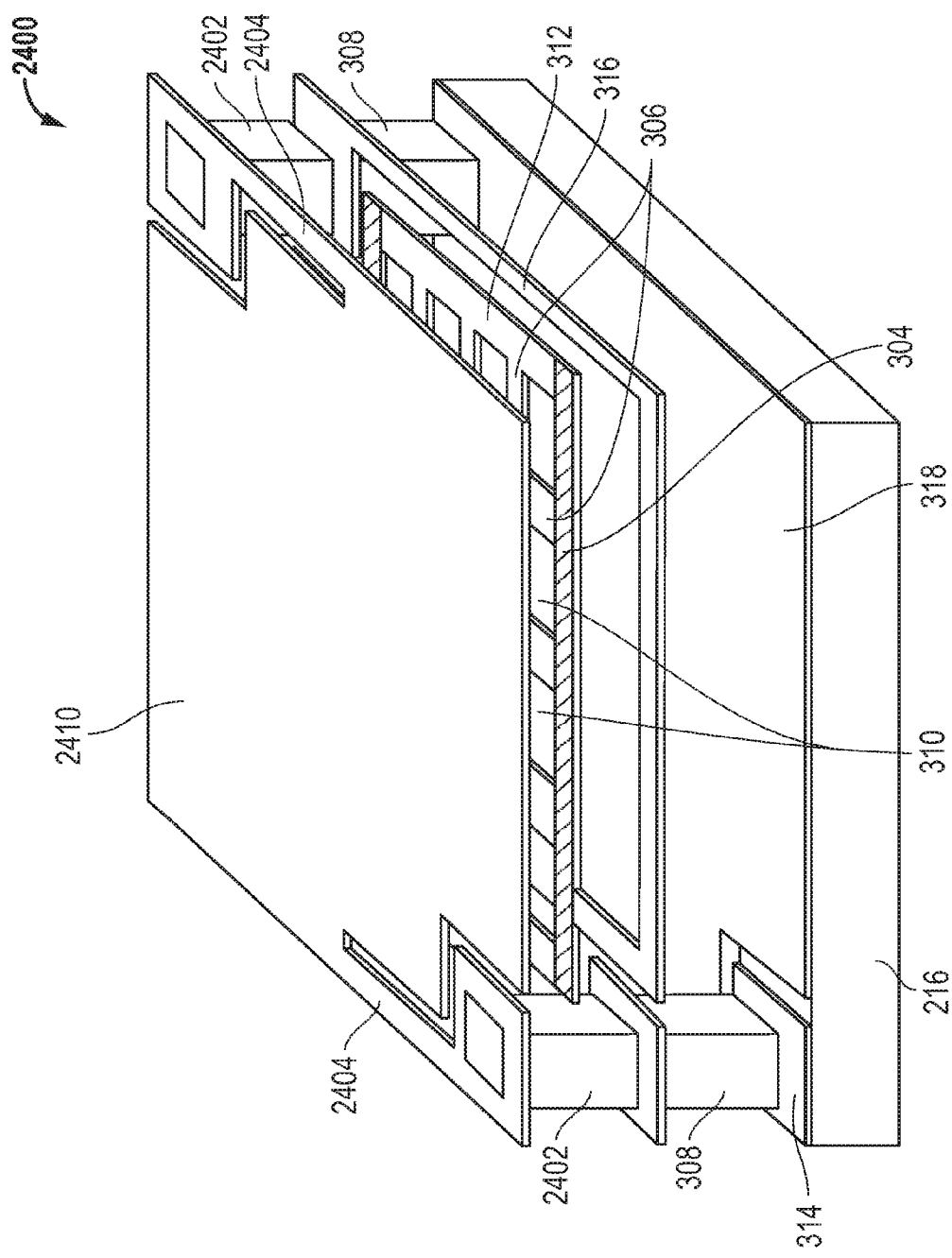
FIG. 24 illustrates a perspective view of an uncooled infrared detector element according to one exemplary embodiment of the disclosed apparatus and methods.

FIG. 24 illustrates one exemplary embodiment of an uncooled infrared detector element 2400 that includes an optically transitioning (e.g., thermochromic or phase transitioning) filter element 2410 suspended by two optically transitioning filter element support interconnects 2402 (e.g., at a distance of about 1 to 2 microns or other suitable distance) over and above a microbolometer pixel membrane structure 312 and associated silicon semiconductor substrate 216 and optional reflector 318 of the same type described in relation to FIG. 3. In this regard, microbolometer pixel membrane structure 312 may be itself suspended (e.g., at a distance of about 2 microns) above silicon semiconductor substrate 216 by relatively long thermal isolation legs 316 that are electrically connected to the ROIC of the semiconductor substrate 216 by the metal interconnects 308 via conductive input pads 314. As with the embodiment of FIG. 3, a microbolometer pixel membrane structure 312 may be suspended greater than or less than about 2 microns above silicon semiconductor substrate 216 in other embodiments. It will be understood that the disclosed pixel-level optically transitioning filter elements may be suspended or otherwise operatively disposed above a variety of types of detector elements including, but not limited to, infrared microbolometer pixel membrane, CCD detector pixel, millimeter wave detector pixel, CMOS detector pixel, etc. Further, as previously indicated herein, a separate optically transitioning filter element may be monolithically fabricated with a corresponding underlying detector pixel in a manner as previously described for other embodiments herein, or may be separately fabricated and then attached or otherwise assembled over a corresponding individual detector element.

In the exemplary embodiment of FIG. 24, optically transitioning filter element 2410 may be composed of one or more optically transitioning materials suitable for the filtering requirements of a given application, e.g., selected to filter out undesired wavelengths at a given selected temperature. Examples of such materials include, but are not limited to, thermochromic or phase transitioning compositions of germanium-antimony-tellurium (GST or $Ge_xSb_yTe_z$), vanadium oxide (VO, $VO_2$, $V_nO_{2n-1}$ such as $V_2O_3$), tungsten-doped vanadium oxide (W:$VO_X$ such as W:$VO_2$, and stoichiometric variants), niobium oxide, tantalum oxide, $Ti_2O_3$, $Fe_3O_4$, $Mo_9O_{26}$, etc.). Such optically transitioning materials act to selectively transmit radiation depending on the temperature of the material, e.g., vanadium dioxide ($VO_2$) remains an optically transmissive semiconductor to infrared radiation below about 68° C. or below and becomes an optically opaque metallic material to infrared radiation at temperatures greater than or equal to about 68° C. In one particular exemplary embodiment, vanadium oxide having the formula $V_nO_{2n-1}$ may be employed as an optically transitioning material for selectively filtering infrared radiation, where n has a value of from 1 to 5. In any case, it will be understood that composition/s of an optically transitioning material may be chosen that optically transition to selectively filter out those particular radiation wavelengths (e.g., including non-infrared radiation wavelengths) that meet the needs of a given application.

Further, as described elsewhere herein, composition of optically transitioning materials may be varied (e.g., by doping with other materials such as tungsten, aluminum and/or manganese) to tailor the optical transition (e.g., phase transition) characteristics of the material as a function of temperature for different applications. For example, in one exemplary embodiment, thermochromic vanadium oxide (e.g., $VO_2$) may be doped with from about 1% to about 1.9% tungsten to lower the transition temperature, although other amounts and/or types of dopants may be employed. Thus, an optically transitioning material may be selected based on its optical transition properties, and/or its optical transition properties may be tailored by doping, to configure an optically transitioning filter that minimizes parasitic effects while filtering out any undesired radiation wavelengths at higher temperatures without substantially absorbing radiation wavelengths of interest at lower temperatures.

Table 4 illustrates exemplary dimensions for one possible embodiment of an optically transitioning filtered detector embodiment 2400 using the material layer sequence 1600 of FIG. 16, which was previously described in relation to spectral filter layers, it being understood that a variety of other configurations may be specified as needed to meet different applications. In this regard, it will be understood that in other embodiments, optically transitioning filter element 2410 may be configured with different materials, and greater or lesser thicknesses. Likewise, it will be understood that thermal isolation legs 2404 may be configured with any dimensions and/or geometry suitable for supporting and contributing to thermal isolation of optically transitioning filter element 2410.

TABLE 4

Optically Transitioning Filter Layer Structure

| Layer | Material | Layer Thickness (micrometers) |
|---|---|---|
| 1318 | Aluminum | 0.25 |
| 1606 | Vacuum Cavity | 2.15 |
| 1608 | Silicon Nitride | 0.03 |
| 1610 | Silicon | 0.065 |
| 1612 | Silicon Nitride | 0.04 |
| 1614 | Titanium | 0.025 |
| 1616 | Silicon Nitride | 0.05 |
| 1618 | Vacuum Cavity | 0.8 |
| 1620 | Silicon Nitride | 0.03 |
| 1622 | VO$_2$ | 0.2 |
| 1624 | Silicon Nitride | 0.03 |

Figure 18B:
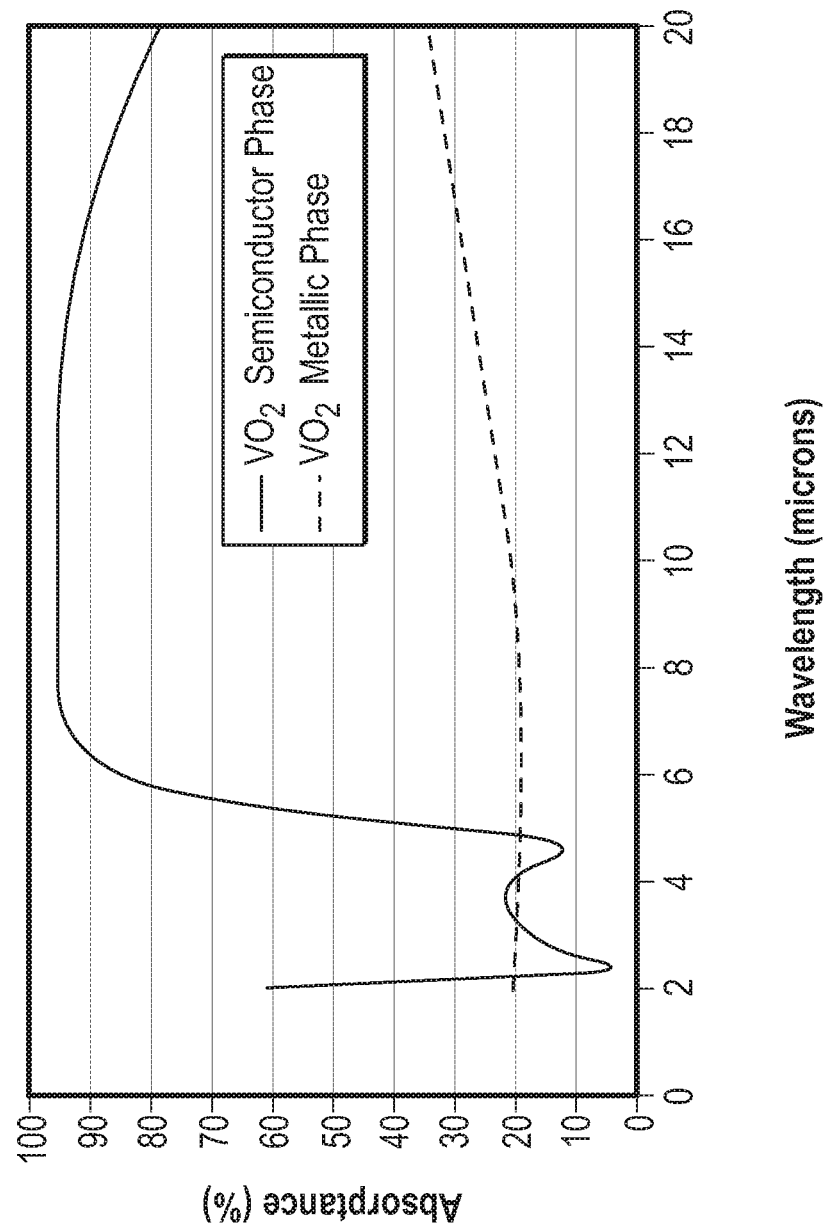
FIG. 18B illustrates absorptance versus wavelength according to one exemplary embodiment of the disclosed apparatus and methods.
Figure 19:
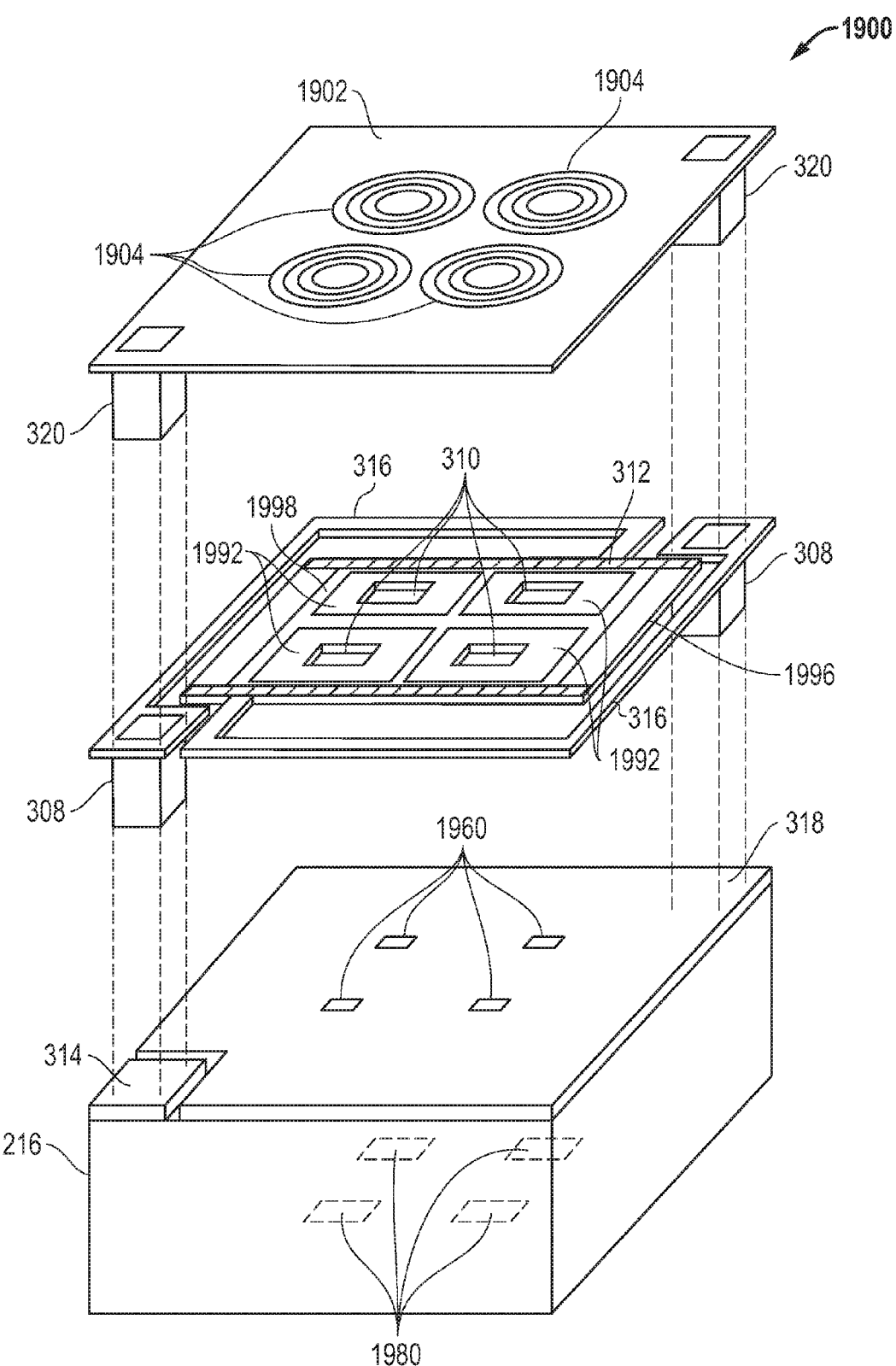
FIG. 19 illustrates an exploded perspective view of an uncooled infrared detector element according to one exemplary embodiment of the disclosed apparatus and methods.
Figure 20:
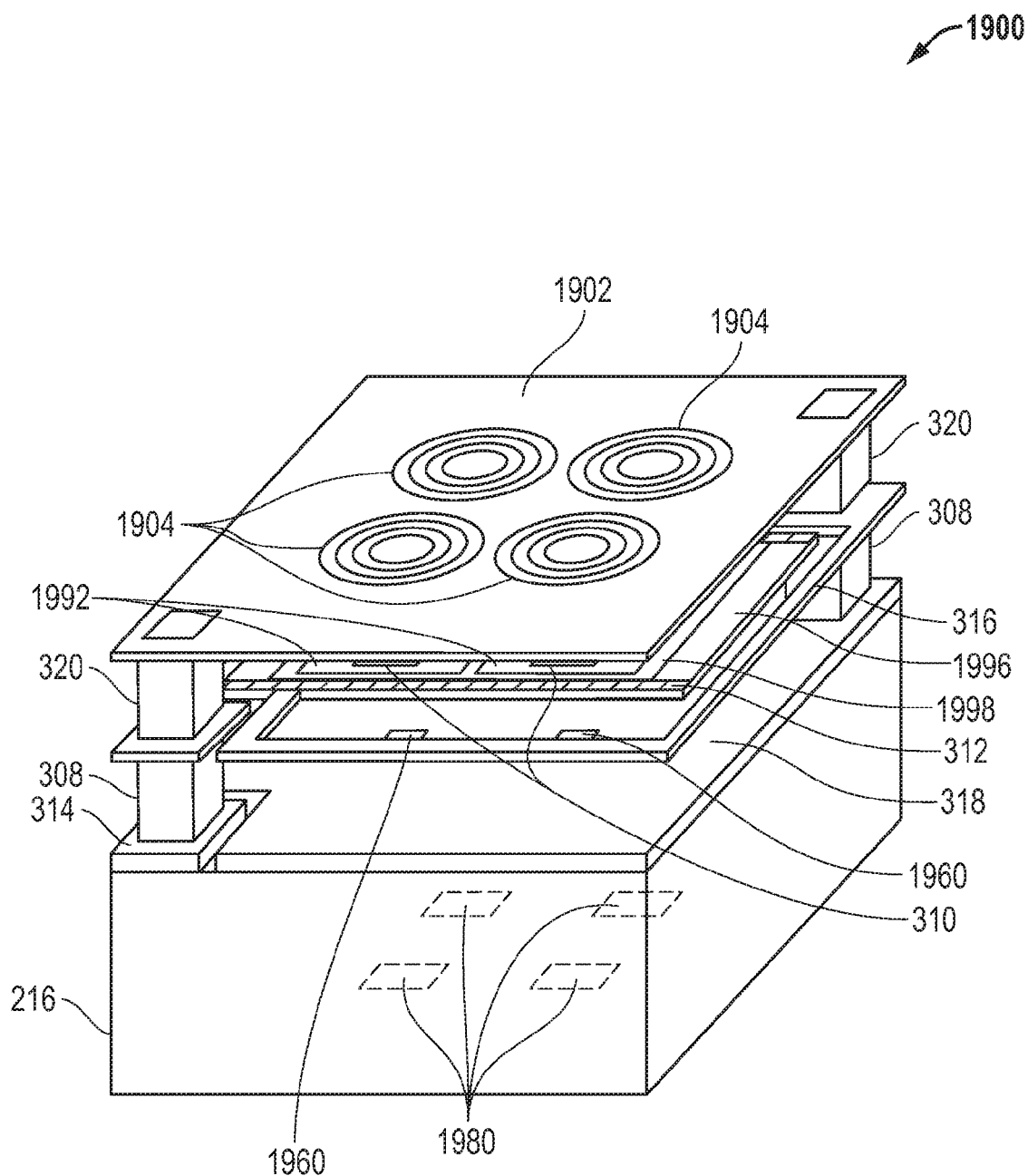
FIG. 20 illustrates a perspective view of an uncooled infrared detector element according to one exemplary embodiment of the disclosed apparatus and methods.

FIG. 18B illustrates spectral response in terms of detector absorptance versus wavelength for the amorphous-silicon two-level detector embodiment according to the optically transitioning filtered layer structure of Table 4. It will be understood that the layer structure embodiments of Table 4 is exemplary only, and that other materials, layer configurations and layer thicknesses may be employed as suitable or desired for the given application.

For example, solar radiation consists more predominantly of mid wave IR radiation (from about 3 to about 5 microns) than long wave IR radiation (from about 8 to about 14 microns). Therefore, an infrared detector may be configured with an optically transitioning material (e.g., tungsten-doped vanadium oxide (W:VO$_x$, and stoichiometric variants) that absorbs mid wave IR radiation, but that is substantially transmissive to long wave IR radiation. Therefore, the selected optically transitioning material of the filter element passes the desired radiation waveband (long wave IR) to the underlying detector element without substantial heating and while remaining transmissive and below its optical transition temperature. However, upon exposure to the undesired waveband (mid wave solar radiation) the selected optically transitioning material of the filter element absorbs the undesired radiation and heats up to above its transition temperature, at which point it becomes opaque and substantially shields the underlying detector element from mid wave IR radiation.

Besides the selection of optically transitioning materials, other design factors that may be varied to tune or otherwise control the filtering characteristics of an optically transitioning filter element include, but are not limited to, 1) optically transitioning filter element thickness to define radiation wavelengths to which the optically transitioning filter responds, 2) thermal isolation of the optically transitioning filter element from the surrounding environment and underlying components of the detector element to control the exposure of the microbolometer to radiation at a given spectrum, and 3) optically transitioning filter element size (surface area) relative to size (surface area) of the underlying microbolometer pixel membrane structure 312 or other pixel detector element component/s to control fraction (percentage) of incoming undesired radiation that is absorbed by the underlying microbolometer. In this regard, optically transitioning filter element thickness and thermal isolation may be selected to tune performance of the optically transitioning filter element such that it becomes non-transmissive to undesired radiation before an unacceptable amount of the undesired radiation has an opportunity to pass through to the underlying detector element components.

In the embodiment of FIG. 24, optically transitioning filter element support interconnects 2402 are composed of material that is both electrically and thermally insulating (e.g., such as silicon nitride (SiN) or other electrically and thermally insulating material), and may be configured with similar dimensions as previously described for optical element support interconnects 320 in relation to FIG. 3. As shown, optically transitioning filter element support interconnects 2402 may be disposed on electrically conductive interconnects 308 (e.g., TiW) as shown to minimize any addition to the pixel thermal mass or change to the pixel time constant. Similar to other interconnect structures described herein, optical support interconnects 2402 may be configured as hollow tubular structures (e.g., cylindrical, square, etc.), although solid interconnects or interconnects having greater or less wall thicknesses may be alternately employed. Configuring optically transitioning filter element support interconnects 2402 to be thermally insulating helps to thermally isolate optically transitioning filter element 2410 from the other underlying components of infrared detector element 2400, thus allowing optically transitioning filter element 2410 to retain heat absorbed from incoming radiation such that the temperature of optically transitioning filter element 2410 increases from a temperature below its optical transition (e.g., phase transition) temperature to a temperature above its optical transition (e.g., phase transition) temperature upon exposure to such radiation. In one exemplary embodiment, optically transitioning filter element support interconnects 2402 may be optionally composed of the same material as optically transitioning filter element 2410 (e.g., vanadium oxide and stoichiometric variants or other suitable optically transitioning material), for example, as a downwardly-protruding extension of optically transitioning filter element 2410.

To further increase its thermal isolation, optically transitioning filter element 2410 may be configured with optional thermal isolation legs 2404 defined in the optically transitioning material of filter element 2410 to extend from optically transitioning filter element support interconnects 2402 to support the main body of optically transitioning filter element 2410 as shown. The length and cross sectional area of legs 2404 determines the filter's response to IR flux.

Figure 25:
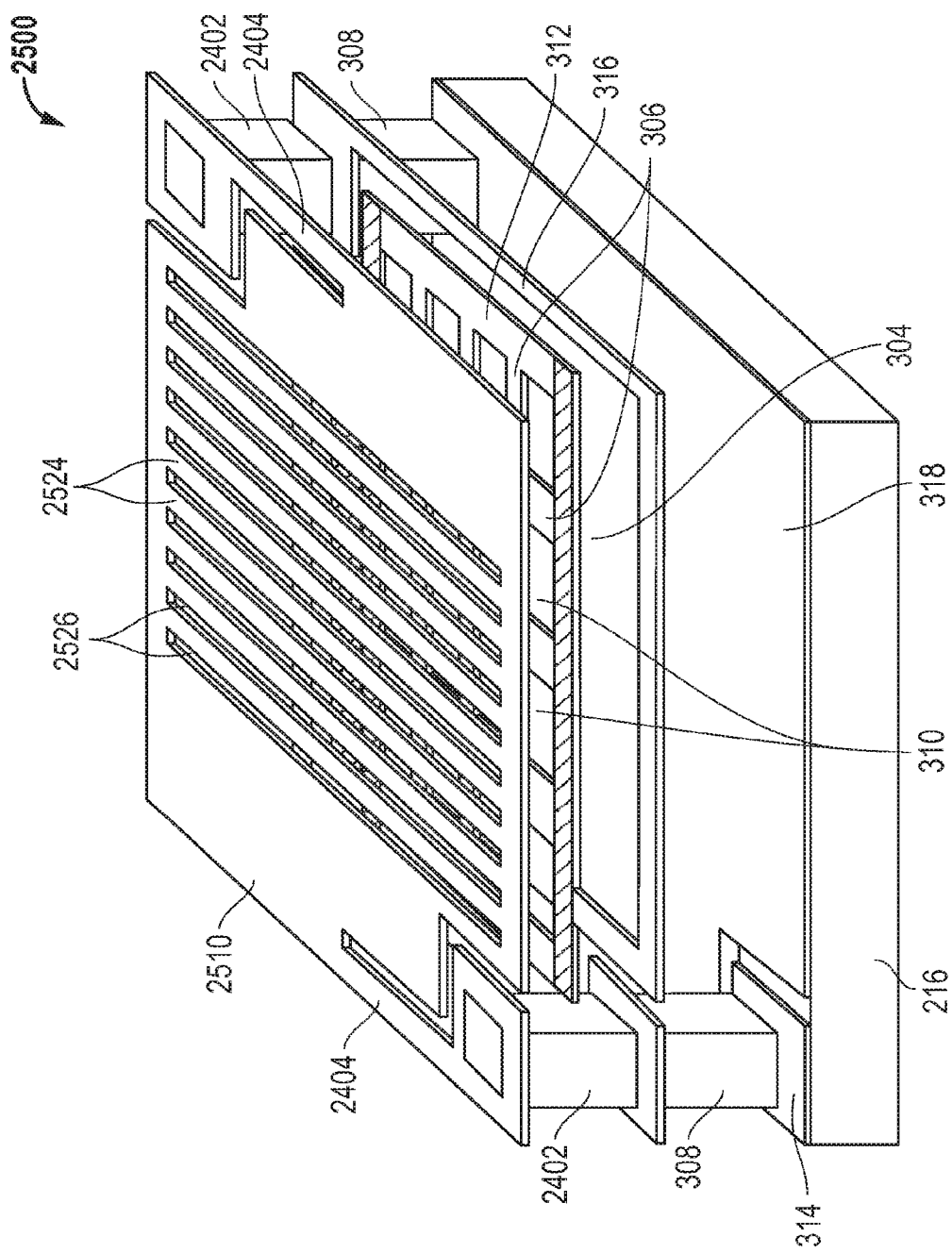
FIG. 25 illustrates a perspective view of an uncooled infrared detector element according to one exemplary embodiment of the disclosed apparatus and methods.

FIG. 25 illustrates one exemplary embodiment of an uncooled infrared detector element 2500 that includes an optically transitioning (e.g., thermochromic or phase transitioning) polarizer filter element 2510 that is formed and suspended (e.g., at a distance of about 1 to 2 microns or other suitable distance) by two electrically and thermally insulating optically transitioning filter element support interconnects 2402 over and above a microbolometer pixel membrane structure 312 and associated silicon semiconductor substrate 216 and optional reflector 318 in a manner similar to that described in relation to FIG. 24. Polarizer filter element 2510 may be of any patternable optically transitioning material, e.g., of a thickness and type/s described in relation to the embodiment of FIG. 24. As shown, monolithic polarizer filter may be patterned in a manner similar to that described in relation to the embodiment of FIG. 3 into a linear diffraction grating (e.g., of varying possible periods and orientations) that includes elongated grating elements (wires) 2424 that are separated by elongated spaces 2526. As with the embodiment of FIG. 3, dimensions of such a diffraction grating or other polarizer filter design may vary according to the desired filtering characteristics to be imparted by polarizer filter element 2510, and grating element width and period may be selected and varied to achieve desired filter effects based on factors such as spectrum or spectra to be filtered, required polarizer efficiency, etc.

Figure 26:
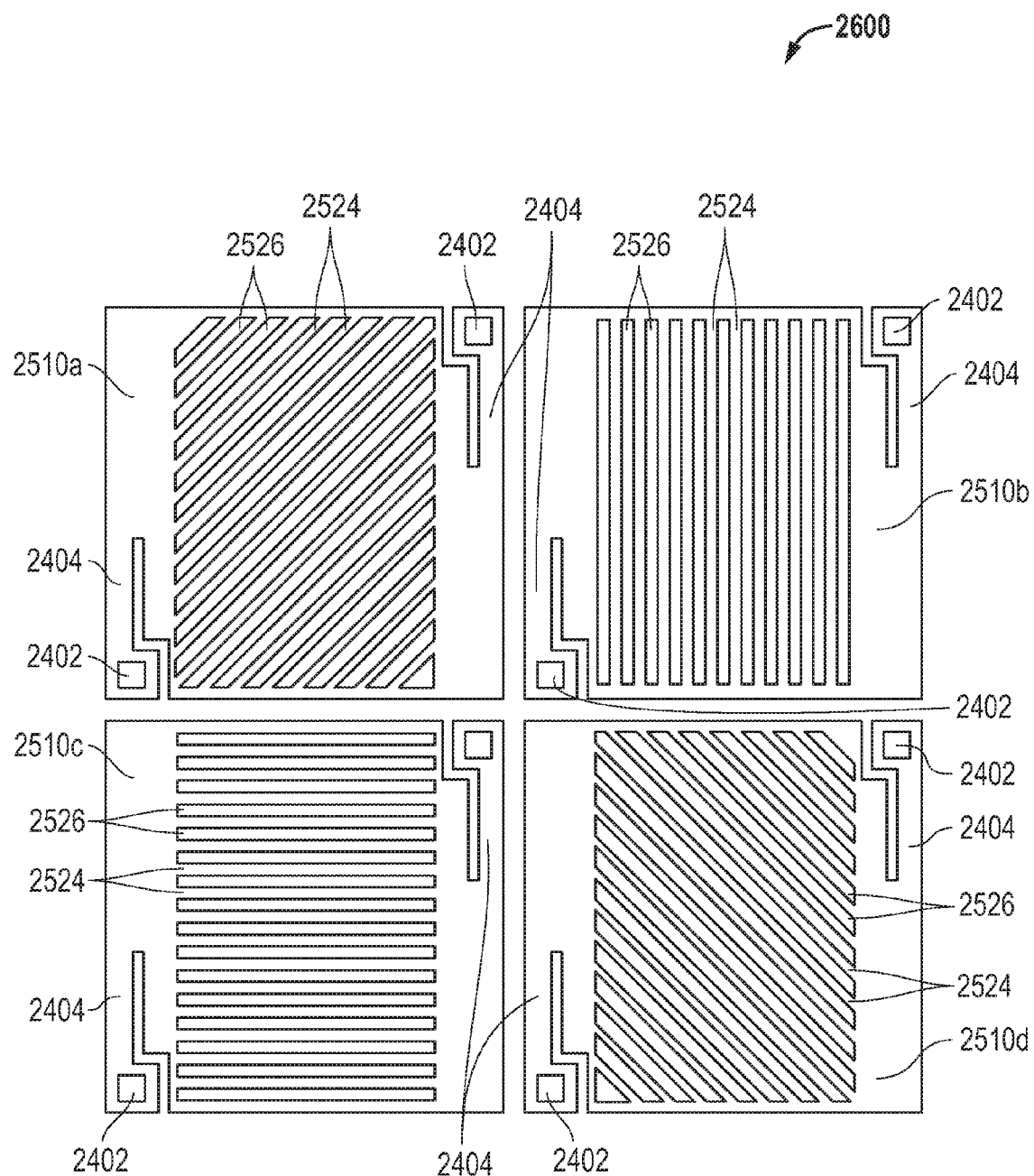
FIG. 26 illustrates a top view of a subarray according to one exemplary embodiment of the disclosed apparatus and methods.

In a manner similar to that described in relation to FIG. 4, adjacent uncooled infrared detector elements 2500 of a focal plane array may be provided with differently-configured optically transitioning polarization filter elements 2510, e.g., so that adjacent infrared detector element pixels 2400 absorb different polarization components of the scene infrared radiation. For example, FIG. 26 illustrates a top view of one exemplary embodiment of a 2×2 subarray 2600 of four adjacent optically transitioning polarization filter elements 2510a-2510d. Subarray 2600 may form a part of a larger FPA 212, e.g., such as a 30 micron pixel 320×240 amorphous silicon microbolometer FPA 212. In FIG. 26, 2×2 subarray 2600 includes polarizer filter structures 2510a-2510d in place overlying corresponding microbolometer pixel membrane structures 312a-312d of 2×2 subarray 400 of FIG. 4.

As shown in FIG. 26, the polarizer filter structures include horizontal monolithic grating structure 2510c, +45° monolithic grating structure 2510a, −45° monolithic grating structure 2510d, and vertical monolithic grating structure 2510b. In the illustrated embodiment of FIG. 26, four polarizations (corresponding to four Stokes vectors) are included in 2×2 subarray 2600. However, it will be understood that the embodiment of FIG. 26 is exemplary only, and that any other combination of two or more differently-configured monolithic polarization filter elements 2510 may be employed in the same FPA 212, in a regular or irregular pattern, or in a random arrangement (e.g., in a larger pattern such as previously described and illustrated in relation to FIG. 6). As previously described in relation to the embodiment of FIG. 7, one or more microbolometer pixel membrane structures 312 of a focal plane array 212 may be left uncovered with no overlying polarizer filter structure 2510.

Figure 27:
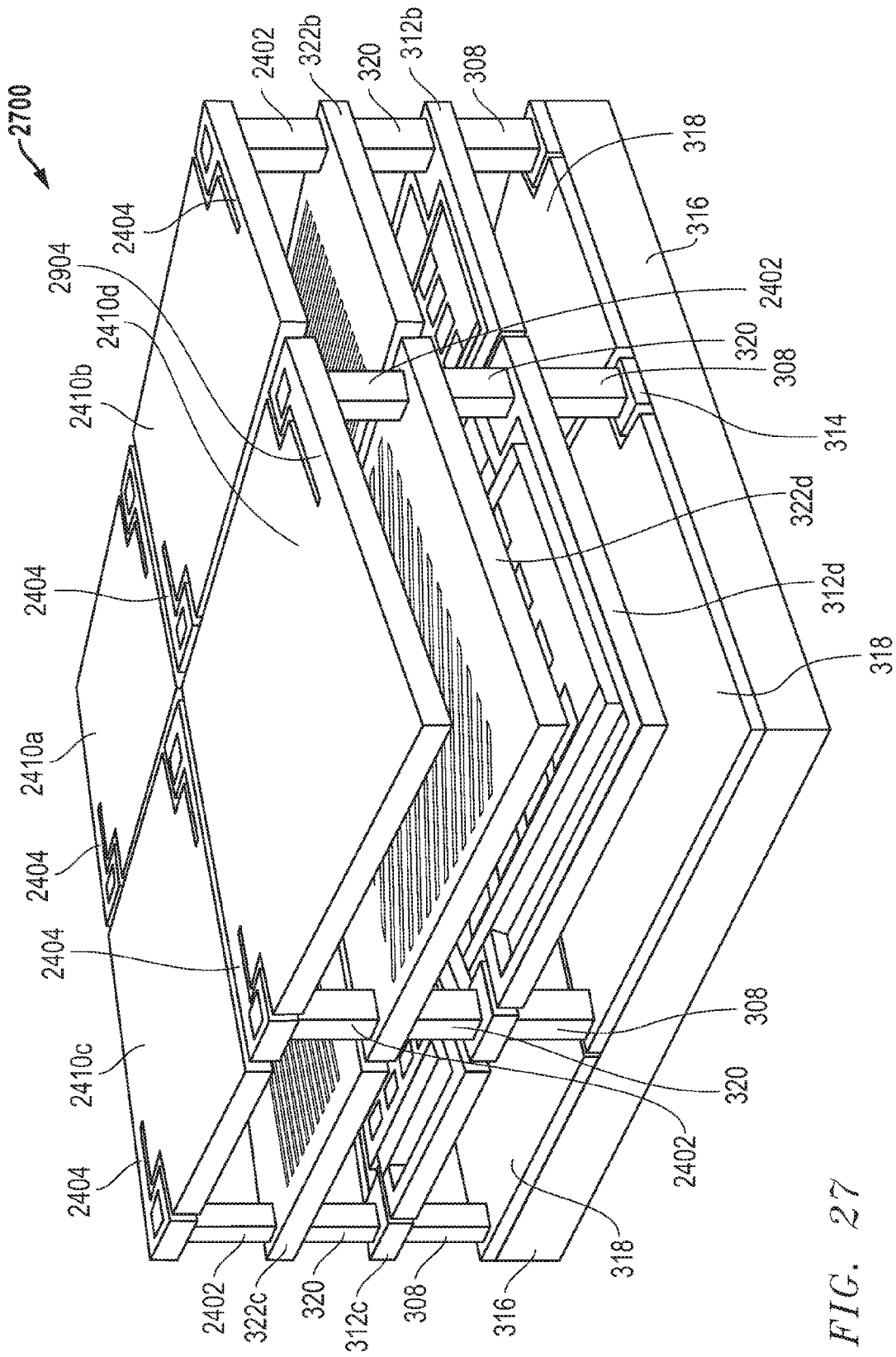
FIG. 27 illustrates a perspective view of a subarray according to one exemplary embodiment of the disclosed apparatus and methods.

It will be understood that optical elements of one type may be combined or stacked with one or more other types of optical elements above an underlying detector element, such as a microbolometer pixel membrane structure 312. For example, optically transitioning filter elements may be stacked or combined with other types of optical elements such as polarizing filter elements 322 and/or spectral filter elements 1222. In this regard, FIG. 27 illustrates a perspective view of a 2×2 subarray 2700 of four adjacent IR detector elements that each include a respective optically transitioning (e.g., thermochromic or phase transitioning) filter element 2410a-2410d suspended by two electrically and thermally insulating optically transitioning filter element support interconnects 2402 (e.g., at a distance of about 1 to 2 microns or other suitable distance) over and above a respective polarizer filter 322a-322d that itself is in turn suspended at a distance of from about 1 micron to about 2 microns over and above a respective microbolometer pixel membrane structure 312a-312d by two optical element support interconnects 320 that each extend down and are substantially aligned to and supported by the top of respective thermally and electrically conductive interconnects 308 of the respective microbolometer pixel structure 312a-312d. As shown in FIG. 27, optically transitioning filter element support interconnects 2402 extend down and are substantially aligned to and supported by the top of respective optical element support interconnects 320.

Figure 28:
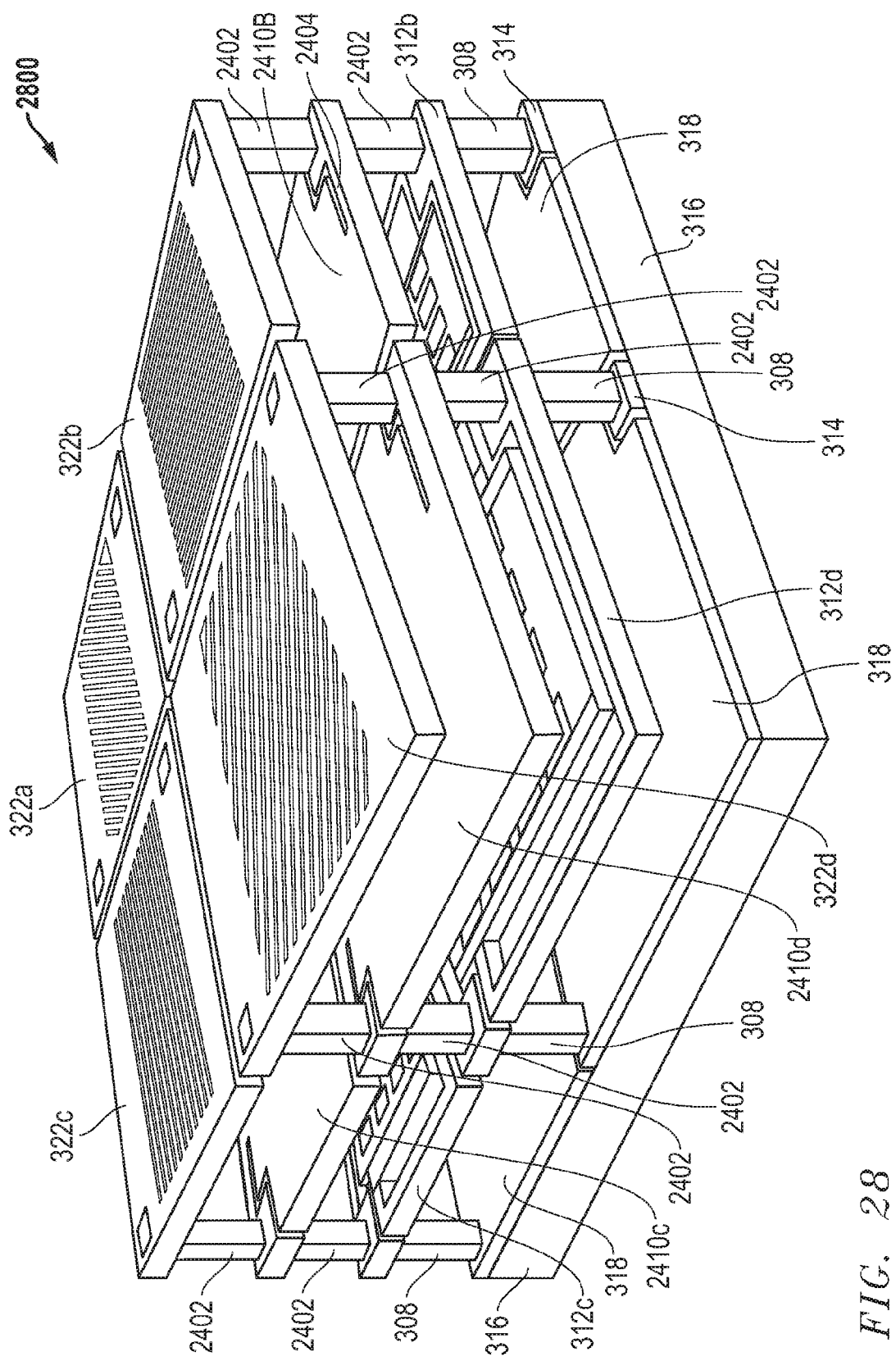
FIG. 28 illustrates a perspective view of a subarray according to one exemplary embodiment of the disclosed apparatus and methods.

FIG. 28 illustrates a perspective view of another exemplary embodiment of a 2×2 subarray 2800 of four adjacent IR detector elements that each include a respective polarizer filter 322a-322d suspended by two optically transitioning filter element support interconnects 2402 (e.g., at a distance of about 1 to 2 microns or other suitable distance) over and above a respective optically transitioning (e.g., thermochromic or phase transitioning) filter element 2410a-2410d that itself is in turn suspended at a distance of from about 1 micron to about 2 microns over and above a respective microbolometer pixel membrane structure 312a-312d by two optically transitioning filter element support interconnects 2402 that each extend down and are substantially aligned to and supported by the top of respective thermally and electrically conductive interconnects 308 of the respective microbolometer pixel structure 312a-312d. As shown in FIG. 27, optically transitioning filter element support interconnects 2402 extend down and are substantially aligned to and supported by the top of respective optical element support interconnects 320. It is noted that electrically and thermally insulating optically transitioning filter element support interconnects 2402 may be configured in this embodiment to support both polarizer filters 322a-322d and optically transitioning filter elements 2410a-2410d in order to provide thermal isolation for each of optically transitioning filter elements 2410a-2410d.

It will be understood that the particular configurations of the embodiments of FIGS. 27 and 28 are exemplary only, and that any other suitable combination of materials, structural configurations, dimensions, optical element types, etc. may be employed. For example, more than one optical element or other types of separate pixel-level optical elements (e.g., a separate spectral filter element) may be suspended in the radiation path between an optically transitioning filter element 2410 and a microbolometer pixel membrane structure 312 or other type of radiation detector circuitry. Likewise, more than one pixel-level optical element or other types of separate optical elements (e.g., a separate spectral filter element) may be suspended over and above an optically transitioning filter element 2410 that is in turn suspended over and above a microbolometer pixel membrane structure 312 or other type of radiation detector circuitry. Optically transitioning filter elements are also discussed in concurrently filed patent application Ser. No. 12/799,629, now U.S. Pat. No. 8,227,755, entitled "PIXEL-LEVEL OPTICALLY TRANSITIONING FILTER ELEMENTS FOR DETECTOR DEVICES" by Fagan III et al., which is incorporated herein by reference in its entirety.

Figure 29:
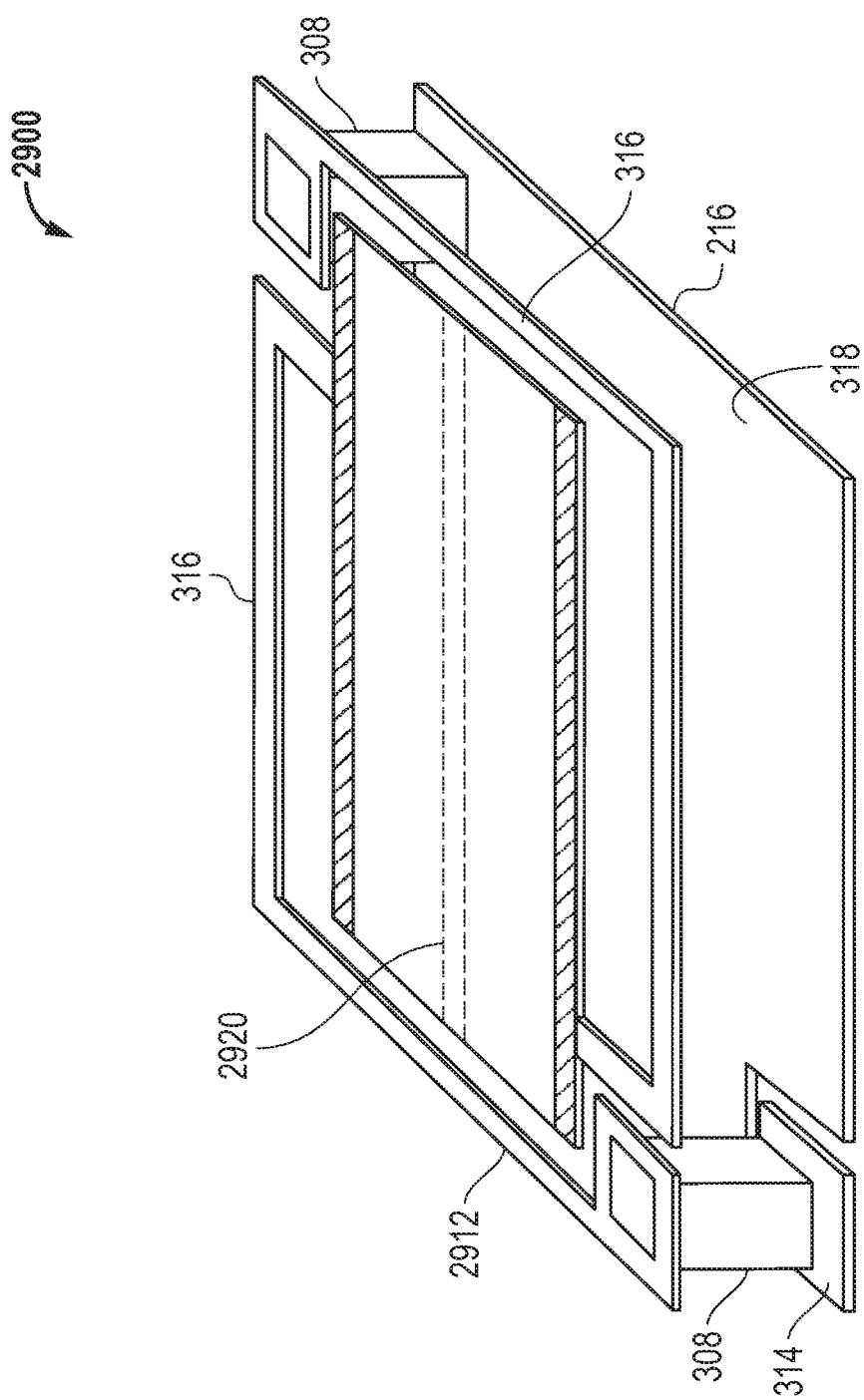
FIG. 29 illustrates a perspective view of an uncooled infrared detector element according to one embodiment of the disclosed apparatus and methods.

FIG. 29 illustrates a perspective view of an uncooled infrared detector element 2900 according to another exemplary embodiment of the disclosed apparatus and methods. In this embodiment, uncooled infrared detector element 2900 includes an optically transitioning microbolometer pixel membrane structure 2912 that includes thin (e.g., from about 1000 Angstroms to about 4000 Angstroms thick) thermally sensitive membrane material of a resistive material like amorphous silicon (a-Si); amorphous silicon geranium (a-SiGe); or Vanadium Oxide (VOx) together with infrared absorbing material that includes one or more optically transitioning materials (e.g., thermochromic or phase transitioning compositions of germanium-antimony-tellurium (GST or $Ge_xSb_yTe_z$), vanadium oxide (VO, $VO_2$, $V_nO_{2n-1}$ such as $V_2O_3$), tungsten-doped vanadium oxide (W:$VO_x$ such as W:$VO_2$, and stoichiometric variants), niobium oxide, tantalum oxide, $Ti_2O_3$, $Fe_3O_4$, $Mo_9O_{26}$, etc.)) that act to selectively transmit radiation depending on temperature. As described elsewhere herein, composition of such materials may be varied (e.g., by doping with other materials such as tungsten, aluminum and/or manganese) to tailor the optical transition (e.g., phase transition) characteristics of the material as a function of temperature.

In one exemplary embodiment, the microbolometer pixel membrane structure 2912 of infrared detector element 2900 may be suspended about 2 microns above silicon semiconductor substrate 216 by relatively long thermal isolation legs 316 that are electrically connected to the ROIC within semiconductor substrate 216 by the metal interconnects 308 via conductive input pads 314, although a microbolometer pixel membrane structure 2912 may be suspended greater than or less than about 2 microns above silicon semiconductor substrate 216 in other embodiments. It will be understood that a plurality of infrared detector elements 2900 may be employed in a manner similar to infrared detector elements 300 to form a focal plane array 212 such as illustrated and described in relation to FIG. 2.

Still referring to FIG. 29, a metal reflector 318 (e.g., aluminum, etc.) for reflecting IR radiation may be optionally disposed as shown on the surface of the supporting substrate 216 and ROIC to form a resonant cavity structure to enhance infrared absorptance in the membrane of the suspended microbolometer pixel structure 2912. In one exemplary embodiment, pixel geometry may be square-shaped and the pixel area may range from about 12 um×12 um to about 100 um×100 um, although pixel shapes other than square and/or pixel sizes smaller than 12 um×12 um or greater than 100 um×100 um may be employed in other embodiments. Although no material has been removed from the membrane material of suspended microbolometer pixel membrane structure 2912, it will be understood that a microbolometer pixel structure having a DRC configuration (e.g., such as illustrated in FIG. 3) may be similarly provided with an optically transitioning (e.g., thermochromic or phase transitioning) thermally absorbing material.

Figure 30:
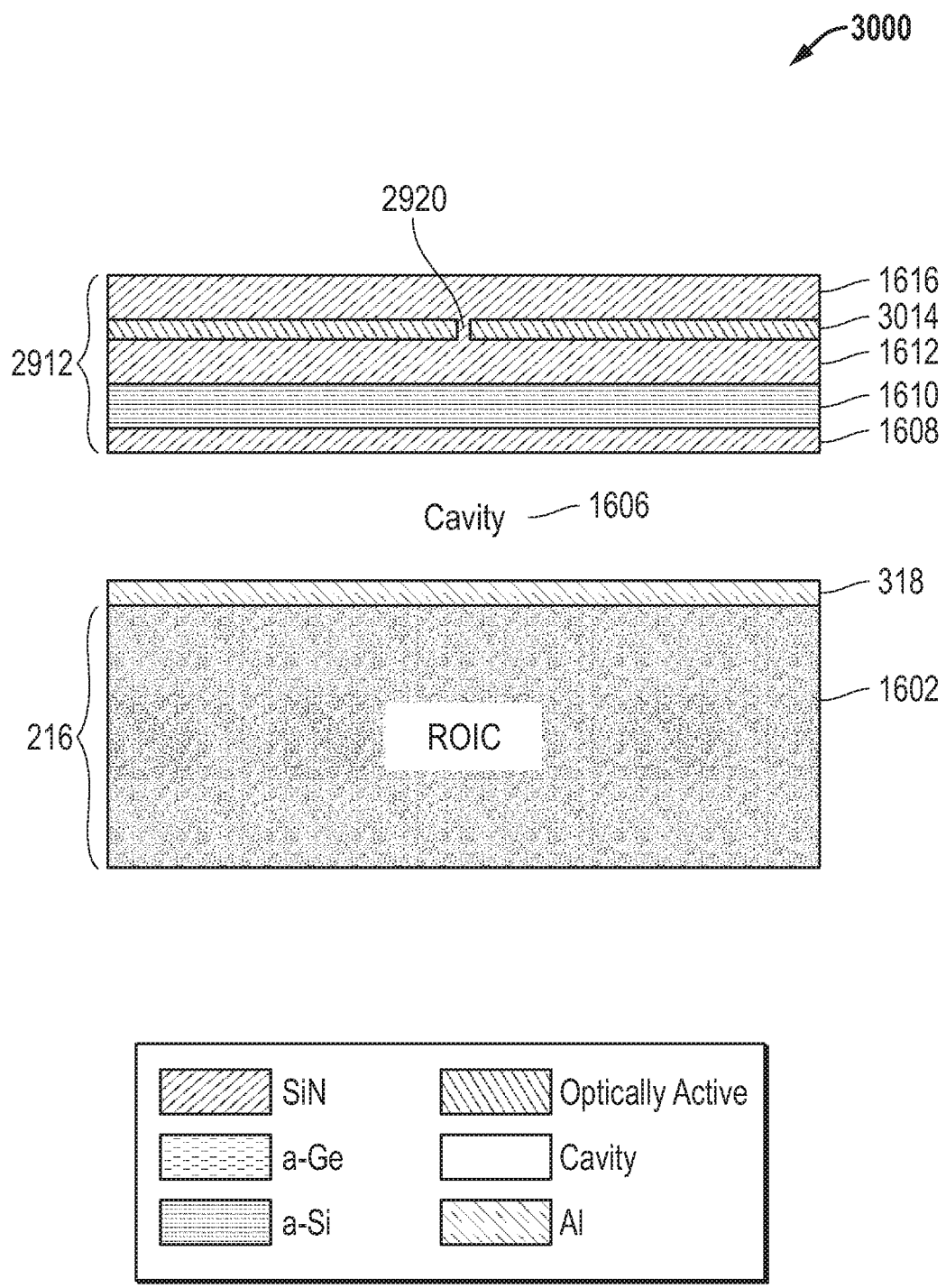
FIG. 30 illustrates a side cross-sectional view of a material layer sequence of an uncooled infrared detector element according to one exemplary embodiment of the disclosed apparatus and methods.

FIG. 30 illustrates a side cross-sectional view of a material layer sequence 3000 for one exemplary embodiment of an uncooled infrared detector element 2900 having an optically transitioning microbolometer pixel membrane structure 2912 that includes one or more optically transitioning materials, such as described and illustrated in relation to FIG. 29. In one embodiment, the layers of FIG. 30 may be formed by deposition on top of a substrate 216 and ROIC 1602 therein. As shown in FIG. 30, layer sequence 2900 includes ROIC 1602 of substrate 216 with optional reflective aluminum layer 318 disposed thereon. A cavity separates substrate 216 and reflective layer 318 from optically transitioning microbolometer pixel membrane structure 2912, which itself includes silicon nitride layers 1608 and 1612 with thermally-electrically active amorphous silicon layer 1610 therebetween. As shown, an optically transitioning material absorber layer 3014 overlays silicon nitride layer 1612, and is overlain itself by silicon nitride layer 1616 to complete microbolometer pixel membrane structure 2912. Optically transitioning material layer 3014 may be, for example, at least one thermochromic composition (e.g., $Ge_xSb_yTe_z$, vanadium oxide ($V_nO_{n-1}$), niobium oxide, tantalum oxide, $Ti_2O_3$, $Fe_3O_4$, $Mo_9O_{26}$, etc.) that acts to selectively transmit radiation depending on temperature. A slit 2920 or other type of discontinuity in absorber 3014 may be provided as shown to interrupt electrical conductivity across the absorber. Slit 2920 is shown in hidden outline in FIG. 29 positioned to interrupt electrical conductivity through absorber layer 3014 between electrically conductive interconnects 308 coupled to opposite ends of microbolometer pixel membrane structure 2912. Any other type of discontinuity in absorber 3014 may be provided to prevent electrical conductivity through absorber layer 3014.

It will be understood that the particular layers illustrated in FIG. 30 for pixel membrane structure 2912 are exemplary only, and may be varied in number, type and/or thicknesses to obtain the desired infrared detection and/or optically transitioning characteristics. Moreover, it will also be understood that a similar microbolometer pixel membrane structure layer sequence 2912 as shown in FIG. 30 may be employed in combination with other detector element configurations of other embodiments disclosed herein if desired, e.g., such as in the detector element 300 of FIG. 3 that includes a monolithic polarizer filter 322 suspended over and above the microbolometer pixel membrane structure, the detector element 1200 of FIG. 12 that includes a monolithic spectral filter 1222 suspended over and above the microbolometer pixel membrane structure 312, and the detector element 1900 of FIG. 20 that includes a microlens structure 1902 suspended over and above the microbolometer pixel membrane structure.

Figure 31:
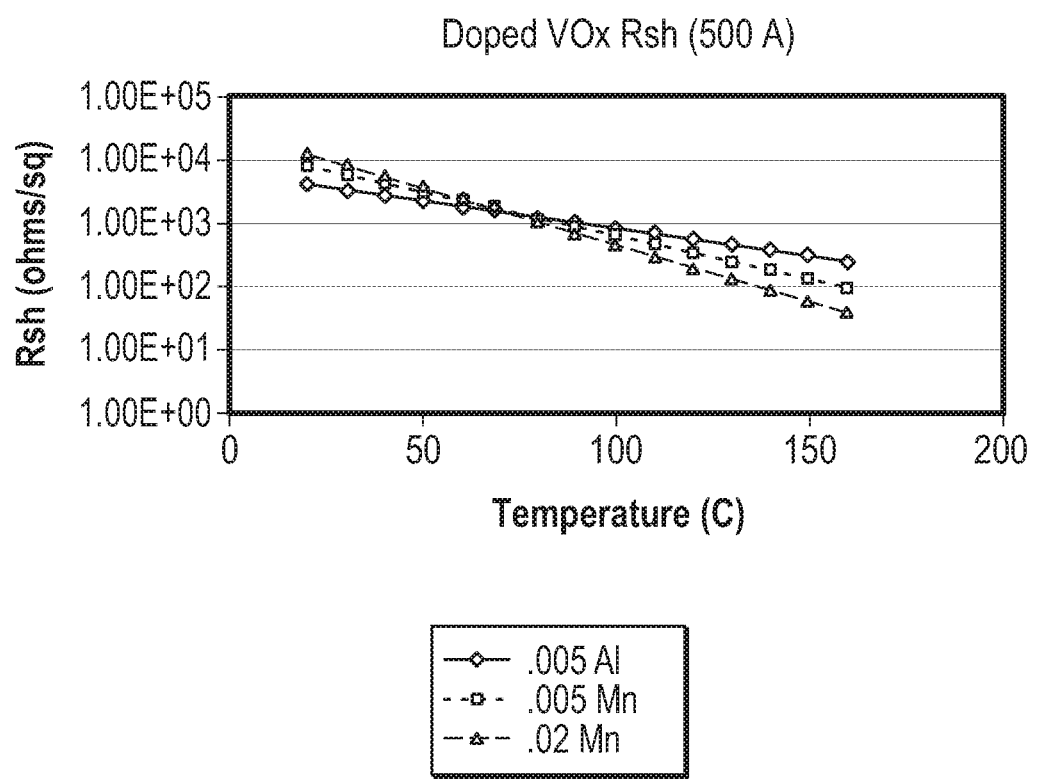
FIG. 31 illustrates sheet resistance (Rsh) versus temperature for various doped compositions of vanadium oxide.
Figure 32:
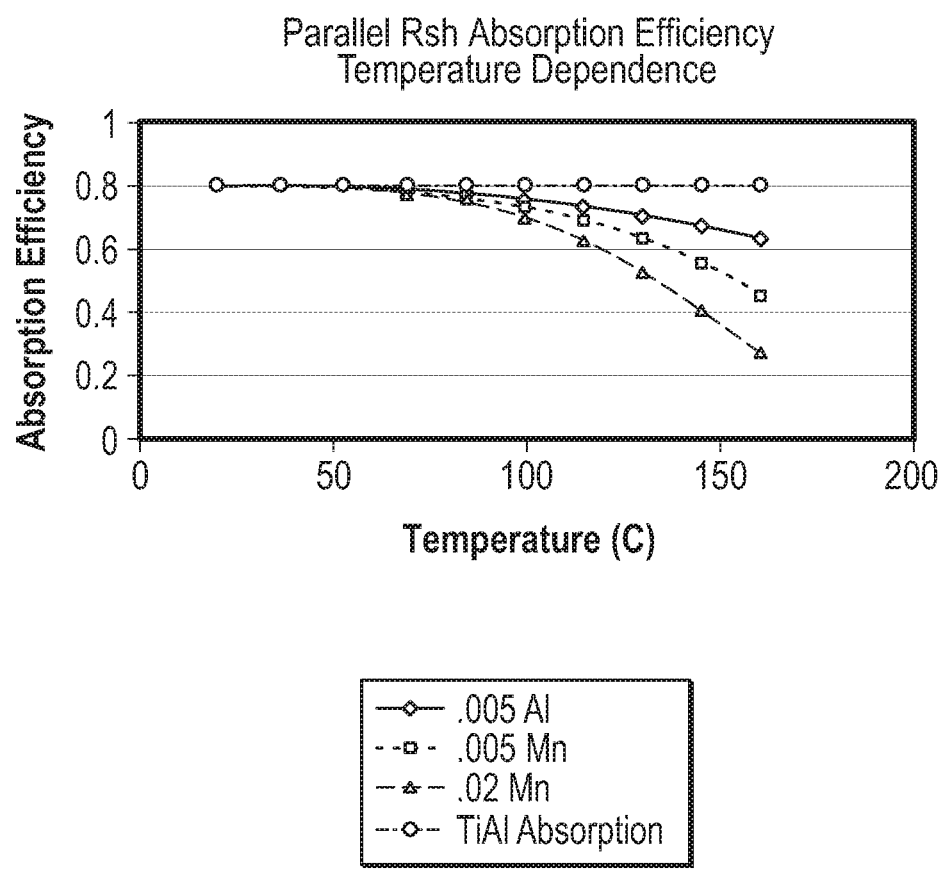
FIG. 32 illustrates temperature dependence of parallel Rsh infrared light absorption efficiency for various doped compositions of vanadium oxide and titanium-aluminum.

FIG. 31 illustrates sheet resistance (Rsh) versus temperature at 500 amps for various doped compositions of vanadium oxide, specifically for 0.005 aluminum doping, for 0.005 manganese doping, and for 0.02 manganese doping. FIG. 32 illustrates temperature dependence of parallel Rsh infrared light absorption efficiency for the same various doped compositions of vanadium oxide that were described in relation to FIG. 31, as well as for titanium-aluminum. As may be seen from the plot of FIG. 32, absorption efficiency of titanium-aluminum remains substantially constant with temperature increase from under 50° C. to above 150° C. However, absorption efficiency of the various optically transitioning vanadium oxide compositions decreases by varying amount with increasing temperatures equal to or greater than about 68° C. Thus, it may be seen that radiation absorption (and therefore temperature) behavior of microbolometer pixel membrane structure 2912 as a function of absorbed radiation may be controlled by selection of an optically transitioning material having the desired radiation absorption versus temperature relationship for the absorber layer of the microbolometer pixel membrane structure.

Figure 33:
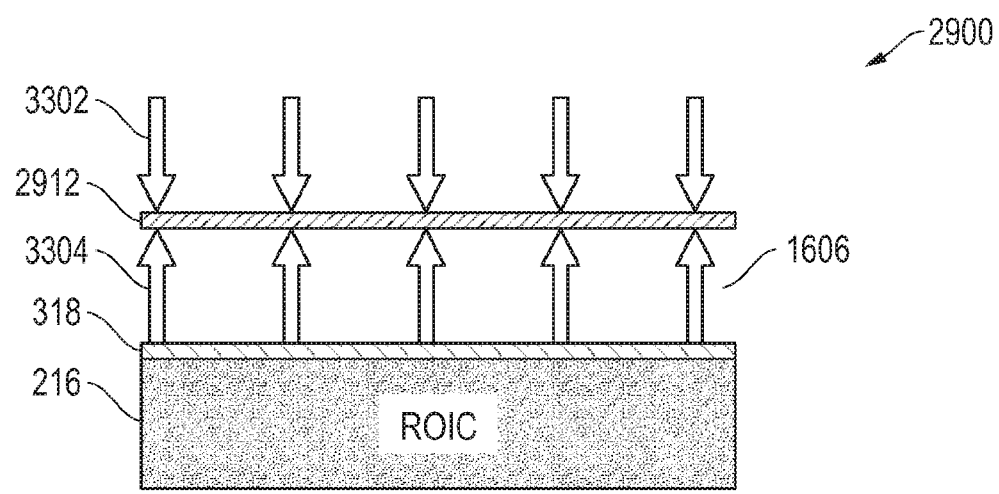
FIG. 33 illustrates a simplified side cross-sectional view of an uncooled infrared detector element according to one exemplary embodiment of the disclosed apparatus and methods.

The simplified illustration of FIG. 33 graphically illustrates how substantially all incoming radiation is either absorbed as radiation 3302 by microbolometer pixel membrane structure 2912 or is transmitted through microbolometer pixel membrane structure 2912 and reflected back up as radiation 3304 to microbolometer pixel membrane structure 2912 at relatively moderate temperatures substantially below the optical transition temperature of the optically transitioning material in the microbolometer pixel membrane structure 2912, e.g., at temperatures less than about 68° C. for an optically transitioning VOx (e.g., $VO_2$) absorber material 3014 having the absorption efficiency characteristics illustrated in FIG. 32.

Figure 34:
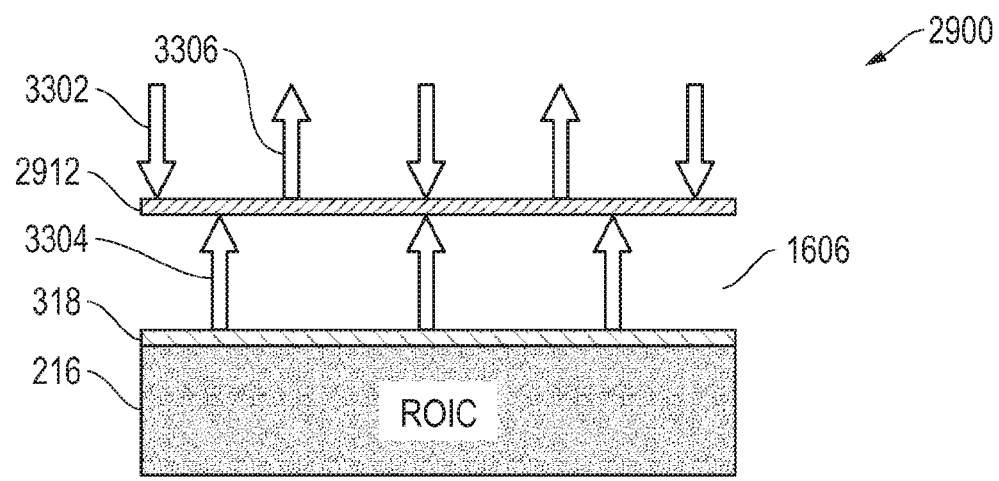
FIG. 34 illustrates a simplified side cross-sectional view of an uncooled infrared detector element according to one exemplary embodiment of the disclosed apparatus and methods.

The simplified illustration of FIG. 34 graphically illustrates how radiation absorption is moderated at relatively higher temperatures that are substantially above the optically transitioning (e.g., thermochromic or phase transitioning) temperature of the material of the microbolometer pixel membrane structure 2912 such that the optical cavity 1606 detunes as temperature rises and such that the pixel temperature is naturally self-limited to provide an increased margin of temperature safety for the underlying amorphous silicon thermally-electrically active layer 1610. In this regard, only a portion of incoming radiation is absorbed as radiation 3302 by microbolometer pixel membrane structure 2912, while the remainder of the incoming radiation is reflected as radiation 3306 by an optically transitioning absorber material of microbolometer pixel membrane structure 2912 at relatively higher temperatures, e.g., at temperatures greater than or equal to about 68° C. for an optically transitioning vanadium oxide (e.g., $VO_2$) absorber material 3014 having the absorption efficiency characteristics illustrated in FIG. 32. As further shown in FIG. 34, less radiation is transmitted through the optically transitioning absorber material of microbolometer pixel membrane structure 2912 and reflected as radiation 3304 back up to microbolometer pixel membrane structure 2912 at such higher temperatures.

In the exemplary embodiment of FIGS. 29 and 30, optically transitioning material may be incorporated into an absorber layer 3014 to advantageously provide optically transitioning characteristics to the microbolometer pixel membrane structure with little or substantially no increase in thermal mass. However, it will be understood that other embodiments of optically transitioning microbolometer pixel membrane structures may be implemented by incorporating optically transitioning material in a part/s of a microbolometer pixel membrane structure other than the absorber layer. For example, a solid or intermittent optically transitioning material layer may be formed on top of a microbolometer pixel membrane structure, e.g., such as formed over a top silicon nitride layer 1616 of a microbolometer pixel membrane structure having a Titanium or Ti—Al absorber layer 1614. Further, it is possible that only a portion/s of the planar area of a microbolometer pixel membrane structure may be provided with optically transitioning material, i.e., such that only a portion of incoming radiation is blocked or reflected by the microbolometer pixel membrane structure with increasing temperature. For example, an intermittent optically transitioning material layer may be provided that by forming a pattern of localized optically transitioning material segments (e.g., as circular dots, square dots, etc.) over a top silicon nitride layer 1616 of a microbolometer pixel membrane structure having a Titanium or Ti—Al absorber layer 1614. In this way, regardless of temperature some radiation always passes through a portion's of the microbolometer pixel membrane structure that is not overlain by optically transitioning material, while radiation is selectively blocked from passing through those portions of the microbolometer pixel membrane structure that are overlain by optically transitioning material.

FIGS. 29-30 and 33-34 illustrate embodiments of an optically transitioning radiation detector configured as an optically transitioning microbolometer pixel membrane structure. However, it will be understood that an optically transitioning radiation detector element may include any other type of thermal detector element that utilizes an optically transitioning thermal absorption structure to sense radiation falling incident thereon by measuring at least one property having a value that changes with temperature and in which the thermal absorption structure is provided with one or more components that are optically transitioning. Examples include, but are not limited to, thermal detector elements that sense radiation by measuring changes in one or more properties of electrical resistance, electrical capacitance, electrical voltage, electrical current, electromotive force, etc. Specific examples of such thermal detector elements include, but are not limited to, thermocouple detectors, ferroelectric detectors, microbolometer detectors, etc.

Thus it will be understood with benefit of this disclosure that an optically transitioning material structure may be associated at the pixel level with an individual radiation detector element (e.g., as an optically transitioning filter element suspended over and above the individual radiation detector element, as an integral part of a radiation detector element such as microbolometer pixel membrane structure, etc.) in a manner such that the optically transitioning material structure associated with a given individual radiation detector element only affects radiation destined for that given individual radiation detector element and without affecting radiation destined for another radiation detector element (e.g., of the same focal plane array). Further as illustrated herein, microbolometer pixel membrane structures and optical elements (including optically transitioning filter elements) may be further characterized as being substantially planar in some embodiments, although this is not always necessary.

It will also be understood that although particular embodiments of the disclosed optical elements have been illustrated in conjunction with microbolometer pixel membrane structures having a diffractive resonant cavity (DRC) configuration, it is also possible that the disclosed optical elements may be implemented with non-DRC microbolometer pixel membrane structure configurations.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed apparatus and methods may be utilized in various combinations and/or independently. Thus the invention is not limited to only those combinations shown herein, but rather may include other combinations.

What is claimed is:

1. A method of making a focal plane array assembly, comprising forming a plurality of individual thermal detector elements arranged as an array, each of at least a portion of the plurality of individual detector elements comprising an optically transitioning thermal absorption structure and being configured to sense radiation falling incident thereon by measuring at least one property of the thermal absorption structure that changes value with temperature, the thermal absorption structure being provided with at least one optically transitioning material that is an integral part of the thermal absorption structure itself; and where the method further comprises:

selecting a composition of the optically transitioning material to tailor the optical transition characteristics of the material as a function of temperature so that the thermal absorption structure absorbs less of the incident radiation as its temperature increases; and viewing a scene with the focal plane array such that a temperature of the optically transitioning material of each of the portion of individual thermal detector elements increases while viewing the scene to cause the optically transitioning material to transition from a semiconducting phase to a metallic phase while viewing the scene.

2. The method of claim 1, further comprising providing a substrate; and where the thermal absorption structure of each of the portion of individual thermal detector elements is a microbolometer pixel membrane structure that provides a membrane suspended above the substrate that is configured to absorb radiation incident thereon, the microbolometer pixel membrane structure of each of the microbolometer pixel membrane structures being disposed in spaced relationship above the substrate to define a cavity therebetween with the one or more optically transitioning material components being formed as an integral part of the membrane itself.

3. The method of claim 1, where each of the portion of individual thermal detector elements is configured such that the optically transitioning material undergoes a semiconducting-to-metallic phase transition with increasing temperature; and where the method further comprises selecting a composition of the optically transitioning material to tailor the semiconducting-to-metallic phase transition characteristics of the material as a function of temperature to selectively filter out radiation while viewing a scene by reflecting the radiation from the thermal absorption structure depending on the temperature of the material so as to control radiation absorption of the thermal absorption structure.

4. The method of claim 3, further comprising viewing a scene with the focal plane array such that a temperature of the optically transitioning material of each of the portion of individual thermal detector elements increases while viewing the scene to cause the optically transitioning material to transition from a semiconducting phase to a metallic phase while viewing the scene to selectively filter out radiation by reflecting the radiation from the thermal absorption structure while viewing the scene with the focal plane array.

5. The method of claim 1, where the method further comprises selecting a composition of the optically transitioning material to exhibit optical transition characteristics that filter out undesired radiation by reflecting the undesired radiation from the thermal absorption structure at one or more selected radiation wavelengths and/or at one or more selected temperatures of the material so as to control radiation absorption of the thermal absorption structure while the thermal detector element is viewing a scene that includes the undesired radiation.

6. The method of claim 1, further comprising:
providing a substrate; and
forming each of the portion of individual thermal detector elements as an uncooled infrared detector;
where the thermal absorption structure of each of the portion of individual thermal detector elements is a microbolometer pixel membrane structure configured to absorb radiation incident thereon, the microbolometer pixel membrane structure being disposed in spaced relationship above the substrate to define a cavity therebetween.

7. The method of claim 1, further comprising:
providing a device wafer and forming the forming the plurality of individual thermal detector elements arranged as an array on the device wafer;
providing a lid wafer, the lid wafer being at least partially transmissive of the incident radiation; and
assembling the lid wafer to the device wafer such that the lid wafer allows the incident radiation to reach the focal plane array assembly through the lid wafer.

8. The method of claim 7, further comprising sealingly assembling the lid wafer to the device wafer with a vacuum therebetween to form a wafer-level packaged focal plane array assembly.

9. The method of claim 1, further comprising selecting a composition of the optically transitioning material to tailor the optical transition characteristics of the material as a function of temperature so that the thermal absorption structure reflects more incident radiation as its temperature increases due to absorbed incident radiation while viewing a scene so as to limit a maximum temperature of the thermal detector element.

10. The method of claim 1, where the optically transitioning material becomes increasingly reflective of incident radiation with increasing temperature such that the thermal absorption structure of each of the portion of individual thermal detector elements absorbs a greater amount of incident radiation at a first temperature than the thermal absorption structure absorbs at a second temperature when the second temperature is higher than the first temperature.

11. The method of claim 10, where the thermal absorption structure of each of the portion of individual thermal detector elements is a microbolometer pixel membrane structure configured to absorb radiation incident thereon, the microbolometer pixel membrane structure being disposed in spaced relationship above the substrate to define a cavity therebetween; and where the method further comprises:
providing a substrate;
forming each of the portion of individual thermal detector elements with a configuration to receive incident radiation on a first side of the microbolometer pixel membrane structure that faces away from the cavity; and
forming a reflective layer on the surface of the substrate of each of the portion of individual thermal detector elements between the microbolometer pixel membrane structure and the substrate such that the optically transitioning material allows a greater portion of the total received incident radiation to be transmitted through the microbolometer pixel membrane structure to the reflective layer of the substrate at a first temperature than the optically transitioning material allows to be transmitted through the microbolometer pixel membrane structure at a second temperature that is higher than the first temperature.

12. A method, comprising:
viewing a scene with a focal plane array that includes a plurality of individual thermal detector elements, at least a portion of the plurality of individual thermal detector elements each comprising an optically transitioning thermal absorption structure provided with at least one optically transitioning material that is an integral part of the thermal absorption structure itself; and
sensing radiation from the scene that falls incident on the thermal detector elements of the focal plane array by measuring at least one property of the thermal absorption structure of each of the thermal detector elements that changes value with temperature;
where the temperature of the optically transitioning material of the thermal absorption structure of each of the portion of individual thermal detector elements of the focal plane array increases due to absorbed incident radiation while viewing the scene to cause the optically transitioning material of the thermal absorption structure to transition from a semiconducting phase to a metallic phase while viewing the scene such that the thermal absorption structure absorbs less of the incident radiation as its temperature increases while viewing the scene.

13. The method of claim 12, further comprising viewing the scene with the optically transitioning material of the thermal absorption structure of each of the portion of individual thermal detector elements of the focal plane array in a semiconducting phase and viewing the scene with the optically transitioning material of the thermal absorption structure of each of the portion of individual thermal detector elements of the focal plane array in a metallic phase; and where the temperature of the optically transitioning material of the thermal absorption structure of each of the portion of individual thermal detector elements of the focal plane array increases due to absorbed incident radiation while viewing the scene to cause the optically transitioning material to transition from a semiconducting phase to a metallic phase to selectively filter out the incident radiation while viewing the scene with the focal plane array so that the thermal absorption structure absorbs less of the incident radiation as its temperature increases.

14. The method of claim 12, further comprising viewing the scene with the optically transitioning material of the thermal absorption structure of each of the portion of individual thermal detector elements of the focal plane array in a semiconducting phase and viewing the scene with the optically transitioning material of the thermal absorption structure of each of the portion of individual thermal detector elements of the focal plane array in a metallic phase; and where the temperature of the optically transitioning material of the thermal absorption structure of each of the portion of individual thermal detector elements of the focal plane array increases due to absorbed incident radiation while viewing the scene to cause the optically transitioning material of the thermal absorption structure to transition such that the thermal absorption structure reflects more incident radiation as its temperature increases due to absorbed incident radiation while viewing the scene so as to limit a maximum temperature of the thermal detector element.

* * * * *